(12) United States Patent
Zatloukal et al.

(10) Patent No.: US 8,492,391 B2
(45) Date of Patent: Jul. 23, 2013

(54) SUBSTITUTED 6-(2-HYDROXYBENZYLAMINO)PURINE DERIVATIVES, THEIR USE AS MEDICAMENTS AND COMPOSITIONS CONTAINING THESE DERIVATIVES

(75) Inventors: Marek Zatloukal, Sumperk (CS); Vladimir Krystof, Olomouc (CS); Libor Havlicek, Praha (CS); Igor Popa, Olomouc (CS); Karel Dolezal, Hlubocky (CS); Miroslav Strnad, Olomouc (CS); Radek Jorda, Olomouc (CS)

(73) Assignees: Univerzita Palackeho V Olomouci, Olomouc (CZ); Biopatterns, S.R.O., Olomouc, Holice (CZ)

( * ) Notice: Subject to any disclaimer, the term of this patent is extended or adjusted under 35 U.S.C. 154(b) by 34 days.

(21) Appl. No.: 13/375,343

(22) PCT Filed: Jun. 2, 2010

(86) PCT No.: PCT/CZ2010/000067
§ 371 (c)(1),
(2), (4) Date: Nov. 30, 2011

(87) PCT Pub. No.: WO2010/139289
PCT Pub. Date: Dec. 9, 2010

(65) Prior Publication Data
US 2012/0070512 A1    Mar. 22, 2012

(30) Foreign Application Priority Data
Jun. 3, 2009   (CS) .................................. 2009-359

(51) Int. Cl.
*C07D 473/16* (2006.01)
*A61K 31/52* (2006.01)
(52) U.S. Cl.
USPC ........................... 514/263.4; 544/264
(58) Field of Classification Search
USPC ........................ 544/264; 514/263.4
See application file for complete search history.

(56) References Cited
U.S. PATENT DOCUMENTS
2003/0187261 A1*  10/2003  Havlicek et al. ............. 544/276

FOREIGN PATENT DOCUMENTS
EP         1348707        10/2003
WO       WO 01/49688       7/2001

OTHER PUBLICATIONS

International Search Report for PCT/CZ2010/000067, (2010).
Siller M. et al.: "Interactions of Olomoucine II with human liver microsomal Cytochrome P450" Drug Metabolism and Disposition, vol. 37, No. 6, Feb. 27, 2009, pp. 1198-1202.
Krystof V. et al.: "Synthesis and biological activity of Olomoucine II" Bioorganic and Medicinal Chemistry, vol. 12, 2002, pp. 3283-3286.
Nisler J. et al.: "Cytokinin receptor antagonists derived from 6-benzylaminopurine" Phytochemistry, vol. 71, Feb. 25, 2010, pp. 823-830.
Travnicek Z. et al.: "The first ironIII) complexes with cyclin-dependent kinase inhibitors: magnetic, spectroscopic (IR ES+MS, NMR, 57Fe Mossbauer), theoretical and biological activity studies" Journal of Inorganic Biochemistry, vol. 104, Dec. 5, 2009 pp. 405-417.

* cited by examiner

*Primary Examiner* — Bruck Kifle
(74) *Attorney, Agent, or Firm* — Notaro, Michalos & Zaccaria P.C.

(57) ABSTRACT

The invention relates to substituted 6-(2-hydroxybenzylamino)purines of general formula I, to their activity as cyclin-dependent kinases 2, 5, 7 and 9 inhibitors and to their use as medicaments, particularly in the treatment of disorders involving cell proliferation or inflammation. The invention further includes pharmaceutical compositions containing the substituted 6-(2-hydroxybenzylamino)purines.

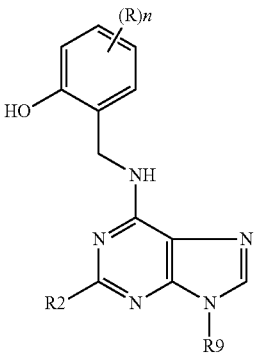

6 Claims, 3 Drawing Sheets

I

SUBSTITUTED 6-(2-HYDROXYBENZYLAMINO)PURINE DERIVATIVES, THEIR USE AS MEDICAMENTS AND COMPOSITIONS CONTAINING THESE DERIVATIVES

FIELD OF THE INVENTION

This invention relates to novel substituted 6-(2-hydroxybenzylamino)purine derivatives, to their activity as polyspecific inhibitors of cyclin-dependent kinases 2, 5, 7, and 9 and to their use as medicaments.

BACKGROUND ART

The cyclin-dependent kinases (CDKs) are heterodimeric complexes composed of a catalytic kinase subunit and a regulatory cyclin subunit, and comprise a family divided into two groups based on their roles in cell cycle progression and transcriptional regulation (Meyerson M. et al.: EMBO J. 11:2909-2917, 1992). Members of the first group comprise core components of the cell cycle machinery, and include cyclin D-dependent kinases 4 and 6, as well as cyclin E-CDK2 complexes, which sequentially phosphorylate the retinoblastoma protein (Rb), to facilitate the G1-S transition (Sherr, C. J.: Cell 79: 551-555, 1994.). Cyclin A-dependent kinases 2 and 1 and cyclin B-CDK1 complexes are required for orderly S-phase progression and the G2-M transition, respectively. CDKs are regulated by positive phosphorylation, directed by CDK-activating kinase (CAK; cyclin H/cdk7/MAT1, Harper, J. W. et al.: Genes Dev. 12: 285-289, 1998), as well as negative phosphorylation events (Morgan, D. O.: Nature 374: 131-134, 1995), and their association with cyclins and endogenous Cip/Kip or INK4 inhibitors (Sherr, C. J. and Roberts, J. M.: Genes Dev. 9: 1149-1163, 1995). In malignant cells, an altered expression of CDKs and their modulators, including overexpression of cyclins and loss of expression of CDK inhibitors, results in deregulated CDK activity, providing a selective growth advantage. In contrast to CDKs governing the transitions between cell cycle phases, transcriptional CDKs, including cyclin H-CDK7, and cyclin T-CDK9 (pTEFb), promote initiation and elongatin of nascent RNA transcripts by phosphorylating the carboxyterminal domain (CTD) of RNA polymerase II (Meinhart, A. et al.: Gens. Dev. 19: 1401-1415, 2005). Because of their critical role in cell cycle progression and cellular transcription, as well as the association of their activities with apoptotic pathways, the CDKs comprise an attractive set of targets for novel anticancer drug development.

The first reported pharmacological CDK inhibitors (6-dimethylaminopurine and isopentenyladenine) were neither particularly active nor selective. However, they provided the first grasp on inhibitory structures, and constituted the starting point for the search for more potent and selective inhibitors. More than 50 inhibitors have so far been described. Their structures were recently extensively reviewed (Fischer, P. M., Gianella-Borradori, A.: Expert Opin. Investic. Drugs 14: 457-469, 2005). Despite striking chemical diversity, all CDK inhibitors share some common properties: (1) they have low molecular weights (<600); (2) they are flat, hydrophobic heterocycles; (3) they act by competing with ATP for binding in the kinase ATP-binding site; (4) they bind mostly by hydrophobic interactions and hydrogen bonds with the kinase; and (5) the backbone carbonyl and amino side-chains of Leu83 act, respectively, as an H-bond acceptor and an H-bond donor to the inhibitors, whereas the backbone carbonyl of Glu81 often acts as an H-bond acceptor. The atomic interaction between inhibitors and CDKs is extensively described (Hardcastle, I. R. et al.: Annu. Rev. Pharmacol. Toxicol. 42: 325-348, 2002). Interestingly, inhibitors of CDKs that act via mechanisms other than competing with ATP have not been described, despite intensive screening and despite the other obvious possibilities of kinase inhibition (e.g. competition with substrate, interference with cyclin binding, and simulation of the natural protein inhibitors).

CDK inhibitors fall into three categories, pan-CDK inhibitors (e.g., deschloroflavopiridol, flavopiridol, oxindole 16 and oxindole 91), those that inhibit CDK1/2/5 (and possibly CDK9) (e.g., olomoucine, (R)-roscovitine, purvalanol B, aminopurvalanol (NG97), hymenialdisine, indirubin-3'-monoxime, indirubin-5-sulfonate, SU9516 and alsterpaullone), and those that are selective for CDK4/6 (e.g. fascaplysin, PD0183812, and CINK4). Only a limited number of inhibitors selective for a single CDK have been described. This is probably due to the conservation of the amino acids lining the CDK ATP-binding pocket (Shapiro, G. I. J. Clin. Oncol. 24:1770-1783, 2006).

The carboxy-terminal domain (CTD) of RNA polymerase II is regulated by phosphorylation mediated by CDKs. The human RNA polymerase II CTD contains 52 tandem repeats of the consensus heptapeptide sequence. Cyclin T-CDK9 (also so called P-TEFβ) preferentially phosphorylates the Ser2 sites of this sequence to promote transcriptional elongation. It is likely that cyclin T-CDK9 can phosphorylate the Ser5 position as well (Palancade, B., Bensaude, O.: Eur. J. Biochem. 270: 3859-3870, 2003). Cyclin H-CDK7/MAT1, in the complex of transcription factor TFIIH, preferentially phosphorylates Ser5, which facilitates promoter clearance and transcriptional initiation (Meinhart, A. et al.: Gens. Dev. 19: 1401-1415,2005). Cyclin H-CDK7 therefore plays a role both as cell cycle and transcriptional CDK; it acts as both CAK and CTD kinase.

Flavopiridol is the most potent known inhibitor of CDK9 (Chao, S. H., Price, D. H.: J. Biol. Chem. 276: 31793-31799, 2001). Whereas the $IC_{50}$ values for other CDKs range from 100 to 400 nmol/L with $K_i$ values between 40 and 70 nmol/L, the binding of flavopiridol to the ATP binding site of CDK9 is significantly tighter ($K_i$ =3 nmol/L). Therefore, the inhibition by flavopiridol of CDK9, as well as CDK7, has profound effects on cellular transcription (Lu, X. Et al. Mol. Cancer ther. 3:861-872, 2004). Seliciclib® (R-roscovitine) also inhibits cyclin T-CDK9 and cyclin H-CDK7 in addition to cyclin E-CDK2 (McClue, S. J. et al. Int. J. Cancer 102: 463-468, 2002) and affects RNA polymerase II CTD phosphorylation, which is associated with a decrease in MCl-1 as well as other antiapoptotic proteins in CLL cells (Alvi, A. J. et al. Blood 105: 4484-4491, 2005). The proapoptotic activity of both flavopiridol and seliciclib in multiple myeloma cell lines occurs by a similar mechanism (Raje, N. et al. Blood 106: 1042-1047, 2005).

Our current work is focused on development of novel classes of compounds potently targeting cell cycle with variable effects on the transcriptional CDK7 and 9. Some of these inhibitors have already been described and originate from different classes of compounds, i.e. purines (Olomoucine II, Kryštof V. et al. Cell. Mol. Life Sci. 62, 1763-1771, 2005) and arylazopyrazoles (Kryštof, V. et al. J. Med. Chem. 49: 6500-6509, 2006). Based on our present knowledge of inhibitor/CDK7/9 interactions, we designed a second-generation inhibitors acting at concentrations close to the cellular concentrations of the kinases.

The present invention provides a series of novel substituted 6-(2-hydroxybenzylamino)purine derivatives that are useful for inhibition of cyclin-dependent kinase 5, 7 and 9. This group of new purine derivatives is characterised by an unusual CDK inhibitory activity thus bringing not only strong anticancer properties to the compounds but also up to now unknown anti-inflammatory activity. Hence they can be used as antimitotic and apoptotic drugs, particularly as anticancer drugs in treatments of metastatic tumors. It is the aim of this invention to provide new anticancer compounds having improved selectivity and efficiency index, i.e. that are less toxic yet more efficacious than the analogues known heretofore.

DISCLOSURE OF THE INVENTION

Object of the present invention are substituted 6-(2-hydroxybenzylamino) purines of the general formula I

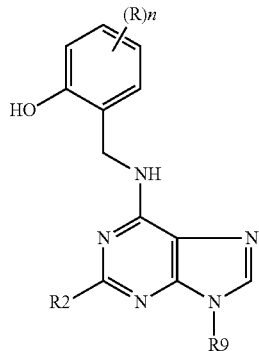

I wherein
$(R)_n$ represents 1 to 4 substituents (n is 1-4), which can be the same or different, the substituents being selected from the group comprising alkyl, alkoxy, amino, halogen, hydroxy, mercapto and nitro, and
R2 is R2'-NH— wherein
R2' is selected from the group consisting of alkyl, alkenyl, cycloalkyl, cycloalkyl alkyl, aryl and arylalkyl, wherein each of the groups can optionally be substituted by one or more substituents selected from the group comprising amino, hydroxy, mercapto, and alkoxy, and
R9 is selected from the group consisting of alkyl, alkenyl, cycloalkyl, cycloalkyl alkyl, aryl and arylalkyl group
and the pharmaceutically acceptable salts thereof, such as salts with alkali metals, ammonium or amines, or addition salts with acids.

As used herein, and unless modified by the immediate context, the generic substituent groups have the following meanings:
alkoxy denotes the group —O—$R_a$, wherein $R_a$ is alkyl or cycloalkyl,
amino denotes the group —$NH_2$,
halogen is selected from the group comprising fluorine, bromine, chlorine and iodine atom,
hydroxy denotes the group —OH,
mercapto denotes the group —SH,
nitro denotes the group —$NO_2$,
alkyl denotes
    branched or unbranched alkyl chain containing 1 to 8 carbon atoms, preferably methyl, ethyl, propyl, isopropyl, butyl, isobutyl, pentyl, isopentyl, hexyl, isohexyl.
alkenyl denotes
    branched or unbranched alkenyl chain containing 2 to 7 carbon atoms, preferably selected from the group containing vinyl, allyl, 1-propenyl, 1-methylethenyl, but-1 to 3-enyl, pent-1 to 4-enyl, isopentenyl, 3,3-dimethylalkyl, hex-1 to 5-enyl, hept-1 to 6-enyl,
cycloalkyl denotes
    a monocyclic or polycyclic alkyl group containing 3 to 15 carbon atoms, preferably cyclopropyl, cyclohexyl or cyclopentyl,
cycloalkyl alkyl denotes
    a group —$R_b$(cycloalkyl) wherein cycloalkyl refers to a cycloalkyl group as defined above and $R_b$ is alkylene bridging group containing 1 to 6 carbon atoms,
aryl denotes
    an aromatic carbocyclic group containing 6 to 18 carbon atoms, which is formed by at least one aromatic ring or multiple condensed rings, from which at least one ring is aromatic, preferably aryl is phenyl,
arylalkyl denotes
    a group —$R_c$—Ar, wherein Ar refers to an aryl group and $R_c$ is alkylene bridging group containing 1 to 6 carbon atoms, preferably methylene. Preferably, arylalkyl is benzyl.

When chiral centers are present in the molecule, the present invention encompasses optically active isomers, their mixtures and racemates.

It is an object of this invention to provide substituted 6-(2-hydroxybenzylamino)purines of the general formula I for use as medicaments.

It is an object of this invention to provide substituted 6-(2-hydroxybenzylamino)purines of the general formula I for use as inhibitors of cyclin-dependent kinases (CDKs), preferably CDK 2, 5, 7, and/or 9.

It is another object of this invention to provide substituted 6-(2-hydroxybenzylamino)purines of the general formula I for use for inhibiting cell proliferation and/or inducing apoptosis.

It is an object of this invention to provide substituted 6-(2-hydroxybenzylamino)purines of the general formula I for use in the treatment of disorders selected from the group comprising cancer, asthma, cardiovascular, neurodegenerative and inflammatory diseases.

It is a further object of this invention to provide substituted 6-(2-hydroxybenzylamino)purines of the general formula I for use in the manufacture of a medicament for the treatment of disorders which involve cell proliferation, such as cancer, restenosis, rheumatoid arthritis, lupus, type I diabetes, multiple sclerosis, Alzheimer's disease, growth of parasites (animal, fungi, protists), graft rejection (host versus graft disease), graft versus host disease, and gout.

In another embodiment, this invention is a method for inhibiting CDKs, particulary for selectively inhibiting CDK 2, 5, 7 and/or 9, and cell proliferation and/or for inducing apoptosis in a mammal, comprising administering a therapeutically effective amount of the composition of formula 1 to the mammal. The CDK inhibiting molecules are useful for treating disorders involving cell proliferation, such as cancer, restenosis, rheumatoid arthritis, lupus, type I diabetes, multiple sclerosis, Alzheimer's disease, growth of parasites (animal, protists), graft rejection (host versus graft disease), graft versus host disease, and gout.

In addition to other CDK-related kinases, CDK 2, 5, 7, and 9 kinase controls certain steps of cell division cycles, in particular the transition from $G_1$ phase into the S phase and in particular the transition from the $G_2$ phase into the M-phase. On the basis of these findings, it can be expected that the compounds of the formula I and their pharmaceutically acceptable salts can be used as antimitotic compounds and for treatment of proliferative diseases, such as cancer and restenosis. Thus in very low concentration (micromolar and lower), they are capable of inhibiting cell cycle transitions ($G_1/S$, $G_2/M$, M-phase/metaphase) carried out on various animal bodies and embryos. Furthermore, the compounds are useful in treating auto-immune diseases, e.g. rheumatoid arthritis, lupus, type I diabetes, multiple sclerosis, etc.; in treating Alzheimer's disease, cardiovascular disease such as restenosis, graft rejection (host vs. graft disease), graft vs. host disease, gout; and in treating cancer, polycystic kidney disease and other proliferative diseases whose pathogenesis involves abnormal cell proliferation.

In addition to therapeutic applications (e.g., for both human and veterinary uses) it will be apparent the subject compounds can be used as a cell culture additive for controlling proliferative and/or differentiation states of cells in vitro, for instance, by controlling the level of activation of a CDK2/CDK5/CDK7/CDK9.

It is likely that inhibition by the compounds of the invention of the catalytic activity of cyclin-dependent kinases in mediated by interaction of the compounds at the ATP-binding site of the enzyme. Such compounds are particularly desirable for reducing excessive cell growth, since they allow inhibition of the kinase activity regardless of the cause underlying the excessive kinase activity leading to excessive cell proliferation. Thus, the compounds of the invention are active in situations in which the excessive kinase activity results from the kinase being a mutated hyperactive form of the kinase and situations in which the kinase is present at excessive levels. Such compounds can also block excessive kinase activity in situations in which the cyclin regulating the kinase is present at excessive levels or its binding to the kinase is enhanced. Furthermore, compounds which block kinase activity by interacting with the ATP binding site of the enzyme are also useful for inhibiting kinase activity in the situations in which a natural inhibitor of cyclin-kinase complexes is mutated.

Substituted-6-(2-hydroxybenzylamino)purine derivatives can be used in the treatment of disorders involving CDK5. Angiostatin-induced inhibition of endothelial cell proliferation/apoptosis is associated with the down-regulation of cell cycle regulatory protein CDK5. CDK5, p35, and p25 proteins were all expressed in invasive cancer cells but it was also shown that CDK5 expression regulates cancer cell proliferation. In addition, a potent mitogen βFGF up-regulates CDK5 expression. The novel derivatives specifically inhibit CDK5 expression/activity in a dose-dependent manner with concomitant inhibition of invasive cancer cell proliferation and induction of apoptosis.

Cyclin-dependent kinase-5 (CDK5) is also expressed in neuronal cells and plays an important role in neurite outgrowth, of neuronal migration and neurogenesis, however, its functions in non-neuronal cells remain unclear. CDK5 is expressed at high levels in proliferating bovine aortic (BAE) cells, in contrast to the insignificant low levels of CDK5 expression in quiescent BAE cells. In addition, βFGF up-regulates CDK5 expression in a dose-dependent fashion. Angiostatin (AS) inhibits ECs proliferation in dose-dependent manner with concomitant down-regulation of CDK5 expression. The role of CDK5 in ECs, proliferation and apoptosis was confirmed by selective inhibition of CDK5 expression by the new purine derivatives, which inhibits βFGF-stimulated BAE cells proliferation and induces apoptosis in dose-specific manner.

The invention also relates to novel compounds for activating p53, the mammal cell's own natural brake gene for stopping uncontrolled cell proliferation (cancer), thus being able to switch off the cancer. p53 as well as retinoblastoma (Rb) are two well characterised tumour suppressors whose inactivation may lead to uncontrolled cell proliferation and malignancy. Phosphorylation of these two proteins, which are involved in the cell cycle regulatory mechanisms, is known to modulate their function. Thus, potent p53 regulators represent a good tool for treatment of cancers due to the induction of wild type p53 protein in cancers.

Studies carried out on the derivatives of the invention have demonstrated, in addition, a strong effect on apoptosis of many cancer cell lines. It has been seen that apoptosis can be induced at stage $G_1$ or $G_2$ and following damage of the DNA, some cells stop at stage $G_1$ and p53-dependent apoptotic pathway is then induced. In other situations, it seems that cells stop at $G_2/M$ stage in response to the damage caused to the DNA, and the activation of an independent p53 apoptotic path is observed. This path has proved particularly significant in the therapy of tumours in which a less active p53 is observed. By the application of the derivatives of the invention, the p53-independent apoptosis will be stimulated in cells, which have stopped at stage $G_2$ through the damage to the DNA using agents such as mitoxantrone or cis-platinum. The CDK inhibitors of this invention can thus increase the therapeutic potential of the anti-tumor agents currently used.

The invention also includes a pharmaceutical composition, which comprises at least one substituted 6-(2-hydroxybenzylamino)purine, and a pharmaceutically acceptable carrier.

The novel compounds of this invention can be used per se or as intermediates in the preparation of novel compounds having a wide variety of diagnostic, therapeutic and industrial utilities.

The following derivatives of formula I are particularly preferred, namely: 2-({6-[(2-hydroxy-5-chlorobenzyl)amino]-9-(methyl, ethyl, isopropyl, 3-pentyl, cyclohexyl, benzyl)-9H-purin-2-yl}amino)butan-1-ol, $N^6$-(2-hydroxy-5-chlorobenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-5-chlorobenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-5-chlorobenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-5-chlorobenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-5-chlorobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-chlorobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-chlorobenzyl)amino]-9-(methyl, ethyl, isopropyl, 3-pentyl, cyclohexyl, benzyl)-9H-purin-2-yl}amino)-2-methyl-pentan-2-ol, 1-({6-[(2-hydroxy-5-chlorobenzyl)amino]-9-(methyl, ethyl, isopropyl, 3-pentyl, cyclohexyl, benzyl)-9H-purin-2-yl}amino)propan-2-ol, 4-({6-[(2-hydroxy-5-chlorobenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-5-chlorobenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-5-chlorobenzyl)amino]-9-(methyl, ethyl, isopropyl, 3-pentyl, cyclohexyl, benzyl)-9H-purin-2-yl]amino}pentan-2-ol, 1-({6-[(2-hydroxy-5-chlorobenzyl)amino]-9-(methyl, ethyl, isopropyl, 3-pentyl, cyclohexyl, benzyl)-9H-purin-2-yl}amino)-2-methyl-propan-2-ol, 2-({6-[(2-hydroxy-3-chlorobenzyl)amino]-9-(methyl, ethyl, isopropyl, 3-pentyl, cyclohexyl, benzyl)-9H-purin-2-yl}amino)butan-1-ol, $N^6$-(2-hydroxy-3-chlorobenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-3-chlorobenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-3-chlorobenzyl)-$N^2$-(4-aminocyclohexyl)-9-(methyl, ethyl, isopropyl, 3-pentyl, cyclohexyl, benzyl)-9H-purin-2,6-diamine, $N^6$-(2-hydroxy-3-chlorobenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-3-chlorobenzyl)amino]-9-(methyl, ethyl, isopropyl, 3-pentyl, cyclohexyl, benzyl)-9H-purin-2-yl}amino)propan-2-ol, 1-({6-[(2-hydroxy-3-chlorobenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-3-chlorobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-3-chlorobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-3-chlorobenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-3-chlorobenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-3-chlorobenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-3-chlorobenzyl)amino]-9-(methyl, ethyl, isopropyl, 3-pentyl, cyclohexyl, benzyl)-9H-purin-2-yl]amino}pentan-2-ol, 1-({6-[(2-hydroxy-3-chlorobenzyl)amino]-9-(methyl, ethyl, isopropyl, 3-pentyl, cyclohexyl, benzyl)-9H-purin-2-yl}amino)-2-methyl-propan-2-ol, 2-({6-[(2-hydroxy-5-fluorobenzyl)amino]-(methyl, ethyl, isopropyl, 3-pentyl, cyclohexyl, benzyl)-9H-purin-2-yl}amino)butan-1-ol, $N^6$-(2-hydroxy-5-fluorobenzyl)-$N^2$-(2-aminopropyl)-9-(methyl, ethyl, isopropyl, 3-pentyl, cyclohexyl, benzyl)-9H-purin-2,6-diamine, 1-({6-[(2-hydroxy-5-fluorobenzyl)amino]-9-(methyl, ethyl, isopropyl, 3-pentyl, cyclohexyl, benzyl)-9H-purin-2-yl}amino)propan-2-ol, 2-({6-[(2-hydroxy-5-fluorobenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-5-fluorobenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-5-fluorobenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-5-fluorobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-fluorobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-fluorobenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-5-fluorobenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-5-fluorobenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-5-fluorobenzyl)amino]-9-(methyl, ethyl, isopropyl, 3-pentyl, cyclohexyl, benzyl)-9H-purin-2-yl]amino}pentan-2-ol, 1-({6-[(2-hydroxy-5-fluorobenzyl)amino]-9-(methyl, ethyl, isopropyl, 3-pentyl, cyclohexyl, benzyl)-9H-purin-2-yl}amino)-2-methyl-propan-2-ol, 2-({6-[(2-hydroxy-5-iodobenzyl)amino]-9-(methyl, ethyl, isopropyl, 3-pentyl, cyclohexyl, benzyl)-9H-purin-2-yl}amino)butan-1-ol, $N^6$-(2-hydroxy-5-iodobenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-5-iodobenzyl)amino]-9-(methyl, ethyl, isopropyl, 3-pentyl, cyclohexyl, benzyl)-9H-purin-2-yl}amino)-3-methyl-butan-1-ol, 1-({6-[(2-hydroxy-5-iodobenzyl)amino]-9-(methyl, ethyl, isopropyl, 3-pentyl, cyclohexyl, benzyl)-9H-purin-2-yl}amino)propan-2-ol, 1$N^6$-(2-hydroxy-5-iodobenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-5-iodobenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-5-iodobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-iodobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-iodobenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-5-iodobenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-5-iodobenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-5-iodobenzyl)amino]-9-(methyl, ethyl, isopropyl, 3-pentyl, cyclohexyl, benzyl)-9H-purin-2-yl]amino}pentan-2-ol, 1-({6-[(2-hydroxy-5-iodobenzyl)amino]-9-(methyl, ethyl, isopropyl, 3-pentyl, cyclohexyl, benzyl)-9H-purin-2-yl}amino)-2-methyl-propan-2-ol, 2-({6-(2,5-dihydroxybenzyl)amino]-9-(methyl, ethyl, isopropyl, 3-pentyl, cyclohexyl, benzyl)-9H-purin-2-yl}amino)butan-1-ol, $N^6$-(2,5-dihydroxybenzyl)amino]-$N^2$-(2-aminopropyl)-9-(methyl, ethyl, isopropyl, 3-pentyl, cyclohexyl, benzyl)-9H-purin-2,6-diamine, 2-({6-(2,5-dihydroxybenzyl)amino]-9-(methyl, ethyl, isopropyl, 3-pentyl, cyclohexyl, benzyl)-9H-purin-2-yl}amino)-3-methyl-butan-1-ol, $N^6$-(2,5-dihydroxybenzyl)amino]-$N^2$-(4-aminocyclohexyl)-9-(methyl, ethyl, isopropyl, 3-pentyl, cyclohexyl, benzyl)-9H-purin-2,6-diamine, 1-({6-(2,5-dihydroxybenzyl)amino]-9-(methyl, ethyl, isopropyl, 3-pentyl, cyclohexyl, benzyl)-9H-purin-2-yl}amino)-2-methyl-propan-2-ol, 3-({6-(2,5-dihydroxybenzyl)amino]-9-(methyl, ethyl, isopropyl, 3-pentyl, cyclohexyl, benzyl)-9H-purin-2-yl}amino)-2-methyl-butan-2-ol, 4-({6-(2,5-dihydroxybenzyl)amino]-9-(methyl, ethyl, isopropyl, 3-pentyl, cyclohexyl, benzyl)-9H-purin-2-yl}amino)-2-methyl-butan-2-ol, 4-({6-(2,5-dihydroxybenzyl)amino]-9-(methyl, ethyl, isopropyl, 3-pentyl, cyclohexyl, benzyl)-9H-purin-2-yl}amino)-2-methyl-pentan-2-ol, 4-({6-(2,5-dihydroxybenzyl)amino]-9-(methyl, ethyl, isopropyl, 3-pentyl, cyclohexyl, benzyl)-9H-purin-2-yl}amino)-2,3-dimethyl-butan-2-ol, 3-({6-(2,5-dihydroxybenzyl)amino]-9-(methyl, ethyl, isopropyl, 3-pentyl, cyclohexyl, benzyl)-9H-purin-2-yl}amino)-2-methyl-pentan-2-ol, 3-({6-(2,5-dihydroxybenzyl)amino]-9-(methyl, ethyl, isopropyl, 3-pentyl, cyclohexyl, benzyl)-9H-purin-2-yl]amino}pentan-2-ol, 1-({6-(2,5-dihydroxybenzyl)amino]-9-(methyl, ethyl, isopropyl, 3-pentyl, cyclohexyl, benzyl)-9H-purin-2-yl}amino)-2-methyl-propan-2-ol, 1-({6-[(2,5-dihydroxybenzyl)amino]-9-(methyl, ethyl, isopropyl, 3-pentyl, cyclohexyl, benzyl)-9H-purin-2-yl}amino)propan-2-ol, 2-({6-(2,5-([hydroxybenzyl)amino]-9-(methyl, ethyl, isopropyl, 3-pentyl, cyclohexyl, benzyl)-9H-purin-2-yl}amino)butan-1-ol, 2 $N^6$-(2,5-dihydroxybenzyl)amino]-$N^2$-(2-aminopropyl)-9-(methyl, ethyl, isopropyl, 3-pentyl, cyclohexyl, benzyl)-9H-purin-2,6-diamine, 2-({6-(2,5-dihydroxybenzyl)amino]-9-(methyl, ethyl, isopropyl, 3-pentyl, cyclohexyl, benzyl)-9H-purin-2-yl}amino)-3-methyl-butan-1-ol, $N^6$-(2,5-dihydroxybenzyl)amino]-$N^2$-(4-aminocyclohexyl)-9-(methyl, ethyl, isopropyl, 3-pentyl, cyclohexyl, benzyl)-9H-purin-2,6-diamine, 1-({6-(2,5-dihydroxybenzyl)amino]-9-(methyl, ethyl, isopropyl, 3-pentyl, cyclohexyl, benzyl)-9H-purin-2-yl}amino)-2-methyl-propan-2-ol, 3-({6-(2,5-dihydroxybenzyl)amino]-9-(methyl, ethyl, isopropyl, 3-pentyl, cyclohexyl, benzyl)-9H-purin-2-yl}amino)-2-methyl-butan-2-ol, 4-({6-(2,5-dihydroxybenzyl)amino]-9-(methyl, ethyl, isopropyl, 3-pentyl, cyclohexyl, benzyl)-9H-purin-2-yl}amino)-2-methyl-butan-2-ol, 4-({6-(2,5-dihydroxybenzyl)amino]-9-(methyl, ethyl, isopropyl, 3-pentyl, cyclohexyl, benzyl)-9H-purin-2-yl}amino)-2-methyl-pentan-2-ol, 4-({6-(2,5-dihydroxybenzyl)amino]-9-(methyl, ethyl, isopropyl, 3-pentyl, cyclohexyl, benzyl)-9H-purin-2-yl}amino)-2,3-dimethyl-butan-2-ol, 3-({6-(2,5-dihydroxybenzyl)amino]-9-(methyl, ethyl, isopropyl, 3-pentyl, cyclohexyl, benzyl)-9H-purin-2-yl}amino)-2-methyl-pentan-2-ol, 3-({6-(2,5-dihydroxybenzyl)amino]-9-(methyl, ethyl, isopropyl, 3-pentyl, cyclohexyl, benzyl)-9H-purin-2-yl]amino}pentan-2-ol, 1-({6-(2,5-dihydroxybenzyl)amino]-9-(methyl, ethyl, isopropyl, 3-pentyl, cyclohexyl, benzyl)-9H-purin-2-yl}amino)-2-methyl-propan-2-ol,
1-({6-[(2,5-dihydroxybenzyl)amino]-9-(methyl, ethyl, isopropyl, 3-pentyl, cyclohexyl, benzyl)-9H-purin-2-yl}amino)propan-2-ol, 2-({6-[(2-hydroxy-5-methylbenzyl)amino]-9-(methyl, ethyl, isopropyl, 3-pentyl, cyclohexyl, benzyl)-9H-purin-2-yl}amino)butan-1-ol, $N^6$-(2-hydroxy-5-methylbenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-5-methylbenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-5-methylbenzyl)-$N^2$-(4-aminocyclohexyl)-9-(methyl, ethyl, isopropyl, 3-pentyl, cyclohexyl, benzyl)-9H-purin-2,6-diamine, $N^6$-(2-hydroxy-5-methylbenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-5-methylbenzyl)amino]-9-(methyl, ethyl, isopropyl, 3-pentyl, cyclohexyl, benzyl)-9H-purin-2-yl}amino)-2-methyl-propan-2-ol, 1-({6-[(2-hydroxy-5-methylbenzyl)amino]-9-(methyl, ethyl, isopropyl, 3-pentyl, cyclohexyl, benzyl)-9H-purin-2-yl}amino)propan-2-ol, 3-({6-[(2-hydroxy-5-methylbenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-methylbenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-methylbenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-5-methylbenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-5-methylbenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-5-methylbenzyl)amino]-9-(methyl, ethyl, isopropyl, 3-pentyl, cyclohexyl, benzyl)-9H-purin-2-yl]amino}pentan-2-ol, 1-({6-[(2-hydroxy-5-methylbenzyl)amino]-9-(methyl, ethyl, isopropyl, 3-pentyl, cyclohexyl, benzyl)-9H-purin-2-yl}amino)-2-methyl-propan-2-ol, 2-({6-[(2-hydroxy-3-methylbenzyl)amino]-9-(methyl, ethyl, isopropyl, 3-pentyl, cyclohexyl, benzyl)-9H-purin-2-yl}amino)butan-1-ol, $N^6$-(2-hydroxy-3-methylbenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-5-fluorobenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-3-methylbenzyl)-$N^2$-(4-aminocyclohexyl)-9-(methyl, ethyl, isopropyl, 3-pentyl, cyclohexyl, benzyl)-9H-purin-2,6-diamine, $N^6$-(2-hydroxy-3-methylbenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-3-methylbenzyl)amino]-9-(methyl, ethyl, isopropyl, 3-pentyl, cyclohexyl, benzyl)-9H-purin-2-yl}amino)-2-methyl-propan-2-ol, 1-({6-[(2-hydroxy-3-methylbenzyl)amino]-9-(methyl, ethyl, isopropyl, 3-pentyl, cyclohexyl, benzyl)-9H-purin-2-yl}amino)propan-2-ol, 3-({6-[(2-hydroxy-3-methylbenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-3-methylbenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-3-methylbenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-3-methylbenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-3-methylbenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-3-methylbenzyl)amino]-9-(methyl, ethyl, isopropyl, 3-pentyl, cyclohexyl, benzyl)-9H-purin-2-yl]amino}pentan-2-ol, 1-({6-[(2-hydroxy-3-methylbenzyl)amino]-9-(methyl, ethyl, isopropyl, 3-pentyl, cyclohexyl, benzyl)-9H-purin-2-yl}amino)-2-methyl-propan-2-ol, 2-({6-[(2-hydroxy-3-methoxybenzyl)amino]-9-(methyl, ethyl, isopropyl, 3-pentyl, cyclohexyl, benzyl)-9H-purin-2-yl}amino)butan-1-ol, $N^6$-(2-hydroxy-3-methoxybenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-3-methoxybenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-3-methoxybenzyl)-$N^2$-(4-aminocyclohexyl)-9-(methyl, ethyl, isopropyl, 3-pentyl, cyclohexyl, benzyl)-9H-purin-2,6-diamine, $N^6$-(2-hydroxy-3-methoxybenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-3-methoxybenzyl)amino]-9-(methyl, ethyl, isopropyl, 3-pentyl, cyclohexyl, benzyl)-9H-purin-2-yl}amino)-2-methyl-propan-2-ol, 1-({6-[(2-hydroxy-3-methoxybenzyl)amino]-9-(methyl, ethyl, isopropyl, 3-pentyl, cyclohexyl, benzyl)-9H-purin-2-yl}amino)propan-2-ol, 3-({6-([(2-hydroxy-3-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-3-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-3-methoxybenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-3-methoxybenzyl)amino]-9-(methyl, ethyl, isopropyl, 3-pentyl, cyclohexyl, benzyl)-9H-purin-2-yl}amino)-2,3-dimethyl-butan-2-ol, 4-({6-[(2-hydroxy-3-methoxybenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-3-methoxybenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-3-methoxybenzyl)amino]-9-(methyl, ethyl, isopropyl, 3-pentyl, cyclohexyl, benzyl)-9H-purin-2-yl]amino}pentan-2-ol, 1-({6-[(2-hydroxy-3-methoxybenzyl)amino]-9-(methyl, ethyl, isopropyl, 3-pentyl, cyclohexyl, benzyl)-9H-purin-2-yl}amino)-2-methyl-propan-2-ol, 1-({6-[(2-hydroxy-5-methoxybenzyl)amino]-9-(methyl, ethyl, isopropyl, 3-pentyl, cyclohexyl, benzyl)-9H-purin-2-yl}amino)propan-2-ol, 2-({6-[(2-hydroxy-5-methoxybenzyl)amino]-9-(methyl, ethyl, isopropyl, 3-pentyl, cyclohexyl, benzyl)-9H-purin-2-yl}amino)butan-1-ol, $N^6$-(2-hydroxy-5-methoxybenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-5-fluorobenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-5-methoxybenzyl)-$N^2$-(4-aminocyclohexyl)-9-(methyl, ethyl, isopropyl, 3-pentyl, cyclohexyl, benzyl)-9H-purin-2,6-diamine, $N^6$-(2-hydroxy-5-methoxybenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-5-methoxybenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-5-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-methoxybenzyl)amino]-9-(methyl, ethyl, isopropyl, 3-pentyl, cyclohexyl, benzyl)-9H-purin-2-yl}amino)-2-methyl-pentan-2-ol, 4-({6-[(2-hydroxy-5-methoxybenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-5-methoxybenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-5-methoxybenzyl)amino]-9-(methyl, ethyl, isopropyl, 3-pentyl, cyclohexyl, benzyl)-9H-purin-2-yl]amino}pentan-2-ol, 1-({6-[(2-hydroxy-5-methoxybenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-5-mercaptobenzyl)amino]-9-methyl-9H-purin-2-yl}amino)-2-methyl-pentan-2-ol, 3-({6-[(2-hydroxy-5-mercaptobenzyl)amino]-9-ethyl-9H-purin-2-yl}amino)-2-methyl-pentan-2-ol, 3-({6-[(2-hydroxy-5-mercaptobenzyl)amino]-9-isopropyl-9H-purin-2-yl}amino)-2-methyl-pentan-2-ol, 3-({6-[(2-hydroxy-5-mercaptobenzyl)amino]-9-cyclohexyl-9H-purin-2-yl}amino)-2-methyl-pentan-2-ol, 3-({6-[(2-hydroxy-5-mercaptobenzyl)amino]-9-benzyl-9H-purin-2-yl}amino)-2-methyl-pentan-2-ol, 3-({6-[(2-hydroxy-5-mercaptobenzyl)amino]-9-methyl-9H-purin-2-yl]amino}pentan-2-ol, 3-({6-[(2-hydroxy-5-mercaptobenzyl)amino]-9-ethyl-9H-purin-2-yl]amino}pentan-2-ol, 3-({6-[(2-hydroxy-5-mercaptobenzyl)amino]-9-isopropyl-9H-purin-2-yl]amino}pentan-2-ol, 3-({6-[(2-hydroxy-5-mercaptobenzyl)amino]-9-cyclohexyl-9H-purin-2-yl]amino}pentan-2-ol, 3-({6-[(2-hydroxy-5-mercaptobenzyl)amino]-9-benzyl-9H-purin-2-yl]amino}pentan-2-ol, 1-({6-[(2-hydroxy-5-mercaptobenzyl)amino]-9-cyclopropyl-9H-purin-2-yl}amino)-2-methyl-propan-2-ol, 1-({6-[(2-hydroxy-5-mercaptobenzyl)amino]-9-cyclohexyl-9H-purin-2-yl}amino)-2-methyl-propan-2-ol, 1-({6-[(2-hydroxy-5-mercaptobenzyl)amino]-9-benzyl-9H-purin-2-yl}amino)-2-methyl-propan-2-ol, 3-({6-[(2-hydroxy-5-nitrobenzyl)amino]-9-methyl-9H-purin-2-yl}amino)-2-methyl-pentan-2-ol, 3-({6-[(2-hydroxy-5-nitrobenzyl)amino]-9-ethyl-9H-purin-2-yl}amino)-2-methyl-pentan-2-ol, 3-({6-[(2-hydroxy-5-nitrobenzyl)amino]-9-isopropyl-9H-purin-2-yl}amino)-2-methyl-pentan-2-ol, 3-({6-[(2-hydroxy-5-nitrobenzyl)amino]-9-cyclohexyl-9H-purin-2-yl}amino)-2-methyl-pentan-2-ol, 3-({6-[(2-hydroxy-5-nitrobenzyl)amino]-9-benzyl-9H-purin-2-yl}amino)-2-methyl-pentan-2-ol, 3-({6-[(2-hydroxy-5-nitrobenzyl)amino]-9-methyl-9H-purin-2-yl]amino}pentan-2-ol, 3-({6-[(2-hydroxy-5-nitrobenzyl)amino]-9-ethyl-9H-purin-2-yl]amino}pentan-2-ol, 3-({6-[(2-hydroxy-5-nitrobenzyl)amino]-9-isopropyl-9H-purin-2-yl]amino}pentan-2-ol, 3-({6-[(2-hydroxy-5-nitrobenzyl)amino]-9-cyclohexyl-9H-purin-2-yl] amino}pentan-2-ol, 3-({6-[(2-hydroxy-5-nitrobenzyl) amino]-9-benzyl-9H-purin-2-yl]amino}pentan-2-ol, 1-({6-[(2-hydroxy-5-nitrobenzyl)amino]-9-cyclopropyl-9H-purin-2-yl}amino)-2-methyl-propan-2-ol, 1-({6-[(2-hydroxy-5-nitrobenzyl)amino]-9-cyclohexyl-9H-purin-2-yl}amino)-2-methyl-propan-2-ol, 1-({6-[(2-hydroxy-5-nitrobenzyl)amino]-9-benzyl-9H-purin-2-yl}amino)-2-methyl-propan-2-ol, 2-({6-[(2-hydroxy-5-aminobenzyl)amino]-9-(methyl, ethyl, isopropyl, 3-pentyl, cyclohexyl, benzyl)-9H-purin-2-yl}amino)butan-1-ol, $N^6$-(2-hydroxy-5-aminobenzyl)-$N^2$-(2-aminopropyl)-9-(methyl, ethyl, isopropyl, 3-pentyl, cyclohexyl, benzyl)-9H-purin-2,6-diamine, 2-({6-[(2-hydroxy-5-aminobenzyl)amino]-9-(methyl, ethyl, isopropyl, 3-pentyl, cyclohexyl, benzyl)-9H-purin-2-yl}amino)-3-methyl-butan-1-ol, $N^6$-(2-hydroxy-5-aminobenzyl)-$N^2$-(4-aminocyclohexyl)-9-(methyl, ethyl, isopropyl, 3-pentyl, cyclohexyl, benzyl)-9H-purin-2,6-diamine, 1-({6-[(2-hydroxy-5-aminobenzyl)amino]-9-(methyl, ethyl, isopropyl, 3-pentyl, cyclohexyl, benzyl)-9H-purin-2-yl}amino)-2-methyl-propan-2-ol, 3-({6-[(2-hydroxy-5-aminobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-aminobenzyl)amino]-9-(methyl, ethyl, isopropyl, 3-pentyl, cyclohexyl, benzyl)-9H-purin-2-yl}amino)-2-methyl-butan-2-ol, 4-({6-[(2-hydroxy-5-aminobenzyl)amino]-9-(methyl, ethyl, isopropyl, 3-pentyl, cyclohexyl, benzyl)-9H-purin-2-yl}amino)-2-methyl-pentan-2-ol, 1-({6-[(2-hydroxy-5-aminobenzyl)amino]-9-(methyl, ethyl, isopropyl, 3-pentyl, cyclohexyl, benzyl)-9H-purin-2-yl}amino)propan-2-ol, 4-({6-[(2-hydroxy-5-aminobenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2-hydroxy-5-aminobenzyl)amino]-9-(methyl, ethyl, isopropyl, 3-pentyl, cyclohexyl, benzyl)-9H-purin-2-yl}amino)-2-methyl-pentan-2-ol, 3-({6-[(2-hydroxy-5-aminobenzyl)amino]-9-(methyl, ethyl, isopropyl, 3-pentyl, cyclohexyl, benzyl)-9H-purin-2-yl]amino}pentan-2-ol, 1-({6-[(2-hydroxy-5-aminobenzyl)amino]-9-(methyl, ethyl, isopropyl, 3-pentyl, cyclohexyl, benzyl)-9H-purin-2-yl}amino)-2-methyl-propan-2-ol, 2-({6-[(2,3-dihydroxy-4-methoxybenzyl)amino]-9-(methyl, ethyl, isopropyl, 3-pentyl, cyclohexyl, benzyl)-9H-purin-2-yl}amino)butan-1-ol, $N^6$-(2,3-dihydroxy-4-methoxybenzyl)-$N^2$-(2-aminopropyl)-9-(methyl, ethyl, isopropyl, 3-pentyl, cyclohexyl, benzyl)-9H-purin-2,6-diamine, 2-({6-[(2,3-dihydroxy-4-methoxybenzyl)amino]-9-(methyl, ethyl, isopropyl, 3-pentyl, cyclohexyl, benzyl)-9H-purin-2-yl}amino)-3-methyl-butan-1-ol, $N^6$-(2,3-dihydroxy-4-methoxybenzyl)-$N^2$-(4-aminocyclohexyl)-9-(methyl, ethyl, isopropyl, 3-pentyl, cyclohexyl, benzyl)-9H-purin-2,6-diamine, 1-({6-([(2,3-dihydroxy-4-methoxybenzyl)amino]-9-(methyl, ethyl, isopropyl, 3-pentyl, cyclohexyl, benzyl)-9H-purin-2-yl}amino)-2-methyl-propan-2-ol, 3-({6-([2,3-dihydroxy-4-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2,3-dihydroxy-4-methoxybenzyl)amino]-9-(methyl, ethyl, isopropyl, 3-pentyl, cyclohexyl, benzyl)-9H-purin-2-yl}amino)-2-methyl-butan-2-ol, 4-({6-([2,3-dihydroxy-4-methoxybenzyl)amino]-9-(methyl, ethyl, isopropyl, 3-pentyl, cyclohexyl, benzyl)-9H-purin-2-yl}amino)-2-methyl-pentan-2-ol, 1-({6-[(2,3-dihydroxy-4-methoxybenzyl)amino]-9-(methyl, ethyl, isopropyl, 3-pentyl, cyclohexyl, benzyl)-9H-purin-2-yl}amino)propan-2-ol, 4-({6-[(2,3-dihydroxy-4-methoxybenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2,3-dihydroxy-4-methoxybenzyl)amino]-9-(methyl, ethyl, isopropyl, 3-pentyl, cyclohexyl, benzyl)-9H-purin-2-yl}amino)-2-methyl-pentan-2-ol, 3-({6-[(2,3-dihydroxy-4-methoxybenzyl)amino]-9-(methyl, ethyl, isopropyl, 3-pentyl, cyclohexyl, benzyl)-9H-purin-2-yl]amino}pentan-2-ol, 1-({6-[(2,3-dihydroxy-4-methoxybenzyl)amino]-9-(methyl, ethyl, isopropyl, 3-pentyl, cyclohexyl, benzyl)-9H-purin-2-yl}amino)-2-methyl-propan-2-ol, 2-({6-[(2,5-dihydroxy-4-methoxybenzyl)amino]-9-(methyl, ethyl, isopropyl, 3-pentyl, cyclohexyl, benzyl)-9H-purin-2-yl}amino)butan-1-ol, $N^6$-(2,5-dihydroxy-4-methoxybenzyl)-$N^2$-(2-aminopropyl)-9-(methyl, ethyl, isopropyl, 3-pentyl, cyclohexyl, benzyl)-9H-purin-2,6-diamine, 2-({6-[(2,5-dihydroxy-4-methoxybenzyl)amino]-9-(methyl, ethyl, isopropyl, 3-pentyl, cyclohexyl, benzyl)-9H-purin-2-yl}amino)-3-methyl-butan-1-ol, $N^6$-(2,5-dihydroxy-4-methoxybenzyl)-$N^2$-(4-aminocyclohexyl)-9-(methyl, ethyl, isopropyl, 3-pentyl, cyclohexyl, benzyl)-9H-purin-2,6-diamine, 1-({6-[(2,5-dihydroxy-4-methoxybenzyl)amino]-9-(methyl, ethyl, isopropyl, 3-pentyl, cyclohexyl, benzyl)-9H-purin-2-yl}amino)-2-methyl-propan-2-ol, 3-({6-[(2,5-dihydroxy-4-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2,5-dihydroxy-4-methoxybenzyl)amino]-9-(methyl, ethyl, isopropyl, 3-pentyl, cyclohexyl, benzyl)-9H-purin-2-yl}amino)-2-methyl-butan-2-ol, 4-({6-[(2,5-dihydroxy-4-methoxybenzyl)amino]-9-(methyl, ethyl, isopropyl, 3-pentyl, cyclohexyl, benzyl)-9H-purin-2-yl}amino)-2-methyl-pentan-2-ol, 1-({6-[(2,5-dihydroxy-4-methoxybenzyl)amino]-9-(methyl, ethyl, isopropyl, 3-pentyl, cyclohexyl, benzyl)-9H-purin-2-yl}amino)propan-2-ol, 4-({6-[(2,5-dihydroxy-4-methoxybenzyl)amino]-9-(methyl, ethyl, isopropyl, 3-pentyl, cyclohexyl, benzyl)-9H-purin-2-yl}amino)-2,3-dimethyl-butan-2-ol, 3-({6-[(2,5-dihydroxy-4-methoxybenzyl)amino]-9-(methyl, ethyl, isopropyl, 3-pentyl, cyclohexyl, benzyl)-9H-purin-2-yl}amino)-2-methyl-pentan-2-ol, 3-({6-[(2,5-dihydroxy-4-methoxybenzyl)amino]-9-(methyl, ethyl, isopropyl, 3-pentyl, cyclohexyl, benzyl)-9H-purin-2-yl]amino}pentan-2-ol, 1-({6-[(2,5-dihydroxy-4-chlorobenzyl)amino]-9-(methyl, ethyl, isopropyl, 3-pentyl, cyclohexyl, benzyl)-9H-purin-2-yl}amino)-2-methyl-propan-2-ol, 2-({6-[(2,5-dihydroxy-4-chlorobenzyl)amino]-9-(methyl, ethyl, isopropyl, 3-pentyl, cyclohexyl, benzyl)-9H-purin-2-yl}amino)butan-1-ol, $N^6$-(2,5-dihydroxy-4-chlorobenzyl)-$N^2$-(2-aminopropyl)-9-(methyl, ethyl, isopropyl, 3-pentyl, cyclohexyl, benzyl)-9H-purin-2,6-diamine, 2-({6-[(2,5-dihydroxy-4-chlorobenzyl)amino]-9-(methyl, ethyl, isopropyl, 3-pentyl, cyclohexyl, benzyl)-9H-purin-2-yl}amino)-3-methyl-butan-1-ol, 1-({6-[(2,5-dihydroxy-4-chlorobenzyl)amino]-9-(methyl, ethyl, isopropyl, 3-pentyl, cyclohexyl, benzyl)-9H-purin-2-yl}amino)-2-methyl-propan-2-ol.

Pharmaceutical Compositions

The therapeutic composition comprise about 1% to about 95% of the active ingredient, single-dose forms of administration preferably comprising about 20% to about 90% of the active ingredient and administration forms, which are not single-dose preferably comprising about 5% to about 20% of the active ingredient. Unit dose forms may be, for example, coated tablets, tablets, ampoules, vials, suppositories or capsules. Other forms of administration are, for example, ointments, creams, pastes, foams, tinctures, lipsticks, drops, sprays, dispersions and the like. Examples are capsules containing from about 0.05 g to about 1.0 g of the active ingredient.

The pharmaceutical compositions of the present invention are prepared in a manner known per se, for example by means of conventional mixing, granulating, coating, dissolving or lyophilizing processes.

Preferably, solutions of the active ingredient, and in addition also suspensions or dispersions, especially isotonic aqueous solutions, dispersions or suspensions, are used, if being possible for these to be prepared before use, for example in the case of lyophilised compositions which comprise the active substance by itself or together with a carrier, for example mannitol. The pharmaceutical compositions can be sterilised and/or comprise excipients, for example preservatives, stabilisers, wetting agents and/or emulsifiers, solubilizing agents, salts for regulating the osmotic pressure and/or buffers, and they are prepared in a manner known per se, for example by means of conventional dissolving or lyophilising processes. The solutions or suspensions mentioned can comprise viscosity-increasing substances, such as sodium carboxymethylcellulose, dextran, polyvinylpyrrolidone or gelatine. Suspensions in oil comprise, as the oily component, the vegetable, synthetic or semi-synthetic oils customary for injection purposes. Oils which may be mentioned are, in particular, liquid fatty acid esters which contain, as the acid component, a long-chain fatty acid having 8-22, in particular 12-22, carbon atoms, for example lauric acid, tridecylic acid, myristic acid, pentadecylic acid, palmitic acid, margaric acid, stearic acid, arachidonic acid, behenic acid or corresponding unsaturated acids, for example oleic acid, elaidic acid, euric acid, brasidic acid or linoleic acid, if appropriate with the addition of antioxidants, for example vitamin E, β-carotene or 3,5-di-tert-butyl-4-hydroxytoluene. The alcohol component of these fatty acid esters has not more than 6 carbon atoms and is mono- or polyhydric, for example mono-, di- or trihydric alcohol, for example methanol, ethanol, propanol, butanol, or pentanol, or isomers thereof, but in particular glycol and glycerol. Fatty acid esters are, for example: ethyl oleate, isopropyl myristate, isopropyl palmitate, "Labrafil M 2375" (polyoxyethylene glycerol trioleate from Gattefoseé, Paris), "Labrafil M 1944 CS" (unsaturated polyglycolated glycerides prepared by an alcoholysis of apricot kernel oil and made up of glycerides and polyethylene glycol esters; from Gattefoseé, Paris), "Labrasol" (saturated polyglycolated glycerides prepared by an alcoholysis of TCM and made up of glycerides and polyethylene glycol esters; from Gattefoseé, Paris) and/or "Miglyol 812" (triglyceride of saturated fatty acids of chain length $C_8$ to $C_{12}$ from Hüls AG, Germany), and in particular vegetable oils, such as cottonseed oil, almond oil, olive oil, castor oil, sesame oil, soybean oil and, in particular, groundnut oil.

The preparation of the injection compositions is carried out in the customary manner under sterile conditions, as are bottling, for example into ampoules or vials, and closing of the containers.

For example, pharmaceutical compositions for oral use can be obtained by combining the active ingredient with one or more solid carriers, if appropriate granulating the resulting mixture, and, if desired, processing the mixture or granules to tablets or coated tablet cores, if appropriate by addition of additional excipients.

Suitable carriers are, in particular, fillers, such as sugars, for example lactose, sucrose, mannitol or sorbitol, cellulose preparations and/or calcium phosphates, for example tricalcium diphosphate, or calcium hydrogen phosphate, and furthermore binders, such as starches, for example maize, wheat, rice or potato starch, methylcellulose, hydroxypropylmethylcellulose, sodium carboxymethylcellulose and/or polyvinylpyrrolidine, and/or, if desired, desintegrators, such as the above mentioned starches, and furthermore carboxymethylstarch, cross-linked polyvinylpyrrolidone, alginic acid or a salt thereof, such as sodium alginate. Additional excipients are, in particular, flow regulators and lubricants, for example salicylic acid, talc, stearic acid or salts thereof, such as magnesium stearate or calcium stearate, and/or polyethylene glycol, or derivatives thereof.

Coated tablet cores can be provided with suitable coatings which, if appropriate, are resistant to gastric juice, the coatings used being, inter alia, concentrated sugar solutions, which, if appropriate, comprise gum arabic, talc, polyvinylpyrrolidine, polyethylene glycol and/or titanium dioxide, coating solutions in suitable organic solvents or solvent mixtures or, for the preparation of coatings which are resistant to gastric juice, solutions of suitable cellulose preparations, such as acetylcellulose phthalate or hydroxypropylmethylcellulose phthalate. Dyes or pigments can be admixed to the tablets or coated tablet coatings, for example for identification or characterisation of different doses of active ingredient.

Pharmaceutical compositions, which can be used orally, are also hard capsules of gelatine and soft, closed capsules of gelatine and a plasticiser, such as glycerol or sorbitol. The hard capsules can contain the active ingredient in the form of granules, mixed for example with fillers, such as maize starch, binders and/or lubricants, such as talc or magnesium stearate, and stabilisers if appropriate. In soft capsules, the active ingredient is preferably dissolved or suspended in suitable liquid excipients, such as greasy oils, paraffin oil or liquid polyethylene glycol or fatty acid esters of ethylene glycol or propylene glycol, it being likewise possible to add stabilisers and detergents, for example of the polyethylene sorbitan fatty acid ester type.

Other oral forms of administration are, for example, syrups prepared in the customary manner, which comprise the active ingredient, for example, in suspended form and in a concentration of about 5% to 20%, preferably about 10% or in a similar concentration which results in a suitable individual dose, for example, when 5 or 10 ml are measured out. Other forms are, for example, also pulverulent or liquid concentrates for preparing of shakes, for example in milk. Such concentrates can also be packed in unit dose quantities.

Pharmaceutical compositions, which can be used rectally, are, for example, suppositories that comprise a combination of the active ingredient with a suppository base. Suitable suppository bases are, for example, naturally occurring or synthetic triglycerides, paraffin hydrocarbons, polyethylene glycols or higher alkanols.

Compositions which are suitable for parental administration are aqueous solutions of an active ingredient in water-soluble form, for example of water-soluble salt, or aqueous injection suspensions, which comprise viscosity-increasing substances, for example sodium carboxymethylcellulose, sorbitol and/or dextran, and, if appropriate, stabilizers. The active ingredient can also be present here in the form of a lyophilisate, if appropriate, together with excipients, and be dissolved before parenteral administration by addition of suitable solvents. Solutions such as are used, for example, for parental administration can also be used as infusion solutions. Preferred preservatives are, for example, antioxidants, such as ascorbic acid, or microbicides, such as sorbic or benzoic acid.

Ointments are oil-in-water emulsions which comprise not more than 70%, preferably 20-50% of water or aqueous phase. The fatty phase consists, in particular, hydrocarbons, for example vaseline, paraffin oil or hard paraffins, which preferably comprise suitable hydroxy compounds, such as fatty alcohols or esters thereof, for example cetyl alcohol, or wool wax alcohols, such as wool wax, to improve the water-binding capacity. Emulsifiers are corresponding lipophilic substances, such as sorbitan fatty acid esters (Spans), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and odoriferous substances.

Tinctures and solutions usually comprise an aqueous-ethanolic base to which, humectants for reducing evaporation, such as polyalcohols, for example glycerol, glycols and/or polyethylene glycol, and re-oiling substances, such as fatty acid esters with lower polyethylene glycols, i.e. lipophilic substances soluble in the aqueous mixture to substitute the fatty substances removed from the skin with ethanol, and, if necessary, other excipients and additives, are admixed.

The invention also relates to a process or method for treatment of the disease states mentioned above. The compounds can be administered prophylactically or therapeutically as such or in the form of pharmaceutical compositions, preferably in an amount, which is effective against the diseases mentioned. With a warm-blooded animal, for example a human, requiring such treatment, the compounds are used, in particular, in the form of pharmaceutical composition. A daily dose of about 0.1 to about 5 g, preferably 0.5 g to about 2 g, of a compound of the present invention is administered here for a body weight of about 70 kg.

EXAMPLES OF CARRYING OUT THE INVENTION

Figure 1:
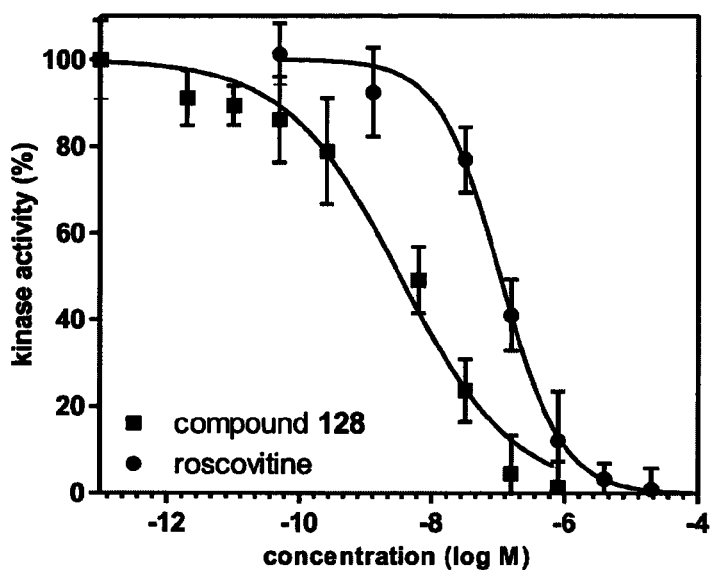
FIG. 1 shows inhibition of the CDK2/cyclin E kinase activity by purine derivative 128 and roscovitine.

The following examples serve to illustrate the invention without limiting the scope thereof.

The starting material for the compounds of the formula I is available from commercial sources (Sigma-Aldrich, Fluka, etc.). Melting points were determined on a Koffler block and are uncorrected. Evaporations were carried out on a rotary evaporator under vacuum at temperatures below 80° C. The $^1$H NMR spectra (σ, ppm; J, Hz) were measured on Varian VXR-400 (400 MHz) or on Varian Unity 300 (300 MHz) instruments. All spectra were obtained at 25° C. using tetramethylsilane as an internal standard. Electron impact mass spectra m/z (rel. %, composition, deviation) were measured on a VG 7070E spectrometer (70 eV, 200° C., direct inlet). Quadrupole mass spectra were measured on a Micromass ZMD detector with electrospray ionization. Merck silica gel Kieselgel 60 (230-400 mesh) was used for column chromatography. All compounds gave satisfactory elemental analyses (±0,4%).

The starting 9-hydrocarbyl-2,6-dichloropurines were prepared according to the procedures described in the literature:

2,6-dichloro-9-methylpurine

1) Parker et al. Phytochemistry 25, 1986: 303-310
2) Brik et al. Bioorg. Med. Chem. 13, 2005: 4622-4626;

2,6-dichloro-9-ethylpurine

Pitts et al. Bioorg. Med. Chem. Let. 14, 2004: 2955-2958

2,6-dichloro-9-isopropylpurine

1) Rypka et al. Xenobiotica 32, 2002: 1017-1032
2) Lu et al. J. Org. Chem. 72, 2007: 5012-5015

2,6-dichloro-9-benzylpurine

1) Kelley et al. J. Med. Chem. 31; 1988: 2001-2004
2) Naito et al. Chem. Pharm. Bul. 30, 1982: 2011-2019
3) Dalby et al. Angew. Chem. German 105, 1993: 1822-1823
4) Brik et al. Bioorg. Med. Chem. 13, 2005; 4622-4626
5) Weterings et al. Bioorg. Med. Chem. Let. 16, 2006: 3258-3261
6) Toyota et al. Synth. Commun. 23, 1993: 1295-1305
7) Gundersen et al. Tetrahedron Let. 36, 1995: 1945-1948
8) Lu et al. J. Organ. Chem. 72, 2007: 5012-5015

2,6-dichloro-9-cyclopropylpurine 2,6-Dichloropurine (1 mmol), triphenylphosphine (1.3 mmol), tetrahydrofurane (5 ml) and cyclopropanol (5 mmol) were stirred at rt under nitrogen to give clear yellowish solution, which was then cooled to 0° C. and diisopropyldiazadicarboxylate (DIAD; 1.3 mmol) was added via syringe. The reaction mixture was then stirred at rt for 12 h. After evaporation of the solvents the product was extracted with diethylether and purified by column chromatography (silicagel, 1% MeOH in CHCl$_3$). Crystallization from methanol gave the product in yield 35%, mp 121-124° C.

2,6-dichloro-9-cyclopentylpurine

1) Shum et al. Nucleos. Nucleot. 20, 2001: 1067-1078
2) Drezer et al. J. Med. Chem. 44, 2001: 524-530

2,6-dichloro-9-cyclohexylpurine 2,6-Dichloropurine (1 mmol), powdered potassium carbonate (1 mmol) and cyclohexyliodide (4 mmol) were vigorously stirred in 5 mL DMSO overnight. After evaporation of the solvent the product was extracted (water/diethylether) and purified by column chromatography (silicagel/1% MeOH in CHCl$_3$). Crystallization from methanol gave the product in yield 41%, mp 116-121° C.

Example 1

General method for the preparation of 2-chloro-6-[(2-hydroxy-R$_n$-benzyl)amino]-9-hydrocarbyl-purine precursor 2,6-dichloro-9-hydrocarbylpurine (2 mmol), 2-hydroxy-R$_n$-benzylamine (2.5 mmol) and triethylamine (0.4 mL) were heated in 5 mL of 1-butanol (110° C., 1.5 h). The product was crystallized from reaction mixture during heating or after cooling in refrigerator. The product was filtered and washed with 1-butanol.

6-[(2-hydroxy-3-methoxybenzyl)amino]-2-chloro-9-methylpurine

Yield 91%; mp 202-205° C.
$^1$H NMR (CDCl$_3$): 3.14 (3H, s), 3.28 (3H, s), 4.79 (2H, s(br)), 6.49 (1H, d, J=7.5), 6.65-6.72 (2H, m), 7.86 (1H, s), 8.25 (1H, s(br)), 10.15 (1H, s(br))

6-[(2-hydroxy-3-methoxybenzyl)amino]-2-chloro-9-ethylpurine

Yield 90%; mp 195-198° C.;
$^1$H NMR (CDCl$_3$): 1.24 (3H, t, J=6.0), 3.23 (2H, q, J=6.0), 3.65 (3H, s), 4.80 (2H, s(br)), 6.49 (1H, d, J=7.5), 6.65-6.72 (2H, m), 7.95 (1H, s), 8.05 (1H, s(br)), 10.40 (1H, s(br))

6-[(2-hydroxy-3-methoxybenzyl)amino]-2-chloro-9-isopropylpurine

Yield 93%; mp 190-192° C.
$^1$H NMR (CDCl$_3$): 1.38 (6H, d, J=6.0), 3.25 (1H, sept, J=6.0), 3.62 (3H, s), 4.75 (2H, s(br)), 6.49 (1H, d, J=7.5), 6.65-6.72 (2H, m), 8.05 (1H, s), 8.25 (1H, s(br)), 10.25 (1H, s(br))

6-[(2-hydroxy-3-methoxybenzyl)amino]-2-chloro-9-cyclopropylpurine

Yield 88%; mp 217-220° C.
$^1$H NMR (CDCl$_3$): 0.63 (2H, q, J=4.5), 0.69 (2H, q, J=4.5), 3.59 (1H, m), 3.65 (3H, s), 4.80 (2H, s(br)), 6.49 (1H, d, J=7.5), 6.65-6.72 (2H, m), 7.94 (1H, s), 8.25 (1H, s(br)), 10.25 (1H, s(br))

6-[(2-hydroxy-3-methoxybenzyl)amino]-2-chloro-9-cyclopentylpurine

Yield 89%; mp 174-176° C.
$^1$H NMR (CDCl$_3$): 1.38-1.67 (4H, m), 1.74-1.82 (4H, m), 2.03 (1H, qui, J7.5), 3.62 (3H, s), 4.75 (2H, s(br)), 6.49 (1H, d, J=7.5), 6.65-6.72 (2H, m), 8.05 (1H, s), 8.25 (1H, s(br)), 10.25 (1H, s(br)) 176° C.;

6-[(2-hydroxy-3-methoxybenzyl)amino]-2-chloro-9-cyclohexylpurine

Yield 89%; mp 169-172° C.
$^1$H NMR (CDCl$_3$): 1.33-1.42 (4H, m), 1.53-1.58 (1H, m), 1.70-1.80 (4H, m), 1.92-1.99 (1H, m), 3.62 (3H, s), 4.62 (2H, s(br)), 4.96 (1H, qui, J=5.7), 6.49 (1H, d, J=7.5), 6.65-6.72 (2H, m), 8.05 (1H, s), 8.25 (1H, s(br)), 10.25 (1H, s(br))

6-[(2-hydroxy-3-methoxybenzyl)amino]-2-chloro-9-benzylpurine

Yield 94%; mp 208-211° C.
$^1$H NMR (CDCl$_3$): 3.63 (3H, s), 4.43 (2H, s), 4.63 (2H, s(br)), 6.45 (1H, d, J=7.5), 6.65-6.80 (2H, m), 7.14 (1H, t, J=7.50), 7.26 (2H, t, J=7.5), 7.39 (2H, d, J=7.5), 7.89 (1H, s), 8.25 (1H, s(br)), 10.25 (1H, s(br))

Example 2

General method for the preparation of (substituted) 2-hydrocarbylamino-6-[(2-hydroxy-R$_n$-benzyl)amino]9-alkyl purines 2-Chloro-6-[(2-hydroxy-R$_n$-benzyl)amino]-9-hydrocarbylpurine (1 mmol), the appropriate amine (3 mmol) and diisopropylethylamine (2 mmol) were heated (the temperature and incubation period is specified for each below mentioned substance) in N-methylpyrrolidone (5 mL, sealed ampule). The reaction mixture was then partitioned between water and CHCl$_3$. Column chromatography (silicagel, chloroform/methanol) afforded pure product.

(R)-1-({6-[(2-hydroxy-3-methoxybenzyl)amino]-9-isopropyl-9H-purin-2-yl}amino)propan-2-ol Reaction conditions: 160° C., 3 h. Liquid chromatography 1.5% MeOH in CHCl$_3$; crystallization from abs. CHCl$_3$; mp 100-103° C.
$^1$H NMR (CDCl$_3$): 0.86 (3H, t, J=9.0), 1.46 (6H, dd, J=12.0, J'=3.0), 1.63 (1H, sep, J=12.0), 2.54 (1H, s), 3.38-3.56 (2H, m), 3.76 (3H, s), 3.82 (1H, m), 4.58 (2H, qui, J=9.0), 4.62 (2H, s(br)), 5.85 (1H, d, J=15.0), 6.67 (1H, t, J=12.0), 6.76-6.87 (2H, m), 7.50 (1H, s(br)), 7.78 (1H, s), 9.32 (1H, s(br)).
$^{13}$C NMR (CDCl$_3$): 10.56, 21.95, 23.82, 54.01, 55.75, 62.92, 64.83, 110.73, 113.55, 118.43, 120.65, 126.78, 135.21, 144.01, 147.57, 150.55, 154.42, 158.74

(S)-1-({6-[(2-hydroxy-3-methoxybenzyl)amino]-9-isopropyl-9H-purin-2-yl}amino)propan-2-ol Reaction conditions: 160° C., 3 h. Liquid chromatography 1.5% MeOH in CHCl$_3$; crystallization from abs. CHCl$_3$; mp 100-102° C.
$^1$H NMR (CDCl$_3$): 0.86 (3H, t, J=9.0), 1.46 (6H, dd, J=12.0, J'=3.0), 1.63 (1H, sep, J=12.0), 2.54 (1H, s), 3.38-3.56 (2H, m), 3.76 (3H, s), 3.82 (1H, m), 4.58 (2H, qui, J=9.0), 4.62 (2H, s(br)), 5.85 (1H, d, J=15.0), 6.67 (1H, t, J=12.0), 6.76-6.87 (2H, m 7.50 (1H, s(br)), 7.78 (1H, s), 9.32 (1H, s(br)).
$^{13}$C NMR (CDCl$_3$): 10.56, 21.95, 23.82, 54.01, 55.75, 62.92, 64.83, 110.73, 113.55, 118.43, 120.65, 126.78, 135.21, 144.01, 147.57, 150.55, 154.42, 158.74

(RS)-2-({6-[(2-hydroxy-3-methoxybenzyl)amino]-9-isopropyl-9-H-purin-2-yl}amino)butan-1-ol Reaction conditions: 160° C., 6 h. Liquid chromatography 1.5% MeOH in CHCl$_3$; crystallization from abs. CHCl$_3$/abs. Et$_2$O; mp 120-122° C.
$^1$H NMR (CDCl$_3$): 0.86 (3H, t, J=9.0), 1.46 (6H, dd, J=12.0, J'=3.0), 1.63 (1H, sep, J=12.0), 2.54 (1H, s), 3.38-3.56 (2H, m), 3.76 (3H, s), 3.82 (1H, m), 4.58 (2H, qui, J=9.0), 4.62 (2H, s(br)), 5.85 (1H, d, J=15.0), 6.67 (1H, t, J=12.0), 6.76-6.87 (2H, m), 7.50 (1H, s(br)), 7.78 (1H, s), 9.32 (1H, s(br)).
$^{13}$C NMR (CDCl$_3$): 10.56, 21.95, 23.82, 54.01, 55.75, 62.92, 64.83, 110.73, 113.55, 118.43, 120.65, 126.78, 135.21, 144.01, 147.57, 150.55, 154.42, 158.74

(R)-1-({6-[(2-hydroxy-4-methoxybenzyl)amino]-9-isopropyl-9H-purin-2-yl}amino)propan-2-ol Reaction conditions: 160° C., 3 h. Liquid chromatography 1.5% MeOH in CHCl$_3$; crystallization from abs. CHCl$_3$; mp 106-108° C.
$^1$H NMR (CDCl$_3$): 0.88 (3H, t, J=9.0), 1.45 (6H, dd, J=12.0, J'=3.0), 1.66 (1H, sep, J=12.0), 3.38-3.56 (2H, m), 3.64 (3H, s), 3.82 (1H, m, J=9.0), 4.57 (2H, qui, J=9.0), 4.64 (2H, s(br)), 5.80 (1H, d, J=15.0), 6.34 (1H, s), 6.41 (1H, d, J=7.5), 6.92 (1H, d, J=7.5), 7.50 (1H, s(br)), 7.79 (1H, s), 8.95 (1H, s(br)).
$^1$H NMR (CDCl$_3$): 10.9, 22.5, 25.0, 42.6, 46.4, 55.6, 56.3, 68.5, 100.7, 103.9, 114.7, 120.0, 130.3, 134.6, 152.0, 155.8, 158.9, 160.0

(R)-1-({6-[(2,3-dihydroxybenzyl)amino]-9-isopropyl-9H-purin-2-yl}amino)propan-2-ol Reaction conditions: 155° C., 2 h. Liquid chromatography 1.5% MeOH in CHCl$_3$; crystallization from abs. diethylether; mp 182-183° C.
$^1$H NMR (CDCl$_3$): 0.86 (3H, t, J=9.0), 1.46 (6H, dd, J=12.0, J'=3.0), 1.63 (1H, sep, J=12.0), 3.38-3.56 (2H, m), 3.82 (1H, m, J=9.0), 4.57 (2H, qui, J=9.0), 4.64 (2H, s(br)), 5.80 (1H, d, J=15.0), 6.55 (1H, t, J=11.0), 6.62-6.70 (2H, m), 7.50 (1H, s(br)), 7.79 (1H, s), 8.95 (1H, s(br)), 9.40 (1H, s(br)).
$^1$H NMR (CDCl$_3$): 10.55, 21.84, 21.93, 23.78, 45.75, 53.97, 62.84, 114.08, 118.59, 119.31, 126.92, 135.27, 142.93, 145.30, 154.28, 158.61

(R)-1-({6-[(2,4-dihydroxybenzyl)amino]-9-isopropyl-9H-purin-2-yl}amino)propan-2-ol Reaction conditions: 155° C., 2 h. Liquid chromatography 1.5% MeOH in CHCl$_3$; crystallization from abs. diethylether; mp 189-191° C.
$^1$H NMR (CDCl$_3$): 0.90 (3H, t, J=9.0), 1.43 (6H, dd, J=12.0, J'=3.0), 1.82 (1H, sep, J=12.0), 3.38-3.56 (2H, mt), 3.78 (1H, m, J=9.0), 4.59 (2H, qui, J=9.0), 4.58 (2H, s(br)), 5.80 (1H, d, J=15.0), 6.28 (1H, s), 6.32 (1H, d, J=7.5), 6.85 (1H, d, J=7.5), 7.52 (1H, s(br)), 7.79 (1H, s), 8.95 (1H, s(br)), 10.50 (1H, s(br)).

¹H NMR (CDCl₃): 10.9, 22.5, 25.0, 42.6, 46.4, 56.3, 68.5, 102.6, 108.2, 114.7, 118.3, 130.5, 134.6, 152.0, 155.7, 155.8, 158.4, 160.0

(R)-1-({6-[(2,5-dihydroxybenzyl)amino]-9-isopropyl-9H-purin-2-yl}amino)propan-2-ol Reaction conditions: 155° C., 2 h. Liquid chromatography 1.5% MeOH in CHCl₃; crystallization from abs. diethylether; mp 162.4-163.6° C.

¹H NMR (CDCl₃): 0.86 (3H, t, J=9.0), 1.45 (6H, dd, J=12.0, J'=0.8), 1.82 (1H, sep, J=12.0), 3.38-3.56 (2H, mt), 3.76 (1H, m, J=9.0), 4.59 (2H, qui, J=9.0), 4.58 (2H, s(br)), 5.80 (1H, d, J=15.0), 6.28 (1H, s), 6.32 (1H, d, J=7.5), 6.85 (1H, d, J=7.5), 7.52 (1H, s(br)), 7.79 (1H, s), 8.95 (1H, s(br)), 10.50 (1H, s(br)).

¹H NMR (CDCl₃): 10.9, 22.5, 25.0, 39.4, 46.4, 56.3, 68.5, 114.7, 116.0, 116.9, 117.2, 127.8, 134.6, 149.5, 151.3, 152.0, 155.8, 160.0

(R)-1-({6-[(2-hydroxy-3-methylbenzyl)amino]-9-isopropyl-9H-purin-2-yl}amino)propan-2-ol Reaction conditions: 160° C., 3 h. Liquid chromatography 1.5% MeOH in CHCl₃; crystallization from abs. diethylether; mp 145-147° C.

¹H NMR (CDCl₃): 0.89 (3H, t, J=9.0), 1.46 (6H, dd, J=12.0, J'=3.0), 1.63 (1H, sep, J=12.0), 2.32 (3H, s), 2.54 (1H, s), 3.38-3.56 (2H, m), 3.76 (3H, s), 3.82 (1H, m), 4.58 (2H, qui, J=9.0), 4.62 (2H, s(br)), 6.76-6.83 (3H, m), 7.50 (1H, s(br)), 7.78 (1H, s), 9.32 (1H, s(br)).

¹H NMR (CDCl₃): 10.9, 16.6, 22.5, 25.0, 38.3, 46.4, 56.3, 68.5, 114.7, 119.2, 125.1, 125.8, 126.4, 129.4, 134.6, 152.0, 154.1, 155.8

(R)-1-({6-[(2-hydroxy-5-methylbenzyl)amino]-9-isopropyl-9H-purin-2-yl}amino)propan-2-ol Reaction conditions: 160° C., 3 h. Liquid chromatography 1.5% MeOH in CHCl₃; crystallization from abs. diethylether; mp 160.0-161.3° C.

¹H NMR (CDCl₃): 0.89 (3H, t, J=9.0), 1.46 (6H, dd, J=12.0, J'=3.0), 1.63 (1H, sep, J=12.0), 2.32 (3H, s), 2.54 (1H, s), 3.38-3.56 (2H, m), 3.76 (3H, s), 3.82 (1H, m), 4.58 (2H, qui, J=9.0), 4.62 (2H, s(br)), 6.72 (1H, d, J=7.50), 6.77-6.80 (2H, m), 7.50 (1H, s(br)), 7.78 (1H, s), 9.50 (1H, s(br)).

¹H NMR (CDCl₃): 10.9, 20.5, 22.5, 25.0, 39.4, 46.4, 56.3, 68.5, 114.7, 118.3, 124.1, 127.4, 129.1, 133.2, 134.6, 152.0, 152.3, 155.8, 160.0

(E/Z)—$N^2$-(4-aminocyclohexyl)-$N^6$-(2-hydroxy-3-methoxybenzyl)-9-isopropyl-9H-purine-2,6-diamine Reaction conditions: 160° C., 4 h. Liquid chromatography stepwise 1, 2, 3, 4, 5% MeOH in CHCl₃ with a trace o concentrated NH₄OH.; mp 136.2-137.5° C.

¹H NMR (CDCl₃): 1.42 (6H, d, J=6.0), 1.57-1.62 (4H, m), 1.65 (1H, sep, J=6.0), 1.82-1.87 (4H, m), 2.25 (2H, s(br)), 3.71 (3H, s), 4.68 (2H, s(br)), 6.54 (1H, d, J=7.5), 6.69 (1H, d, J=7.5), 6.84 (1H, t, J=7.5), 7.50 (1H, s(br)), 7.72 (1H, s), 10.2 (1H, s(br)).

¹H NMR (CDCl₃): 22.5, 30.8, 33.6, 38.3, 46.4, 48.9, 55.9, 109.5, 114.7, 119.0, 123.1, 127.0, 134.6, 146.6, 148.9, 152.0, 153.2, 155.8

Purine Structure with Substituents as Designated in the Following Tables:

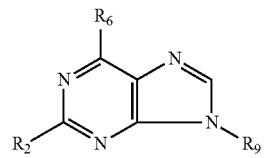

TABLE 1

Compounds Prepared by the Method of Example 2

| No | R2 | R6 | R9 | CHN ANALYSES [%] | MS (ZMD)-ANALYSES [M − H]⁻ a) | [M + H]⁺ b) |
|---|---|---|---|---|---|---|
| 1 | 2-aminocyclohexylamino | (2-hydroxy-5-chlorobenzyl)amino | methyl | 56.8/6.0/24.4 | 400.9 | 402.9 |
| 2 | 4-aminocyclohexylamino | (2-hydroxy-5-chlorobenzyl)amino | methyl | 56.8/6.0/24.4 | 400.9 | 402.9 |
| 3 | (1-hydroxymethyl)propylamino | (2-hydroxy-5-chlorobenzyl)amino | methyl | 54.2/5.6/22.3 | 375.8 | 377.8 |
| 4 | (1-hydroxymethyl-2-methyl)propylamino | (2-hydroxy-5-chlorobenzyl)amino | methyl | 55.3/5.9/21.5 | 389.9 | 391.9 |
| 5 | 4-hydroxy-4-methylpent-2-ylamino | (2-hydroxy-5-chlorobenzyl)amino | methyl | 56.4/6.2/20.8 | 403.9 | 405.9 |
| 6 | 2-hydroxypent-3-ylamino | (2-hydroxy-5-chlorobenzyl)amino | methyl | 55.3/5.9/21.5 | 389.9 | 391.9 |
| 7 | 2-aminocyclohexylamino | (2-hydroxy-5-fluorobenzyl)amino | methyl | 59.2/6.3/25.4 | 384.4 | 386.4 |
| 8 | 4-aminocyclohexylamino | (2-hydroxy-5-fluorobenzyl)amino | methyl | 59.2/6.3/25.4 | 384.4 | 386.4 |
| 9 | (1-hydroxymethyl)propylamino | (2-hydroxy-5-fluorobenzyl)amino | methyl | 56.6/5.9/23.3 | 359.4 | 361.4 |
| 10 | 2-aminocyclohexylamino | (2-hydroxy-3-chlorobenzyl)amino | methyl | 56.8/6.0/24.4 | 400.9 | 402.9 |
| 11 | 4-aminocyclohexylamino | (2-hydroxy-3-chlorobenzyl)amino | methyl | 56.8/6.0/24.4 | 400.9 | 402.9 |
| 12 | 2-hydroxypent-3-ylamino | (2-hydroxy-3-chlorobenzyl)amino | methyl | 55.3/5.9/21.5 | 389.9 | 391.9 |
| 13 | 2-aminocyclohexylamino | (2-hydroxy-3-methylbenzyl)amino | methyl | 63.0/7.1/25.7 | 380.5 | 382.5 |
| 14 | 4-aminocyclohexylamino | (2-hydroxy-3-methylbenzyl)amino | methyl | 63.0/7.1/25.7 | 380.5 | 382.5 |
| 15 | 2-hydroxypropylamino | (2-hydroxy-3-methylbenzyl)amino | methyl | 59.6/6.5/24.5 | 341.4 | 343.4 |
| 16 | 2-hydroxy-2-methylpent-3-ylamino | (2-hydroxy-3-methylbenzyl)amino | methyl | 62.5/7.3/21.9 | 383.5 | 385.5 |
| 17 | 4-aminocyclohexylamino | (2-hydroxy-5-methylbenzyl)amino | methyl | 63.0/7.1/25.7 | 380.5 | 382.5 |
| 18 | (1-hydroxymethyl)propylamino | (2-hydroxy-5-methylbenzyl)amino | methyl | 60.6/6.8/23.6 | 355.4 | 357.4 |
| 19 | 3-hydroxy-3-methylbutylamino | (2-hydroxy-5-methylbenzyl)amino | methyl | 61.6/7.1/22.7 | 369.4 | 371.4 |

TABLE 1-continued

Compounds Prepared by the Method of Example 2

| | PURINE SUBSTITUENT | | | CHN ANALYSES | MS (ZMD)-ANALYSES | |
|---|---|---|---|---|---|---|
| No | R2 | R6 | R9 | [%] | [M − H]⁻ a) | [M + H]⁺ b) |
| 20 | 2-aminocyclohexylamino | (2,3-dihydroxybenzyl)amino | methyl | 59.5/6.6/25.6 | 382.4 | 384.4 |
| 21 | 4-aminocyclohexylamino | (2,3-dihydroxybenzyl)amino | methyl | 59.5/6.6/25.6 | 382.4 | 384.4 |
| 22 | (1-hydroxymethyl)propylamino | (2,3-dihydroxybenzyl)amino | methyl | 57.0/6.2/23.5 | 357.4 | 359.4 |
| 23 | (1-hydroxymethyl-2-methyl)propylamino | (2,3-dihydroxybenzyl)amino | methyl | 58.1/6.5/22.6 | 371.4 | 373.4 |
| 24 | 2-hydroxypent-3-ylamino | (2,3-dihydroxybenzyl)amino | methyl | 58.1/6.5/22.6 | 371.4 | 373.4 |
| 25 | 2-aminocyclohexylamino | (2,4-dihydroxybenzyl)amino | methyl | 59.5/6.6/25.6 | 382.4 | 384.4 |
| 26 | (1-hydroxymethyl)propylamino | (2,4-dihydroxybenzyl)amino | methyl | 57.0/6.2/23.5 | 357.4 | 359.4 |
| 27 | (1-hydroxymethyl-2-methyl)propylamino | (2,4-dihydroxybenzyl)amino | methyl | 58.1/6.5/22.6 | 371.4 | 373.4 |
| 28 | 2-aminocyclohexylamino | (2,5-dihydroxybenzyl)amino | methyl | 59.5/6.6/25.6 | 382.4 | 384.4 |
| 29 | 4-hydroxycyclohexylamino | (2,5-dihydroxybenzyl)amino | methyl | 59.4/6.3/21.9 | 383.4 | 385.4 |
| 30 | (1-hydroxymethyl)propylamino | (2,5-dihydroxybenzyl)amino | methyl | 57.0/6.2/23.5 | 357.4 | 359.4 |
| 31 | 2-aminocyclohexylamino | (2-hydroxy-3-methoxybenzyl)amino | methyl | 60.4/6.9/24.7 | 396.5 | 398.5 |
| 32 | 4-aminocyclohexylamino | (2-hydroxy-3-methoxybenzyl)amino | methyl | 60.4/6.9/24.7 | 396.5 | 398.5 |
| 33 | 2-hydroxypropylamino | (2-hydroxy-3-methoxybenzyl)amino | methyl | 57.0/6.2/23.5 | 357.4 | 359.4 |
| 34 | (1-hydroxymethyl)propylamino | (2-hydroxy-3-methoxybenzyl)amino | methyl | 58.1/6.5/22.6 | 371.4 | 373.4 |
| 35 | 2-aminocyclohexylamino | (2-hydroxy-4-methoxybenzyl)amino | methyl | 60.4/6.9/24.7 | 396.5 | 398.5 |
| 36 | 4-hydroxycyclohexylamino | (2-hydroxy-4-methoxybenzyl)amino | methyl | 60.3/6.6/21.1 | 397.5 | 399.5 |
| 37 | (1-hydroxymethyl)propylamino | (2-hydroxy-4-methoxybenzyl)amino | methyl | 58.1/6.5/22.6 | 371.4 | 373.4 |
| 38 | (1-hydroxymethyl-2-methyl)propylamino | (2-hydroxy-4-methoxybenzyl)amino | methyl | 59.1/6.8/21.8 | 385.4 | 387.5 |
| 39 | 2-hydroxypent-3-ylamino | (2-hydroxy-4-methoxybenzyl)amino | methyl | 59./6.8/21.8 | 385.4 | 387.4 |
| 40 | 2-aminocyclohexylamino | (2-hydroxy-5-methoxybenzyl)amino | methyl | 60.4/6.9/24.7 | 396.5 | 398.5 |
| 41 | 4-hydroxycyclohexylamino | (2-hydroxy-5-methoxybenzyl)amino | methyl | 60.3/6.6/21.1 | 397.5 | 399.5 |
| 42 | (1-hydroxymethyl)propylamino | (2-hydroxy-5-methoxybenzyl)amino | methyl | 58.1/6.5/22.6 | 371.4 | 373.4 |
| 43 | 2-hydroxypent-3-ylamino | (2,3-dihydroxy-4-methoxybenzyl)amino | methyl | 56.7/6.5/20.9 | 401.4 | 403.4 |
| 44 | 2-aminocyclohexylamino | (2,3-dihydroxy-5-methoxybenzyl)amino | methyl | 58.1/6.6/23.7 | 412.5 | 414.5 |
| 45 | 4-hydroxycyclohexylamino | (2,3-dihydroxy-5-methoxybenzyl)amino | methyl | 58.0/6.3/20.3 | 413.5 | 415.5 |
| 46 | (1-hydroxymethyl)propylamino | (2,5-dihydroxy-4-chlorobenzyl)amino | methyl | 52.0/5.4/21.4 | 391.8 | 393.8 | a) solution: MeOH p.a. + HCOOH
b) solution: MeOH p.a. + H₂O + NH₃

TABLE 2

Compounds Prepared by the Method of Example 2

| | PURINE SUBSTITUENT | | | CHN ANALYSES | MS (ZMD)-ANALYSES | |
|---|---|---|---|---|---|---|
| No | R2 | R6 | R9 | [%] | [M − H]⁻ a) | [M + H]⁺ b) |
| 47 | 2-aminocyclohexylamino | (2-hydroxy-5-chlorobenzyl)amino | ethyl | 57.8/6.3/23.6 | 414.9 | 416.9 |
| 48 | 4-aminocyclohexylamino | (2-hydroxy-5-chlorobenzyl)amino | ethyl | 57.8/6.3/23.6 | 414.9 | 416.9 |
| 49 | 2-hydroxypropylamino | (2-hydroxy-5-chlorobenzyl)amino | ethyl | 54.2/5.6/22.3 | 375.8 | 377.8 |
| 50 | (1-hydroxymethyl)propylamino | (2-hydroxy-5-chlorobenzyl)amino | ethyl | 55.3/5.9/21.5 | 389.9 | 391.9 |
| 51 | 4-aminocyclohexylamino | (2-hydroxy-5-fluorobenzyl)amino | ethyl | 60.1/6.6/24.5 | 398.5 | 400.5 |
| 52 | (1-hydroxymethyl)propylamino | (2-hydroxy-5-fluorobenzyl)amino | ethyl | 57.7/6.2/22.5 | 373.4 | 375.4 |
| 53 | 2-aminocyclohexylamino | (2-hydroxy-3-chlorobenzyl)amino | ethyl | 57.8/6.3/23.6 | 414.9 | 416.9 |
| 54 | 4-aminocyclohexylamino | (2-hydroxy-3-chlorobenzyl)amino | ethyl | 57.8/6.3/23.6 | 414.9 | 416.9 |
| 55 | 2-hydroxypent-3-ylamino | (2-hydroxy-3-chlorobenzyl)amino | ethyl | 56.4/6.2/20.8 | 403.9 | 405.9 |
| 56 | 2-aminocyclohexylamino | (2-hydroxy-3-methylbenzyl)amino | ethyl | 63.8/7.4/24.8 | 394.5 | 396.5 |
| 57 | 4-aminocyclohexylamino | (2-hydroxy-3-methylbenzyl)amino | ethyl | 63.8/7.4/24.8 | 394.5 | 396.5 |
| 58 | 2-hydroxy-2-methylpent-3-ylamino | (2-hydroxy-3-methylbenzyl)amino | ethyl | 63.3/7.6/21.1 | 397.5 | 399.5 |
| 59 | 2-aminocyclohexylamino | (2-hydroxy-5-methylbenzyl)amino | ethyl | 63.8/7.4/24.8 | 394.5 | 396.5 |
| 60 | 4-aminocyclohexylamino | (2-hydroxy-5-methylbenzyl)amino | ethyl | 63.8/7.4/24.8 | 394.5 | 396.5 |
| 61 | (1-hydroxymethyl)propylamino | (2-hydroxy-5-methylbenzyl)amino | ethyl | 61.6/7.1/22.7 | 369.4 | 371.4 |
| 62 | 3-hydroxy-3-methylbutylamino | (2-hydroxy-5-methylbenzyl)amino | ethyl | 62.5/7.3/21.9 | 383.5 | 385.5 |
| 63 | 4-aminocyclohexylamino | (2,3-dihydroxybenzyl)amino | ethyl | 60.4/6.9/24.7 | 396.5 | 398.5 |
| 64 | (1-hydroxymethyl)propylamino | (2,3-dihydroxybenzyl)amino | ethyl | 58.1/6.5/22.6 | 371.4 | 373.4 |
| 65 | 2-aminocyclohexylamino | (2,4-dihydroxybenzyl)amino | ethyl | 60.4/6.9/24.7 | 396.5 | 398.5 |
| 66 | (1-hydroxymethyl)propylamino | (2,4-dihydroxybenzyl)amino | ethyl | 58.1/6.5/22.6 | 371.4 | 373.4 |
| 67 | 2-aminocyclohexylamino | (2,5-dihydroxybenzyl)amino | ethyl | 60.4/6.9/24.7 | 396.5 | 398.5 |
| 68 | 4-hydroxycyclohexylamino | (2,5-dihydroxybenzyl)amino | ethyl | 60.3/6.6/21.09 | 397.5 | 399.5 |

TABLE 2-continued

Compounds Prepared by the Method of Example 2

| | PURINE SUBSTITUENT | | | CHN ANALYSES [%] | MS (ZMD)- ANALYSES | |
|---|---|---|---|---|---|---|
| | | | | | [M − H]⁻ a) | [M + H]⁺ b) |
| No | R2 | R6 | R9 | | | |
| 69 | (1-hydroxymethyl)propylamino | (2,5-dihydroxybenzyl)amino | ethyl | 58.1/6.5/22.6 | 371.4 | 373.4 |
| 70 | 4-aminocyclohexylamino | (2-hydroxy-3-methoxybenzyl)amino | ethyl | 61.3/7.1/23.8 | 410.5 | 412.5 |
| 71 | 2-hydroxypropylamino | (2-hydroxy-3-methoxybenzyl)amino | ethyl | 58.1/6.5/22.6 | 371.4 | 373.4 |
| 72 | 2-aminocyclohexylamino | (2-hydroxy-4-methoxybenzyl)amino | ethyl | 61.3/7.1/23.8 | 410.5 | 412.5 |
| 73 | (1-hydroxymethyl)propylamino | (2-hydroxy-4-methoxybenzyl)amino | ethyl | 59.1/6.8/21.8 | 385.4 | 387.4 |
| 74 | 4-hydroxycyclohexylamino | (2-hydroxy-5-methoxybenzyl)amino | ethyl | 61.2/6.8/20.4 | 411.5 | 413.5 |
| 75 | (1-hydroxymethyl)propylamino | (2-hydroxy-5-methoxybenzyl)amino | ethyl | 59.1/6.8/21.8 | 385.4 | 387.4 | a) solution: MeOH p.a. + HCOOH
b) solution: MeOH p.a. + $H_2O$ + $NH_3$

TABLE 3

Compounds Prepared by the Method of Example 2

| | PURINE SUBSTITUENT | | | CHN ANALYSES [%] | MS (ZMD)- ANALYSES | |
|---|---|---|---|---|---|---|
| | | | | | [M − H]⁻ a) | [M + H]⁺ b) |
| No | R2 | R6 | R9 | | | |
| 76 | 2-aminocyclohexylamino | (2-hydroxy-5-chlorobenzyl)amino | isopropyl | 58.7/6.6/22.8 | 428.9 | 430.9 |
| 77 | 4-aminocyclohexylamino | (2-hydroxy-5-chlorobenzyl)amino | isopropyl | 58.7/6.6/22.8 | 428.9 | 430.9 |
| 78 | 2-hydroxypropylamino | (2-hydroxy-5-chlorobenzyl)amino | isopropyl | 55.3/5.9/21.5 | 389.9 | 391.9 |
| 79 | (1-hydroxymethyl)propylamino | (2-hydroxy-5-chlorobenzyl)amino | isopropyl | 56.4/6.2/20.8 | 403.9 | 405.9 |
| 80 | (1-hydroxymethyl-2-methyl)propylamino | (2-hydroxy-5-chlorobenzyl)amino | isopropyl | 57.3/6.5/20.1 | 417.9 | 419.9 |
| 81 | 2-hydroxy-2-methylpropylamino | (2-hydroxy-5-chlorobenzyl)amino | isopropyl | 56.4/6.2/20.8 | 403.9 | 405.9 |
| 82 | 3-hydroxy-3-methylbut-2-ylamino | (2-hydroxy-5-chlorobenzyl)amino | isopropyl | 57.3/6.5/20.1 | 417.9 | 419.9 |
| 83 | 3-hydroxy-3-methylbutylamino | (2-hydroxy-5-chlorobenzyl)amino | isopropyl | 57.3/6.5/20.1 | 417.9 | 419.9 |
| 84 | 4-hydroxy-4-methylpent-2-ylamino | (2-hydroxy-5-chlorobenzyl)amino | isopropyl | 58.3/6.8/19.4 | 431.9 | 433.9 |
| 85 | 2-hydroxypent-3-ylamino | (2-hydroxy-5-chlorobenzyl)amino | isopropyl | 57.3/6.5/20.1 | 417.9 | 419.9 |
| 86 | 2-aminocyclohexylamino | (2-hydroxy-5-fluorobenzyl)amino | isopropyl | 61.0/6.8/23.7 | 412.5 | 414.5 |
| 87 | 4-aminocyclohexylamino | (2-hydroxy-5-fluorobenzyl)amino | isopropyl | 61.0/6.8/23.7 | 412.5 | 414.5 |
| 88 | 2-hydroxypropylamino | (2-hydroxy-5-fluorobenzyl)amino | isopropyl | 57.7/6.2/22.5 | 373.4 | 375.4 |
| 89 | (1-hydroxymethyl)propylamino | (2-hydroxy-5-fluorobenzyl)amino | isopropyl | 58.8/6.5/21.6 | 387.4 | 389.4 |
| 90 | 2-hydroxy-2-methylpent-3-ylamino | (2-hydroxy-5-fluorobenzyl)amino | isopropyl | 60.6/7.0/20.2 | 415.5 | 417.5 |
| 91 | 2-hydroxypent-3-ylamino | (2-hydroxy-5-fluorobenzyl)amino | isopropyl | 59.7/6.8/20.1 | 401.5 | 403.5 |
| 92 | 2-aminocyclohexylamino | (2-hydroxy-3-chlorobenzyl)amino | isopropyl | 58.7/6.6/22.8 | 428.9 | 430.9 |
| 93 | 4-aminocyclohexylamino | (2-hydroxy-3-chlorobenzyl)amino | isopropyl | 58.7/6.6/22.8 | 428.9 | 430.9 |
| 94 | (1-hydroxymethyl)propylamino | (2-hydroxy-3-chlorobenzyl)amino | isopropyl | 56.4/6.2/20.8 | 403.9 | 405.9 |
| 95 | (1-hydroxymethyl-2-methyl)propylamino | (2-hydroxy-3-chlorobenzyl)amino | isopropyl | 57.3/6.5/20.1 | 417.9 | 419.9 |
| 96 | 2-hydroxy-2-methylpropylamino | (2-hydroxy-3-chlorobenzyl)amino | isopropyl | 56.4/6.2/20.8 | 403.9 | 405.9 |
| 97 | 2-hydroxypent-3-ylamino | (2-hydroxy-3-chlorobenzyl)amino | isopropyl | 57.3/6.5/20.1 | 417.9 | 419.9 |
| 98 | 2-aminocyclohexylamino | (2-hydroxy-3-methylbenzyl)amino | isopropyl | 64.5/7.6/23.9 | 408.5 | 410.5 |
| 99 | 4-aminocyclohexylamino | (2-hydroxy-3-methylbenzyl)amino | isopropyl | 64.5/7.6/23.9 | 408.5 | 410.5 |
| 100 | 2-hydroxypropylamino | (2-hydroxy-3-methylbenzyl)amino | isopropyl | 61.6/7.1/22.7 | 369.4 | 371.4 |
| 101 | (1-hydroxymethyl)propylamino | (2-hydroxy-3-methylbenzyl)amino | isopropyl | 62.5/7.3/21.9 | 383.5 | 385.5 |
| 102 | 3-hydroxy-3-methylbutylamino | (2-hydroxy-3-methylbenzyl)amino | isopropyl | 63.3/7.6/21.1 | 397.5 | 399.5 |
| 103 | 2-hydroxy-2-methylpent-3-ylamino | (2-hydroxy-3-methylbenzyl)amino | isopropyl | 64.1/7.8/20.4 | 411.5 | 413.5 |
| 104 | 2-hydroxypent-3-ylamino | (2-hydroxy-3-methylbenzyl)amino | isopropyl | 63.3/7.6/21.1 | 397.5 | 399.5 |
| 105 | 2-aminocyclohexylamino | (2-hydroxy-5-methylbenzyl)amino | isopropyl | 64.5/7.6/23.9 | 408.5 | 410.5 |
| 106 | 4-aminocyclohexylamino | (2-hydroxy-5-methylbenzyl)amino | isopropyl | 64.5/7.6/23.9 | 408.5 | 410.5 |
| 107 | (1-hydroxymethyl)propylamino | (2-hydroxy-5-methylbenzyl)amino | isopropyl | 62.5/7.3/21.9 | 383.5 | 385.5 |
| 108 | 3-hydroxy-3-methylbutylamino | (2-hydroxy-5-methylbenzyl)amino | isopropyl | 63.3/7.6/21.1 | 397.5 | 399.5 |
| 109 | 2-hydroxy-2-methylpent-3-ylamino | (2-hydroxy-5-methylbenzyl)amino | isopropyl | 64.1/7.8/20.4 | 411.5 | 413.5 |
| 110 | 2-hydroxypent-3-ylamino | (2-hydroxy-5-methylbenzyl)amino | isopropyl | 63.3/7.6/21.1 | 397.5 | 399.5 |
| 111 | 2-aminocyclohexylamino | (2,3-dihydroxybenzyl)amino | isopropyl | 61.3/7.1/23.8 | 410.5 | 412.5 |
| 112 | 4-aminocyclohexylamino | (2,3-dihydroxybenzyl)amino | isopropyl | 61.3/7.1/23.8 | 410.5 | 412.5 |
| 113 | (1-hydroxymethyl)propylamino | (2,3-dihydroxybenzyl)amino | isopropyl | 59.1/6.8/21.8 | 385.4 | 387.4 |
| 114 | (1-hydroxymethyl-2-methyl)propylamino | (2,3-dihydroxybenzyl)amino | isopropyl | 60.0/7.1/21.0 | 399.5 | 401.5 |
| 115 | 4-hydroxy-4-methylpent-2-ylamino | (2,3-dihydroxybenzyl)amino | isopropyl | 60.9/7.3/20.3 | 413.5 | 415.5 |

TABLE 3-continued

Compounds Prepared by the Method of Example 2

| | PURINE SUBSTITUENT | | | CHN ANALYSES | MS (ZMD)-ANALYSES | |
|---|---|---|---|---|---|---|
| No | R2 | R6 | R9 | [%] | $[M-H]^-$ a) | $[M+H]^+$ b) |
| 116 | 2-hydroxy-2-methylpent-3-ylamino | (2,3-dihydroxybenzyl)amino | isopropyl | 60.9/7.3/20.3 | 413.5 | 415.5 |
| 117 | 2-hydroxypent-3-ylamino | (2,3-dihydroxybenzyl)amino | isopropyl | 60.0/7.1/21.0 | 399.5 | 401.5 |
| 118 | 2-aminocyclohexylamino | (2,4-dihydroxybenzyl)amino | isopropyl | 61.3/7.1/23.8 | 410.5 | 412.5 |
| 119 | (1-hydroxymethyl)propylamino | (2,4-dihydroxybenzyl)amino | isopropyl | 59.1/6.8/21.8 | 385.4 | 387.4 |
| 120 | (1-hydroxymethyl-2-methyl)propylamino | (2,4-dihydroxybenzyl)amino | isopropyl | 60.0/7.1/21.0 | 399.5 | 401.5 |
| 121 | 2-aminocyclohexylamino | (2,5-dihydroxybenzyl)amino | isopropyl | 61.3/7.1/23.8 | 410.5 | 412.5 |
| 122 | 4-hydroxycyclohexylamino | (,5-dihydroxybenzyl)amino | isopropyl | 61.2/6.8/20.4 | 411.5 | 413.5 |
| 123 | (1-hydroxymethyl)propylamino | (3,5-dihydroxybenzyl)amino | isopropyl | 59.1/6.8/21.8 | 385.4 | 387.4 |
| 124 | (1-hydroxymethyl-2-methyl)propylamino | (2,5-dihydroxybenzyl)amino | isopropyl | 60.0/7.1/21.0 | 399.5 | 401.5 |
| 125 | 2-aminocyclohexylamino | (2-hydroxy-3-methoxybenzyl)amino | isopropyl | 62.1/7.3/23.0 | 424.5 | 426.5 |
| 126 | 4-aminocyclohexylamino | (2-hydroxy-3-methoxybenzyl)amino | isopropyl | 62.1/7.3/23.0 | 424.5 | 426.5 |
| 127 | 2-hydroxypropylamino | (2-hydroxy-3-methoxybenzyl)amino | isopropyl | 59.1/6.8/21.8 | 385.4 | 387.4 |
| 128 | (1-hydroxymethyl)propylamino | (2-hydroxy-3-methoxybenzyl)amino | isopropyl | 60.0/7.1/21.0 | 399.5 | 401.5 |
| 129 | (1-hydroxymethyl-2-methyl)propylamino | (2-hydroxy-3-methoxybenzyl)amino | isopropyl | 60.9/7.3/20.3 | 413.5 | 415.5 |
| 130 | 2-hydroxy-2-methylpropylamino | (2-hydroxy-3-methoxybenzyl)amino | isopropyl | 60.0/7.1/21.0 | 399.5 | 401.5 |
| 131 | 3-hydroxy-3-methylbut-2-ylamino | (2-hydroxy-3-methoxybenzyl)amino | isopropyl | 60.9/7.3/20.3 | 413.5 | 415.5 |
| 132 | 3-hydroxy-3-methylbutylamino | (2-hydroxy-3-methoxybenzyl)amino | isopropyl | 60.9/7.3/20.3 | 413.5 | 415.5 |
| 133 | 4-hydroxy-4-methylpent-2-ylamino | (2-hydroxy-3-methoxybenzyl)amino | isopropyl | 61.6/7.5/19.6 | 427.5 | 429.5 |
| 134 | 2-hydroxypent-3-ylamino | (2-hydroxy-3-methoxybenzyl)amino | isopropyl | 60.9/7.3/20.3 | 413.5 | 415.5 |
| 135 | 2-aminoethylamino | (2-hydroxy-3-methoxybenzyl)amino | isopropyl | 58.2/6.8/26.4 | 370.4 | 372.4 |
| 136 | 4-hydroxycyclohexylamino | (2-hydroxy-3-methoxybenzyl)amino | isopropyl | 61.9/6.8/19.7 | 425.5 | 427.5 |
| 137 | 2-aminocyclohexylamino | (2-hydroxy-4-methoxybenzyl)amino | isopropyl | 62.1/7.3/23.0 | 424.5 | 426.5 |
| 138 | 4-hydroxycyclohexylamino | (2-hydroxy-4-methoxybenzyl)amino | isopropyl | 62.0/7.1/19.7 | 425.5 | 427.5 |
| 139 | (1-hydroxymethyl)propylamino | (2-hydroxy-4-methoxybenzyl)amino | isopropyl | 60.0/7.1/21.0 | 399.5 | 401.5 |
| 140 | (1-hydroxymethyl-2-methyl)propylamino | (2-hydroxy-4-methoxybenzyl)amino | isopropyl | 60.9/7.3/20.3 | 413.5 | 415.5 |
| 141 | 2-hydroxy-2-methylpropylamino | (2-hydroxy-4-methoxybenzyl)amino | isopropyl | 60.0/7.1/21.0 | 399.5 | 401.5 |
| 142 | 2-hydroxypent-3-ylamino | (2-hydroxy-4-methoxybenzyl)amino | isopropyl | 60.9/7.3/20.3 | 413.5 | 415.5 |
| 143 | 2-aminocyclohexylamino | (2-hydroxy-5-methoxybenzyl)amino | isopropyl | 62.1/7.3/23.0 | 424.5 | 426.5 |
| 144 | 4-hydroxycyclohexylamino | (2-hydroxy-5-mercaptobenzyl)amino | isopropyl | 58.9/6.6/19.6 | 427.5 | 429.5 |
| 145 | (1-hydroxymethyl)propylamino | (2-hydroxy-5-nitrobenzyl)amino | isopropyl | 54.9/6.1/23.6 | 414.4 | 416.4 |
| 146 | (1-hydroxymethyl-2-methyl)propylamino | (2-hydroxy-5-nitrobenzyl)amino | isopropyl | 55.9/6.3/22.8 | 428.5 | 430.5 | a) solution: MeOH p.a. + HCOOH
b) solution: MeOH p.a. + $H_2O$ + $NH_3$

TABLE 4

Compounds Prepared by the Method of Example 2

| | PURINE SUBSTITUENT | | | CHN ANALYSES | MS (ZMD)-ANALYSES | |
|---|---|---|---|---|---|---|
| No | R2 | R6 | R9 | [%] | $[M-H]^-$ a) | $[M+H]^+$ b) |
| 147 | 4-aminocyclohexylamino | (2-hydroxy-5-chlorobenzyl)amino | propyl | 58.7/6.6/22.8 | 428.9 | 430.9 |
| 148 | 4-hydroxycyclohexylamino | (2-hydroxy-5-chlorobenzyl)amino | propyl | 58.5/6.3/19.5 | 429.9 | 431.9 |
| 149 | 2-hydroxypropylamino | (2-hydroxy-5-fluorobenzyl)amino | propyl | 57.7/6.2/22.5 | 373.4 | 375.4 |
| 150 | (1-hydroxymethyl)propylamino | (2-hydroxy-3-methylbenzyl)amino | propyl | 62.5/7.3/21.9 | 383.5 | 385.5 |
| 151 | heptylamino | (2-hydroxy-5-methylbenzyl)amino | propyl | 67.6/7.9/20.6 | 407.5 | 409.5 |
| 152 | (1-hydroxymethyl-2-methyl)propylamino | (2-hydroxy-3-methoxybenzyl)amino | propyl | 60.9/7.3/20.3 | 413.5 | 415.5 |
| 153 | 2-hydroxy-2-methylpropylamino | (2-hydroxy-3-methoxybenzyl)amino | propyl | 60.0/7.1/21.0 | 399.5 | 401.5 |
| 154 | 3-hydroxy-3-methylbut-2-ylamino | (2-hydroxy-5-methoxybenzyl)amino | propyl | 60.9/7.3/20.3 | 413.5 | 415.5 |
| 155 | 3-hydroxy-3-methylbutylamino | (2,3-dihydroxybenzyl)amino | propyl | 60.0/7.1/21.0 | 399.5 | 401.5 |
| 156 | 4-hydroxy-4-methylpent-2-ylamino | (2,4-dihydroxybenzyl)amino | propyl | 60.9/7.3/20.3 | 413.5 | 415.5 | a) solution: MeOH p.a. + HCOOH
b) solution: MeOH p.a. + $H_2O$ + $NH_3$

TABLE 5

Compounds Prepared by the Method of Example 2

| | PURINE SUBSTITUENT | | | CHN ANALYSES | MS (ZMD)-ANALYSES | |
|---|---|---|---|---|---|---|
| No | R2 | R6 | R9 | [%] | [M − H]⁻ a) | [M + H]⁺ b) |
| 157 | 4-aminocyclohexylamino | (2-hydroxy-5-chlorobenzyl)amino | cyclohexyl | 61.3/6.9/20.9 | 469.0 | 471.0 |
| 158 | (1-hydroxymethyl)propylamino | (2-hydroxy-5-chlorobenzyl)amino | cyclohexyl | 59.4/6.6/18.9 | 444.0 | 446.0 |
| 159 | (1-hydroxymethyl-2-methyl)propylamino | (2-hydroxy-5-chlorobenzyl)amino | cyclohexyl | 60.2/6.8/18.3 | 458.0 | 460.0 |
| 160 | 2-aminocyclohexylamino | (2-hydroxy-5-fluorobenzyl)amino | cyclohexyl | 63.6/7.1/21.6 | 452.6 | 454.6 |
| 161 | 4-aminocyclohexylamino | (2-hydroxy-5-fluorobenzyl)amino | cyclohexyl | 63.6/7.1/21.6 | 452.6 | 454.6 |
| 162 | (1-hydroxymethyl)propylamino | (2-hydroxy-5-fluorobenzyl)amino | cyclohexyl | 61.7/6.8/19.6 | 427.5 | 429.5 |
| 163 | 2-aminocyclohexylamino | (2-hydroxy-5-chlorobenzyl)amino | cyclohexyl | 61.3/6.9/20.9 | 469.0 | 471.0 |
| 164 | 4-aminocyclohexylamino | (2-hydroxy-3-methylbenzyl)amino | cyclohexyl | 66.8/7.9/21.8 | 448.6 | 450.6 |
| 165 | 2-hydroxy-2-methylpent-3-ylamino | (2-hydroxy-3-methylbenzyl)amino | cyclohexyl | 66.3/8.0/18.6 | 451.6 | 453.6 |
| 166 | 4-aminocyclohexylamino | (2-hydroxy-5-methylbenzyl)amino | cyclohexyl | 66.8/7.9/21.9 | 448.6 | 450.6 |
| 167 | (1-hydroxymethyl)propylamino | (2-hydroxy-5-methylbenzyl)amino | cyclohexyl | 65.1/7.6/19.8 | 423.5 | 425.5 |
| 168 | 3-hydroxy-3-methylbutylamino | (2-hydroxy-5-methylbenzyl)amino | cyclohexyl | 65.7/7.8/19.2 | 437.6 | 439.6 |
| 169 | 2-aminocyclohexylamino | (2,3-dihydroxybenzyl)amino | cyclohexyl | 63.8/7.4/21.7 | 450.6 | 452.6 |
| 170 | 4-aminocyclohexylamino | (2,3-dihydroxybenzyl)amino | cyclohexyl | 63.8/7.4/21.7 | 450.6 | 452.6 |
| 171 | (1-hydroxymethyl)propylamino | (2,4-dihydroxybenzyl)amino | cyclohexyl | 62.0/7.1/19.7 | 425.5 | 427.5 |
| 172 | (1-hydroxymethyl-2-methyl)propylamino | (2,4-dihydroxybenzyl)amino | cyclohexyl | 62.7/7.3/19.1 | 439.5 | 441.5 |
| 173 | 2-aminocyclohexylamino | (2,5-dihydroxybenzyl)amino | cyclohexyl | 63.8/7.4/21.7 | 450.6 | 452.6 |
| 174 | 2-hydroxypropylamino | (2-hydroxy-3-methoxybenzyl)amino | cyclohexyl | 62.0/7.1/19.7 | 425.5 | 427.5 |
| 175 | (1-hydroxymethyl)propylamino | (2-hydroxy-3-methoxybenzyl)amino | cyclohexyl | 62.7/7.3/19.1 | 439.5 | 441.5 |
| 176 | 2-hydroxypent-3-ylamino | (2-hydroxy-3-methoxybenzyl)amino | cyclohexyl | 63.4/7.5/18.5 | 453.6 | 455.6 |
| 177 | 2-aminocyclohexylamino | (2-hydroxy-4-methoxybenzyl)amino | cyclohexyl | 64.5/7.6/21.1 | 464.6 | 466.6 |
| 178 | (1-hydroxymethyl)propylamino | (2-hydroxy-5-methoxybenzyl)amino | cyclohexyl | 62.7/7.3/19.1 | 439.5 | 441.5 | a) solution: MeOH p.a. + HCOOH
b) solution: MeOH p.a. + H₂O + NH₃

TABLE 6

Compounds Prepared by the Method of Example 2

| | PURINE SUBSTITUENT | | | CHN ANALYSES | MS (ZMD)-ANALYSES | |
|---|---|---|---|---|---|---|
| No | R2 | R6 | R9 | [%] | [M − H]⁻ a) | [M + H]⁺ b) |
| 179 | 2-aminocyclohexylamino | (2-hydroxy-5-chlorobenzyl)amino | benzyl | 62.8/5.9/20.5 | 477.0 | 479.0 |
| 180 | 4-aminocyclohexylamino | (2-hydroxy-5-chlorobenzyl)amino | benzyl | 62.8/5.9/20.5 | 477.0 | 479.0 |
| 181 | 2-hydroxypropylamino | (2-hydroxy-5-chlorobenzyl)amino | benzyl | 60.2/5.3/19.2 | 437.9 | 439.9 |
| 182 | (1-hydroxymethyl)propylamino | (2-hydroxy-5-chlorobenzyl)amino | benzyl | 61.0/5.6/18.6 | 451.9 | 453.9 |
| 183 | (1-hydroxymethyl-2-methyl)propylamino | (2-hydroxy-5-chlorobenzyl)amino | benzyl | 61.7/5.8/18.0 | 466.0 | 468.0 |
| 184 | 4-hydroxy-4-methylpent-2-ylamino | (2-hydroxy-5-chlorobenzyl)amino | benzyl | 62.4/6.1/17.5 | 480.0 | 482.0 |
| 185 | 2-hydroxypent-3-ylamino | (2-hydroxy-5-chlorobenzyl)amino | benzyl | 61.7/5.8/18.0 | 466.0 | 468.0 |
| 186 | 2-aminocyclohexylamino | (2-hydroxy-5-fluorobenzyl)amino | benzyl | 65.1/6.1/21.2 | 460.5 | 462.5 |
| 187 | 4-aminocyclohexylamino | (2-hydroxy-5-fluorobenzyl)amino | benzyl | 65.1/6.1/21.2 | 460.5 | 462.5 |
| 188 | (1-hydroxymethyl)propylamino | (2-hydroxy-5-fluorobenzyl)amino | benzyl | 63.3/5.8/19.3 | 435.5 | 437.5 |
| 189 | 2-aminocyclohexylamino | (2-hydroxy-3-chlorobenzyl)amino | benzyl | 62.8/5.9/20.5 | 477.0 | 479.0 |
| 190 | 4-aminocyclohexylamino | (2-hydroxy-3-chlorobenzyl)amino | benzyl | 62.8/5.9/20.5 | 477.0 | 479.0 |
| 191 | 2-hydroxypent-3-ylamino | (2-hydroxy-3-chlorobenzyl)amino | benzyl | 61.7/5.8/18.0 | 466.0 | 468.0 |
| 192 | 2-aminocyclohexylamino | (2-hydroxy-3-methylbenzyl)amino | benzyl | 68.3/6.8/21.4 | 456.6 | 458.6 |
| 193 | 4-aminocyclohexylamino | (2-hydroxy-3-methylbenzyl)amino | benzyl | 68.3/6.8/21.4 | 456.6 | 458.6 |
| 194 | 2-hydroxy-2-methylpent-3-ylamino | (2-hydroxy-3-methylbenzyl)amino | benzyl | 67.8/7.0/18.3 | 459.6 | 461.6 |
| 195 | 2-aminocyclohexylamino | (2-hydroxy-5-methylbenzyl)amino | benzyl | 68.3/6.8/21.4 | 456.6 | 458.6 |
| 196 | 4-aminocyclohexylamino | (2-hydroxy-5-methylbenzyl)amino | benzyl | 68.3/6.8/21.4 | 456.6 | 458.6 |
| 197 | (1-hydroxymethyl)propylamino | (2-hydroxy-5-methylbenzyl)amino | benzyl | 66.7/6.5/19.4 | 431.5 | 433.5 |
| 198 | 3-hydroxy-3-methylbutylamino | (2-hydroxy-5-methylbenzyl)amino | benzyl | 67.2/6.8/18.8 | 445.5 | 447.6 |
| 199 | 2-aminocyclohexylamino | (2,3-dihydroxybenzyl)amino | benzyl | 65.3/6.4/21.3 | 458.5 | 450.5 |

TABLE 6-continued

Compounds Prepared by the Method of Example 2

| No | PURINE SUBSTITUENT | | | CHN ANALYSES [%] | MS (ZMD)-ANALYSES | |
|---|---|---|---|---|---|---|
| | R2 | R6 | R9 | | [M − H]⁻ a) | [M + H]⁺ b) |
| 200 | 4-aminocyclohexylamino | (2,3-dihydroxybenzyl)amino | benzyl | 65.3/6.4/21.3 | 458.5 | 460.5 |
| 201 | (1-hydroxymethyl)propylamino | (2,3-dihydroxybenzyl)amino | benzyl | 63.6/6.0/19.3 | 433.5 | 435.5 |
| 202 | (1-hydroxymethyl-2-methyl)propylamino | (2,3-dihydroxybenzyl)amino | benzyl | 64.3/6.3/18.7 | 447.5 | 449.5 |
| 203 | 2-hydroxypent-3-ylamino | (2,3-dihydroxybenzyl)amino | benzyl | 64.3/6.3/18.7 | 447.5 | 449.5 |
| 204 | 2-aminocyclohexylamino | (2,4-dihydroxybenzyl)amino | benzyl | 65.3/6.4/21.3 | 458.5 | 460.5 |
| 205 | (1-hydroxymethyl)propylamino | (2,4-dihydroxybenzyl)amino | benzyl | 63.6/6.0/19.3 | 433.5 | 435.5 |
| 206 | (1-hydroxymethyl-2-methyl)propylamino | (2,4-dihydroxybenzyl)amino | benzyl | 64.3/6.3/18.7 | 447.5 | 449.5 |
| 207 | 2-aminocyclohexylamino | (2,5-dihydroxybenzyl)amino | benzyl | 65.3/6.4/21.3 | 458.5 | 460.5 |
| 208 | 4-hydroxycyclohexylamino | (2,5-dihydroxybenzyl)amino | benzyl | 65.2/6.1/18.3 | 459.5 | 461.5 |
| 209 | (1-hydroxymethyl)propylamino | (2,5-dihydroxybenzyl)amino | benzyl | 63.6/6.0/19.3 | 433.5 | 435.5 |
| 210 | 2-aminocyclohexylamino | (2-hydroxy-3-methoxybenzyl)amino | benzyl | 65.9/6.6/20.7 | 472.6 | 474.6 |
| 211 | 4-aminocyclohexylamino | (2-hydroxy-3-methoxybenzyl)amino | benzyl | 65.9/6.6/20.7 | 472.6 | 474.6 |
| 212 | (1-hydroxymethyl)propylamino | (2-hydroxy-3-methoxybenzyl)amino | benzyl | 64.3/6.3/18.7 | 447.5 | 449.5 |
| 213 | 2-hydroxypent-3-ylamino | (2-hydroxy-3-methoxybenzyl)amino | benzyl | 64.9/6.5/18.2 | 461.5 | 463.5 |
| 214 | 2-aminocyclohexylamino | (2-hydroxy-4-methoxybenzyl)amino | benzyl | 65.9/6.6/20.7 | 472.6 | 474.6 |
| 215 | 4-hydroxycyclohexylamino | (2-hydroxy-4-methoxybenzyl)amino | benzyl | 65.8/6.4/17.7 | 473.6 | 475.6 |
| 216 | (1-hydroxymethyl)propylamino | (2-hydroxy-4-methoxybenzyl)amino | benzyl | 64.3/6.3/18.7 | 447.5 | 449.5 |
| 217 | (1-hydroxymethyl-2-methyl)propylamino | (2-hydroxy-4-methoxybenzyl)amino | benzyl | 64.9/6.5/18.2 | 461.5 | 463.5 |
| 218 | 2-hydroxypent-3-ylamino | (2-hydroxy-4-methoxybenzyl)amino | benzyl | 64.9/6.5/18.2 | 461.5 | 463.5 |
| 219 | 2-aminocyclohexylamino | (2-hydroxy-5-methoxybenzyl)amino | benzyl | 65.9/6.6/20.7 | 472.6 | 474.6 |
| 220 | 2-hydroxypropylamino | (2-hydroxy-5-methoxybenzyl)amino | benzyl | 63.6/6.0/19.3 | 433.5 | 435.5 |
| 221 | 4-hydroxycyclohexylamino | (2-hydroxy-5-methoxybenzyl)amino | benzyl | 65.8/6.4/17.7 | 473.6 | 475.6 |
| 222 | (1-hydroxymethyl)propylamino | (2-hydroxy-5-nitrobenzyl)amino | benzyl | 59.6/5.4/21.2 | 462.5 | 464.5 | a) solution: MeOH p.a. + HCOOH
b) solution: MeOH p.a. + H₂O + NH₃

TABLE 7

Compounds Prepared by the Method of Example 2

| No | PURINE SUBSTITUENT | | | CHN ANALYSES [%] | MS (ZMD)-ANALYSES | |
|---|---|---|---|---|---|---|
| | R2 | R6 | R9 | | [M − H]⁻ a) | [M + H]⁺ b) |
| 223 | 2-aminocyclohexylamino | (2-hydroxy-5-chlorobenzyl)amino | 3-pentyl | 60.3/7.0/21.4 | 456.3 | 458.3 |
| 224 | (1-hydroxymethyl)propylamino | (2-hydroxy-5-chlorobenzyl)amino | 3-pentyl | 58.3/6.8/19.4 | 431.0 | 433.0 |
| 225 | (1-hydroxymethyl-2-methyl)propylamino | (2-hydroxy-5-chlorobenzyl)amino | 3-pentyl | 59.1/7.0/18.8 | 445.0 | 447.0 |
| 226 | 2-aminocyclohexylamino | (2-hydroxy-5-fluorobenzyl)amino | 3-pentyl | 62.6/7.3/22.2 | 440.6 | 442.6 |
| 227 | 4-aminocyclohexylamino | (2-hydroxy-5-fluorobenzyl)amino | 3-pentyl | 62.6/7.3/22.2 | 440.6 | 442.6 |
| 228 | (1-hydroxymethyl)propylamino | (2-hydroxy-5-fluorobenzyl)amino | 3-pentyl | 60.6/7.0/20.2 | 415.5 | 417.5 |
| 229 | 4-aminocyclohexylamino | (2-hydroxy-3-methylbenzyl)amino | 3-pentyl | 65.9/8.1/22.4 | 436.6 | 438.6 |
| 230 | 4-aminocyclohexylamino | (2-hydroxy-5-methylbenzyl)amino | 3-pentyl | 65.9/8.1/22.4 | 436.6 | 438.6 |
| 231 | (1-hydroxymethyl)propylamino | (2-hydroxy-5-methylbenzyl)amino | 3-pentyl | 64.1/7.8/20.4 | 411.5 | 413.5 |
| 232 | 2-aminocyclohexylamino | (2,3-dihydroxybenzyl)amino | 3-pentyl | 62.9/7.6/22.3 | 438.6 | 440.6 |
| 233 | (1-hydroxymethyl)propylamino | (2,4-dihydroxybenzyl)amino | 3-pentyl | 60.8/7.3/20.3 | 413.5 | 415.5 |
| 234 | (1-hydroxymethyl-2-methyl)propylamino | (2,4-dihydroxybenzyl)amino | 3-pentyl | 61.7/7.5/19.6 | 427.5 | 429.5 |
| 235 | 2-aminocyclohexylamino | (2,5-dihydroxybenzyl)amino | 3-pentyl | 62.9/7.6/22.3 | 438.6 | 440.6 |
| 236 | 2-hydroxypropylamino | (2-hydroxy-3-methoxybenzyl)amino | 3-pentyl | 60.8/7.3/20.3 | 413.5 | 415.5 |
| 237 | (1-hydroxymethyl)propylamino | (2-hydroxy-3-methoxybenzyl)amino | 3-pentyl | 61.7/7.5/19.6 | 427.5 | 429.5 |
| 238 | 2-aminocyclohexylamino | (2-hydroxy-3-methoxybenzyl)amino | 3-pentyl | 63.6/7.8/21.6 | 453.6 | 455.6 |
| 239 | 2-aminocyclohexylamino | (2-hydroxy-4-methoxybenzyl)amino | 3-pentyl | 63.6/7.8/21.6 | 453.6 | 455.6 |
| 240 | (1-hydroxymethyl)propylamino | (2-hydroxy-5-methoxybenzyl)amino | 3-pentyl | 61.7/7.5/19.6 | 427.5 | 429.5 | a) solution: MeOH p.a. + HCOOH
b) solution: MeOH p.a. + H₂O + NH₃

TABLE 8

Compounds Prepared by the Method of Example 2

| | PURINE SUBSTITUENT | | | CHN ANALYSES | MS (ZMD)- ANALYSES | |
|---|---|---|---|---|---|---|
| | | | | | [M − H]⁻ | [M + H]⁺ |
| No | R2 | R6 | R9 | [%] | a) | b) |
| 241 | 2-aminocyclohexylamino | (2-hydroxy-5-chlorobenzyl)amino | isopentenyl | 60.3/7.0/21.4 | 456.3 | 458.3 |
| 242 | (1-hydroxymethyl)propylamino | (2-hydroxy-5-chlorobenzyl)amino | isopentenyl | 58.3/6.8/19.4 | 431.0 | 433.0 |
| 243 | (1-hydroxymethyl-2-methyl)propylamino | (2-hydroxy-5-chlorobenzyl)amino | isopentenyl | 59.1/7.0/18.8 | 445.0 | 447.0 |
| 244 | 2-aminocyclohexylamino | (2-hydroxy-5-fluorobenzyl)amino | isopentenyl | 62.6/7.3/22.2 | 440.6 | 442.6 |
| 245 | 4-aminocyclohexylamino | (2-hydroxy-5-fluorobenzyl)amino | isopentenyl | 62.6/7.3/22.2 | 440.6 | 442.6 |
| 246 | (1-hydroxymethyl)propylamino | (2-hydroxy-5-fluorobenzyl)amino | isopentenyl | 60.6/7.0/20.2 | 415.5 | 417.5 |
| 247 | 2-aminocyclohexylamino | (2-hydroxy-5-methylbenzyl)amino | isopentenyl | 65.9/8.1/22.4 | 436.6 | 438.6 |
| 248 | (1-hydroxymethyl)propylamino | (2-hydroxy-5-methylbenzyl)amino | isopentenyl | 64.1/7.8/20.4 | 411.5 | 413.5 |
| 249 | (1-hydroxymethyl)propylamino | (2-hydroxy-3-methoxybenzyl)amino | isopentenyl | 61.7/7.5/19.6 | 427.5 | 429.5 |
| 250 | 2-aminocyclohexylamino | (2-hydroxy-3-methoxybenzyl)amino | isopentenyl | 63.6/7.8/21.6 | 453.6 | 455.6 | a) solution: MeOH p.a. + HCOOH
b) solution: MeOH p.a. + H₂O + NH₃

Example 3

CDK Inhibition Assays

Selected compounds were tested for CDK1/cyclin B, CDK2/cyclin E, CDK5/p25, CDK7/cyclin H and CDK9/cyclin T inhibitory activity to determine the basic relationships between their structure and the inhibitory activity. Cdk/cyclin complexes were expressed in Sf9 cells co-infected with appropriate baculoviral construct. The cells were harvested 70 hours post infection in lysis buffer (50 mM Tris pH 7.4, 150 mM NaCl, 5 mM EDTA, 20 mM NaF, 1% Tween 20, protease inhibitors) for 30 min on ice and the soluble fraction was recovered by centrifugation at 14.000 g for 10 mM. The protein extract was stored at −80° C. until use. The final point test system for kinase activity measurement was used to carry out experiments on the kinetics under linear conditions. The assay mixture contained 1 mg/ml histone as a substrate for CDK1, CDK2 and CDK5 (Sigma Type III-S), (YSPTSPS)₃ peptide as a substrate for cdk7 and cdk9, 15 µM ATP, 0.2 µCi [γ-$^{33}$P] ATP and tested compound in a final volume of 20 µl, all in reaction buffer: 50 mM Hepes pH 7.4, 10 mM MgCl₂, 5 mM EGTA, 10 mM 2-glycerolphosphate, 1 mM NaF, 1 mM DTT and protease inhibitors. After 30 min, the incubations were stopped by adding 5% H₃PO₄ and then the proteins were separated by phosphocellulose binding. The measurement of kinase inhibition employed the digital imaging analyzer BAS 1800. The kinase activity was expressed as a percentage of maximum activity and the IC₅₀ value was determined by graphic analysis. The kinase activity is expressed as a percentage of maximum activity (FIG. 1).

TABLE 9

Kinase inhibitory activities of selected novel substituted 6-(2-hydroxybenzylamino)purine derivatives

| | PURINE SUBSTITUENT | | | IC₅₀ (µM) | |
|---|---|---|---|---|---|
| No | R6 | R2 | R9 | CDK2 | CDK9 |
| OC | benzyl | hydroxyethylamino | methyl | 7 | 19 |
| 1 | 2-hydroxy-5-chlorobenzylamino | 2-aminocyclohexylamino | methyl | 0.29 | 0.18 |
| 2 | 2-hydroxy-5-chlorobenzylamino | 4-aminocyclohexylamino | methyl | 0.27 | 0.15 |
| 3 | 2-hydroxy-5-chlorobenzylamino | (1-hydroxymethylpropyl)amino | methyl | 0.3 | 0.12 |
| 4 | 2-hydroxy-5-chlorobenzylamino | (1-hydroxymethyl-2-methyl)propylamino | methyl | 0.25 | 0.08 |
| 7 | 2-hydroxy-5-fluorobenzylamino | 2-aminocyclohexylamino | methyl | 0.26 | 0.15 |
| 8 | 2-hydroxy-5-fluorobenzylamino | 4-aminocyclohexylamino | methyl | 0.25 | 0.12 |
| 9 | 2-hydroxy-5-fluorobenzylamino | (1-hydroxymethylpropyl)amino | methyl | 0.3 | 0.17 |
| 31 | 2-hydroxy-3-methoxybenzylamino | 2-aminocyclohexylamino | methyl | 0.26 | 0.19 |
| 32 | 2-hydroxy-3-methoxybenzylamino | 4-aminocyclohexylamino | methyl | 0.22 | 0.18 |
| 34 | 2-hydroxy-3-methoxybenzylamino | (1-hydroxymethylpropyl)amino | methyl | 0.27 | 0.16 |
| 48 | 2-hydroxy-5-chlorobenzylamino | 4-aminocyclohexylamino | ethyl | 0.14 | 0.09 |
| 50 | 2-hydroxy-5-chlorobenzylamino | (1-hydroxymethylpropyl)amino | ethyl | 0.13 | 0.12 |
| 51 | 2-hydroxy-5-fluorobenzylamino | 4-aminocyclohexylamino | ethyl | 0.16 | 0.1 |
| 59 | 2-hydroxy-5-methylbenzylamino | 2-aminocyclohexylamino | ethyl | 0.12 | 0.05 |
| 70 | 2-hydroxy-3-methoxybenzylamino | 4-aminocyclohexylamino | ethyl | 0.11 | 0.07 |
| 73 | 2-hydroxy-4-methoxybenzylamino | (1-hydroxymethylpropyl)amino | ethyl | 0.17 | 0.09 |
| ROSC | benzylamino | (1-hydroxymethylpropyl)amino | isopropyl | 0.1 | 0.7 |
| 76 | 2-hydroxy-5-chlorobenzylamino | 2-aminocyclohexylamino | isopropyl | 0.05 | 0.03 |
| 77 | 2-hydroxy-5-chlorobenzylamino | 4-aminocyclohexylamino | isopropyl | 0.04 | 0.01 |
| 79 | 2-hydroxy-5-chlorobenzylamino | (1-hydroxymethylpropyl)amino | isopropyl | 0.07 | 0.04 |
| 80 | 2-hydroxy-5-chlorobenzylamino | (1-hydroxymethyl-2-methyl)propylamino | isopropyl | 0.06 | 0.05 |
| 81 | 2-hydroxy-5-chlorobenzylamino | 2-hydroxy-2-methylpropylamino | isopropyl | 0.03 | 0.02 |
| 82 | 2-hydroxy-5-chlorobenzylamino | 3-hydroxy-3-methylbut-2- | isopropyl | 0.04 | 0.01 |

TABLE 9-continued

Kinase inhibitory activities of selected novel substituted 6-(2-hydroxybenzylamino)purine derivatives

| | PURINE SUBSTITUENT | | | IC$_{50}$ (μM) | |
|---|---|---|---|---|---|
| No | R6 | R2 | R9 | CDK2 | CDK9 |
| | | enylamino | | | |
| 83 | 2-hydroxy-5-chlorobenzylamino | 3-hydroxy-3-methylbutylamino | isopropyl | 0.02 | 0.007 |
| 86 | 2-hydroxy-5-fluorobenzylamino | 2-aminocyclohexylamino | isopropyl | 0.04 | 0.02 |
| 87 | 2-hydroxy-5-fluorobenzylamino | 4-aminocyclohexylamino | isopropyl | 0.02 | 0.008 |
| 89 | 2-hydroxy-5-fluorobenzylamino | (1-hydroxymethylpropyl)amino | isopropyl | 0.05 | 0.02 |
| 101 | 2-hydroxy-3-methylbenzylamino | (1-hydroxymethylpropyl)amino | isopropyl | 0.1 | 0.04 |
| 107 | 2-hydroxy-5-methylbenzylamino | (1-hydroxymethylpropyl)amino | isopropyl | 0.02 | 0.006 |
| 113 | 2,3-dihydroxybenzylamino | (1-hydroxymethylpropyl)amino | isopropyl | 0.07 | 0.04 |
| 119 | 2,4-dihydroxybenzylamino | (1-hydroxymethylpropyl)amino | isopropyl | 0.08 | 0.05 |
| 121 | 2,5-dihydroxybenzylamino | 2-aminocyclohexylamino | isopropyl | 0.08 | 0.07 |
| 125 | 2-hydroxy-3-methoxybenzylamino | 2-aminocyclohexylamino | isopropyl | 0.02 | 0.007 |
| 126 | 2-hydroxy-3-methoxybenzylamino | 4-aminocyclohexylamino | isopropyl | 0.02 | 0.009 |
| 128 | 2-hydroxy-3-methoxybenzylamino | (1-hydroxymethylpropyl)amino | isopropyl | 0.07 | 0.04 |
| 127 | 2-hydroxy-3-methoxybenzylamino | 2-hydroxypropylamino | isopropyl | 0.08 | 0.06 |
| 136 | 2-hydroxy-3-methoxybenzylamino | 4-hydroxycyclohexylamino | isopropyl | 0.05 | 0.03 |
| 139 | 2-hydroxy-4-methoxybenzylamino | (1-hydroxymethylpropyl)amino | isopropyl | 0.09 | 0.04 |
| 223 | 2-hydroxy-5-fluorobenzylamino | 2-aminocyclohexylamino | 3-pentyl | 0.08 | 0.05 |
| 224 | 2-hydroxy-5-chlorobenzylamino | (1-hydroxymethylpropyl)amino | 3-pentyl | 0.09 | 0.06 |
| 227 | 2-hydroxy-5-fluorobenzylamino | 4-aminocyclohexylamino | 3-pentyl | 0.06 | 0.01 |
| 228 | 2-hydroxy-5-fluorobenzylamino | (1-hydroxymethylpropyl)amino | 3-pentyl | 0.07 | 0.04 |
| 237 | 2-hydroxy-3-methoxybenzylamino | (1-hydroxymethylpropyl)amino | 3-pentyl | 0.04 | 0.02 |
| 238 | 2-hydroxy-3-methoxybenzylamino | 2-aminocyclohexylamino | 3-pentyl | 0.06 | 0.04 |
| 240 | 2-hydroxy-5-methoxybenzylamino | (1-hydroxymethylpropyl)amino | 3-pentyl | 0.1 | 0.07 |

OC—olomoucine, ROSC—roscovitine, known in the art

Table 9 shows the results of inhibitory activity of novel compounds against CDK9 in comparison with CDK2 as well as the data on the prototype compounds olomoucine II and roscovitine. Most of the derivatives showed marked inhibitory activity in in vitro kinase assays. Modification of the benzyl ring by hydroxyl group in ortho-position led usually to increase in CDK9 inhibitory activity of the tested compound.

Example 4

Modulation of the Activity of β-Adrenergic Receptors

Figure 2:
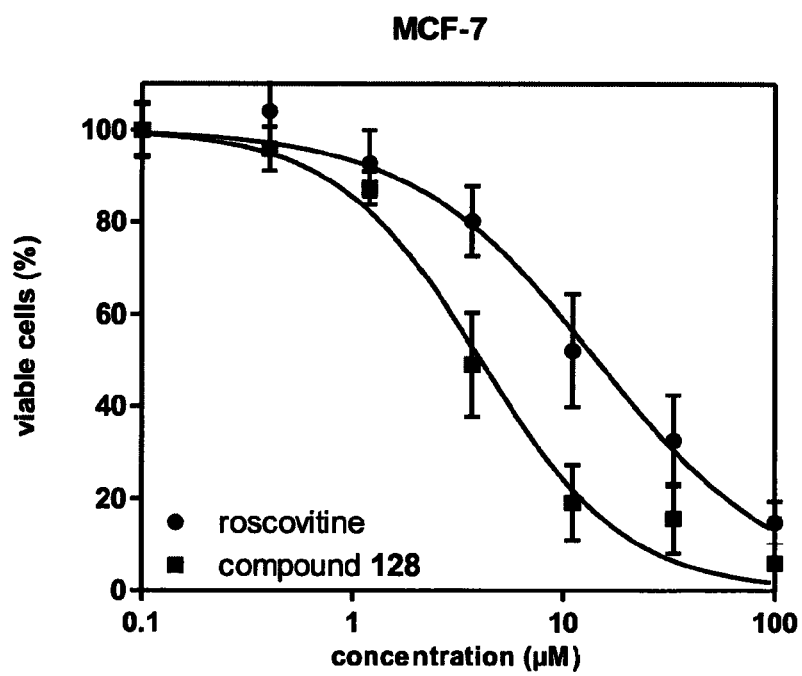
FIG. 2. displays the dose-dependent antiproliferative activity of purine derivative 128 against human tumor cell line MCF7, with roscovitine used as a standard. The cells were treated for 72 h with increasing concentrations of the compounds and then the number of viable cells was determined by a Calcein AM assay. Results represent the average±SD for three independent experiments. Compound 128 significantly reduces the number of living cells.

Mechanism of action of novel compounds is presented on FIG. 2. Rat C6 glioma (ATCC No CCL 107) was cultivated in monolayer in serum-free chemically defined medium containing Ham's F10/minimal essential medium (1:1 vol/vol), 2 mM L-glutamine, 1% (vol/vol) minimal essential medium vitamins (100×), 1% (vol/vol) minimal essential medium nonessential amino acids (100×), 100 U/ml penicillin, 100 μg/ml streptomycin and 30 nM sodium selenite. Incubation was at 37° C. in a humidified atmosphere. Assays were performed in the logaritmic growth phase at a density of $2.5 \times 10^5$ cells/cm$^2$. Intracellular cAMP synthesis was induced by addition of 5 μM (−) isoproterenol. After 30 min incubation at 37° C. the medium was removed and the cellular amount of cAMP determined using the cAMP-enzyme immunoassay kit of Amersham. The I$_{50}$ is determined from a dose-response curve in duplicate. The effect of several novel substituted 6-(2-hydroxybenzylamino)purine derivatives was measured after simultaneous addition with isoproterenol.

TABLE 10

Modulation of the activity of β-adrenergic receptors by selected novel substituted 6-(2-hydroxybenzylamino)purine derivatives

| | PURINE SUBSTITUENT | | | | IC$_{50}$ |
|---|---|---|---|---|---|
| No | R6 | R2 | R9 | EFFECT | (μM) |
| OC | benzyl | hydroxyethylamino | methyl | inactive | inactive |
| ROSC | benzyl | (1-hydroxymethylpropyl)amino | isopropyl | inactive | inactive |
| 86 | 2-hydroxy-5-fluorobenzylamino | 2-aminocyclohexylamino | isopropyl | inhibition | 8 ± 2 |
| 105 | 2-hydroxy-3-methylbenzylamino | 2-aminocyclohexylamino | isopropyl | inhibition | 12 ± 4 |
| 106 | 2-hydroxy-5-methylbenzylamino | 2-aminocyclohexylamino | isopropyl | inhibition | 7 ± 2 |
| 125 | 2-hydroxy-3-methoxybenzylamino | 2-aminocyclohexylamino | isopropyl | inhibition | 2 ± 0 |
| 126 | 2-hydroxy-3-methoxybenzylamino | 4-aminocyclohexylamino | isopropyl | inhibition | 4 ± 1 |
| 79 | 2-hydroxy-5-chlorobenzylamino | (1-hydroxymethylpropyl)amino | isopropyl | 1.5-fold activation | |
| 80 | 2-hydroxy-5-chlorobenzylamino | (1-hydroxymethyl-2-methyl)propylamino | isopropyl | 1.8-fold activation | |
| 81 | 2-hydroxy-5-chlorobenzylamino | 2-hydroxy-2-methylpropylamino | isopropyl | 1.7-fold activation | |
| 89 | 2-hydroxy-5-fluorobenzylamino | (1-hydroxymethylpropyl)amino | isopropyl | 1.9-fold activation | |
| 113 | 2,3-dihydroxybenzylamino | (1-hydroxymethylpropyl)amino | isopropyl | 2.3-fold activation | |
| 119 | 2,4-dihydroxybenzylamino | (1-hydroxymethylpropyl)amino | isopropyl | 1.6-fold activation | |

TABLE 10-continued

Modulation of the activity of β-adrenergic receptors by selected novel substituted 6-(2-hydroxybenzylamino)purine derivatives

| | PURINE SUBSTITUENT | | | | $IC_{50}$ |
|---|---|---|---|---|---|
| No | R6 | R2 | R9 | EFFECT | (μM) |
| 123 | 2,5-dihydroxybenzylamino | (1-hydroxymethylpropyl)amino | isopropyl | 1.7-fold activation | |
| 124 | 2,5-dihydroxybenzylamino | (1-hydroxymethyl-2-methyl-propyl)amino | isopropyl | 2.1-fold activation | |

As P2Y$_1$-like and A2 purinergic receptors, negatively and positively coupled to adenylate cyclase respectively, are present on rat C6 glioma. It has to be determined if the modulation of the synthesis of cAMP is due to inhibition of the activation of β-adrenergic receptors by isoproterenol are due to activation of purinergic receptors.

Example 5

In vitro Cytotoxic Activity of Novel Compounds

Cytotoxicity of the compounds is the major property determining their anticancer effect in vivo. One of the parameters used, as the basis for cytotoxicity assays, is the metabolic activity of viable cells. For example, a microtiter assay, which uses the Calcein AM, is now widely used to quantitate cell proliferation and cytotoxicity. For instance, this assay is used in drug screening programs and in chemosensitivity testing. Because only metabolically active cells cleave Calcein AM, these assays detect viable cells exclusively. The quantity of cleaved Calcein AM corresponds to the number of vital cells in the culture. We have been using the following cell lines: MCF7 (human breast adenocarcinoma), K562 (human chronic myelogenous leukaemia), HOS (human osteogenic sarcoma), HeLa (human cervical carcinoma), HL 60 (human promyelocytic leukaemia), G 361 (human malignant melanoma), CEM (human lymphoblastoid leukaemia). All cell lines were grown in DMEM medium (Gibco BRL) supplemented with 10% (v/v) fetal bovine serum and L-glutamine and maintained at 37° C. in a humidified atmosphere with 5% $CO_2$. For cytotoxicity assays, $10^4$ cells were seeded into each well of 96 well plate, allowed to stabilize for at least 2 h and then tested compounds were added at various concentrations ranging from 100 to 0.1 μM in triplicates. Three days after drug addition Calcein AM solution (Molecular Probes) was added and let to enter the cells for 1 hour. Fluorescence of viable cells was quantified using Fluoroskan Ascent (Microsystems). The $GI_{50}$ value, the drug concentration lethal to 50% of the tumour cells, was calculated from the obtained dose response curves (FIG. 2).

Cytoxicity of novel compounds was tested on a panel of cell lines of different histogenetic origin. Significant activities were found in all tumour cell lines tested (for example see Tab. 11). Notably, the higher effectiveness of novel derivatives was also found in cell lines bearing various mutations or deletions in cell cycle associated proteins, e.g. HL-60, BT549, Hela, U2OS, MDA-MB231, and Saos2. It indicates that these substances should be equally effective in tumours with various statuses of tumour suppressor genes, namely p53, Rb, etc.

TABLE 11

Cytotoxic activity of selected novel substituted 6-(2-hydroxybenzylamino)purine derivatives

| | PURINE SUBSTITUENT | | | $IC_{50}$ (μM) | | |
|---|---|---|---|---|---|---|
| No | R6 | R2 | R9 | MCF7 | K562 | HOS |
| OC | benzyl | 2-hydroxyethylamino | methyl | 133 | 163 | 144 |
| 1 | 2-hydroxy-5-chlorobenzylamino | 2-aminocyclohexylamino | methyl | 43 | 78 | 65 |
| 2 | 2-hydroxy-5-chlorobenzylamino | 4-aminocyclohexylamino | methyl | 46 | 82 | 64 |
| 3 | 2-hydroxy-5-chlorobenzylamino | (1-hydroxymethylpropyl)amino | methyl | 55 | 84 | 71 |
| 7 | 2-hydroxy-5-fluorobenzylamino | 2-aminocyclohexylamino | methyl | 35 | 61 | 47 |
| 8 | 2-hydroxy-5-fluorobenzylamino | 4-aminocyclohexylamino | methyl | 39 | 64 | 50 |
| 9 | 2-hydroxy-5-fluorobenzylamino | (1-hydroxymethylpropyl)amino | methyl | 42 | 67 | 53 |
| 31 | 2-hydroxy-3-methoxybenzylamino | 2-aminocyclohexylamino | methyl | 36 | 60 | 45 |
| 47 | 2-hydroxy-5-chlorobenzylamino | 2-aminocyclohexylamino | ethyl | 32 | 55 | 41 |
| 50 | 2-hydroxy-5-chlorobenzylamino | (1-hydroxymethylpropyl)amino | ethyl | 38 | 58 | 44 |
| 51 | 2-hydroxy-5-fluorobenzylamino | 4-aminocyclohexylamino | ethyl | 32 | 52 | 40 |
| 76 | 2-hydroxy-5-chlorobenzylamino | 2-aminocyclohexylamino | isopropyl | 2.8 | 9.9 | 4.1 |
| 79 | 2-hydroxy-5-chlorobenzylamino | (1-hydroxymethylpropyl)amino | isopropyl | 3.5 | 11.9 | 5.3 |
| 86 | 2-hydroxy-5-fluorobenzylamino | 2-aminocyclohexylamino | isopropyl | 1.8 | 7.6 | 3.2 |
| 89 | 2-hydroxy-5-fluorobenzylamino | (1-hydroxymethylpropyl)amino | isopropyl | 3.2 | 14.7 | 5.3 |
| 125 | 2-hydroxy-3-methoxybenzylamino | 2-aminocyclohexylamino | isopropyl | 3.2 | 10.9 | n.t. |
| 128 | 2-hydroxy-3-methoxybenzylamino | (1-hydroxymethylpropyl)amino | isopropyl | 5.0 | 15.5 | 5.9 |
| 113 | 2,3-dihydroxybenzylamino | (1-hydroxymethylpropyl)amino | isopropyl | 4.5 | 7.8 | 8.4 |
| 119 | 2,4-dihydroxybenzylamino | (1-hydroxymethylpropyl)amino | isopropyl | 4.3 | 13 | 8.1 |
| 107 | 2-hydroxy-5-methylbenzylamino | (1-hydroxymethylpropyl)amino | isopropyl | 6.6 | 24.9 | 18 |
| 123 | 2,5-dihydroxybenzylamino | (1-hydroxymethylpropyl)amino | isopropyl | 3.2 | 5.3 | 3.7 |
| 143 | 2-hydroxy-5-methoxybenzylamino | 2-aminocyclohexylamino | isopropyl | 5.0 | 13.1 | n.t. |
| | 2-hydroxy-5-chlorobenzylamino | 2-aminocyclohexylamino | 3-pentyl | 4.8 | 17.6 | 6.8 |
| | 2-hydroxy-5-chlorobenzylamino | (1-hydroxymethylpropyl)amino | 3-pentyl | 5.5 | 15.6 | 7.2 |
| | 2-hydroxy-5-fluorobenzylamino | 2-aminocyclohexylamino | 3-pentyl | 4.1 | 12.4 | 4.3 |
| | 2-hydroxy-5-fluorobenzylamino | (1-hydroxymethylpropyl)amino | 3-pentyl | 4.6 | 13.2 | 6.8 |

TABLE 11-continued

Cytotoxic activity of selected novel substituted 6-(2-hydroxybenzylamino)purine derivatives

| No | PURINE SUBSTITUENT | | | $IC_{50}$ (µM) | | |
| --- | --- | --- | --- | --- | --- | --- |
| | R6 | R2 | R9 | MCF7 | K562 | HOS |
| 179 | 2-hydroxy-5-chlorobenzylamino | 2-aminocyclohexylamino | benzyl | 8.7 | 19.5 | 10.2 |
| 186 | 2-hydroxy-5-fluorobenzylamino | 2-aminocyclohexylamino | benzyl | 6.9 | 15.4 | 9.3 |

Example 6

Inhibition of CDK9 and Inactivation of RNA Polymerase II

Effect of compounds on CDK9 activity in cells was monitored by site-specific phosphorylations of C-terminal domain of RNA polymerase II, a substrate of CDK9, by means of immunoblotting. For immunoblotting, cell were detached with rubber policeman and washed three times with ice-cold PBS and lysed in buffer (50 mM Tris, pH 7.4, 250 mM NaCl, 5 mM EDTA, 50 mM NaF, 1 mM $Na_3VO_4$, 1% Nonidet P40) containing mixture of protease and phosphatase inhibitors (Sigma-Aldrich, USA). 20 µg of total proteins were separated by SDS-polyacrylamide gel electrophoresis (SDS-PAGE) and transferred onto nitrocellulose membranes. Membranes were blocked in 5% milk and 0.1% Tween 20 in PBS and probed overnight with specific monoclonal antibodies or rabbit polyclonal sera. Primary antibodies specific for RNA polymerase II (all from Santa Cruz Biotechnology, California, USA) included: (i) N-20 used at 1 µg/ml, (ii) H14, specific for form phosphorylated at phosphoserine 5, used at 6 µg/ml and (iii) H5, specific for form phosphorylated at phosphoserine 2 used at 4 µg/ml. Additional primary mAb used in immunblots included (iv) anti-p53 (DO-1, in house) used at 1 µg/ml, (v) anti-p21$^{WAF1}$ (118, in house), used at 1 µg/ml), (vi) anti-actin (A-2066, Sigma-Aldrich St Louis, Mo., USA) used at 1 µg/ml, (vii) anti-T-antigen (419, in house), used at 1 µg/ml. All primary antibodies were diluted in PBS containing 5% powdered milk; 0.1% Tween 20. Peroxidase conjugated rabbit anti-mouse immunoglobulin or porcine anti-rabbit immunoglobulin antisera (DAKO, Denmark) were used as the secondary antibodies and visualised with ECL reagents (Amersham-Pharmacia, Little Chalfont, UK).

Figure 3:
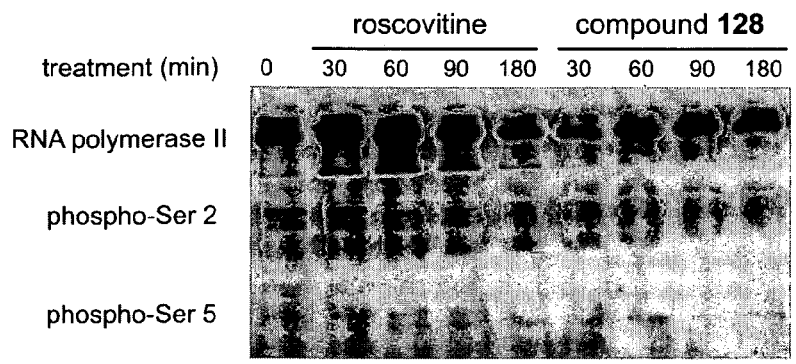
FIG. 3 shows how compound 128 and roscovitine modulate expression of RNA polymerase II and its phosphorylation status. Cells were incubated with the compounds at the indicated time points, harvested and whole cell lysates were analyzed by immunoblotting. The phosphorylation of both serine 2 and serine 5 at the C-terminal domain of RNA polymerase II is inhibited after treatment with the compounds.

C-terminus of the largest subunit of RNA Pol II is an important regulatory domain referred to as CTD (C-terminal domain) phosphorylated specifically by CDK9. We therefore investigated the effect of the compounds on CTD serine 2 and serine 5 phosphorylation. The levels of both serine 2 and serine 5 phosphorylation in roscovitine or compound 128 treated MCF-7 cells were substantially reduced under all experimental conditions tested (FIG. 3). In sum, the functions of CDKs and RNA polymerase II were suppressed. These observations support the contention that the mechanism of action of the compounds is connected with transcriptional control.

Example 7

Induction of Tumour Supressor p53 in Cancer Cells

Stronger anticancer activity of the compounds is enhanced by its positive impact on stability and activity of the tumour suppressor p53, caused probably via inhibition of CDK2, 7 and 9. Protein p53, accumulated in nuclei upon treatment by the compounds, then leads to trans-activation of natural cell cycle inhibitor p21$^{WAF1}$, further blocking the cell cycle. To measure p53-dependent transcriptional activity, β-galactosidase activity will be quantified in the melanoma cell line Arn8, which had been established using stable transfection of the A375 cell line with a p53-responsive reporter construct pRGCΔfoslacZ (Frebung et al., Cancer Res., 52, 1992-6976). This allows qualitative as well as quantitative measurement of CDK inhibitors-induced p53 transcriptional activity via β-galactosidase assay. Then, the effect will be verified in treated cells by immunoblotting of proteins expressed under the control of p53. β-galactosidase activity of human melanoma cell line Arn8 was determined as described. Briefly, for the determination of total β-galactosidase activity, cells were lysed by 3 freeze-thaw cycles in 0.25 M Tris pH 7.5, and lysates were assayed as described by Sambrook et al. (Mol. Cloning, New York, 1989). Alternatively, β-galactosidase activity was quantified by measuring fluorescence of methylumbelliferyl-β-D-galactopyranoside cleavage product. Cell lines established from the human breast carcinoma (MCF-7) and the human melanoma (Arn8) cell lines were cultured in Dubecco's Modified Eagle Medium (DMEM) supplemented with 10% foetal bovine serum.

For immunoblotting, cell were detached with rubber policeman and washed three times with ice-cold PBS and lysed in buffer (50 mM Tris, pH 7.4, 250 mM NaCl, 5 mM EDTA, 50 mM NaF, 1 mM $Na_3VO_4$, 1% Nonidet P40) containing mixture of protease and phosphatase inhibitors (Sigma-Aldrich, USA). 20 µg of total proteins were separated by SDS-polyacrylamide gel electrophoresis (SDS-PAGE) and transferred onto nitrocellulose membranes. Membranes were blocked in 5% milk and 0.1% Tween 20 in PBS and probed overnight with specific monoclonal antibodies or rabbit polyclonal sera. Primary antibodies specific for p53 (DO-1, in house), p21$^{WAF1}$ (118, in house), PARP-1 (2C10, Sigma-Aldrich St Louis, Mo., USA), Mcl-1 (S-19, Santa Cruz, USA), all used at 1 µg/ml. All primary antibodies were diluted in PBS containing 5% powdered milk; 0.1% Tween 20. Peroxidase conjugated rabbit anti-mouse immunoglobulin or porcine anti-rabbit immunoglobulin antisera (DAKO, Denmark) were used as the secondary antibodies and visualised with ECL reagents (Amersham-Pharmacia, Little Chalfont, UK).

Measurements of proapoptotic properties of new compounds were based on quantification of activities of caspases. For caspase assays, treated cells were harvested by centrifugations and homogenized in an extraction buffer (10 mM KCl, 5 mM Hepes, 1 mM EDTA, 1 mM EGTA, 0.2% CHAPS, inhibitors of proteases, pH 7.4) on ice for 20 min. The homogenates were clarified by centrifugation at 10,000 g for 20 min at 4° C., the proteins were quantified by the Bradford method and diluted to the same concentration. Lysates were then incubated for 1 h with 100 µM Ac DEVD AMC as substrate (Sigma-Aldrich) in an assay buffer (25 mM PIPES, 2 mM EGTA, 2 mM $MgCl2$, 5 mM DTT, pH 7.3). The fluorescence of the product was measured using a Fluoroskan Ascent microplate reader (Labsystems, Helsinki, Finland) at 346 nm/442 nm (ex/em).

Figure 4:
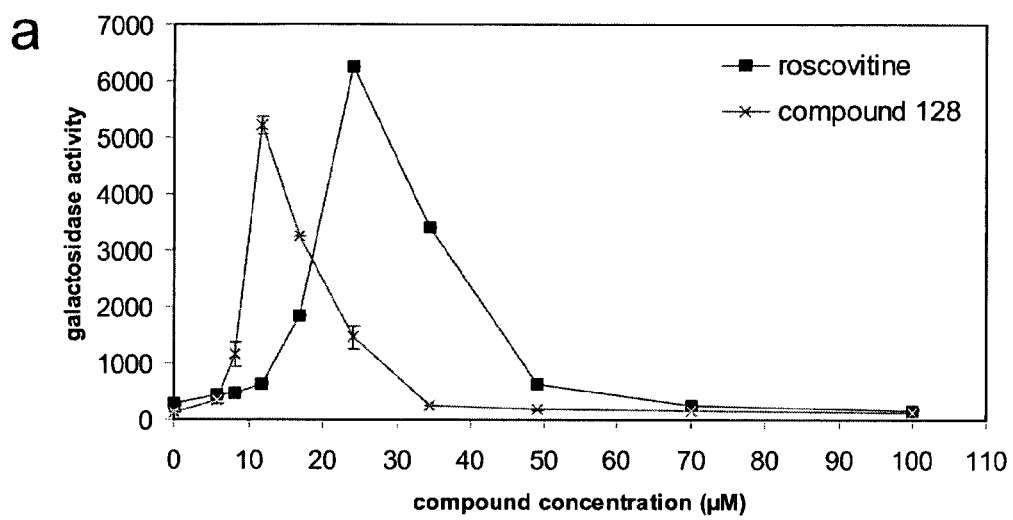
FIG. 4 shows activation of p53-dependent transcription in Ara (the cell line transfected stably with a β-galactosidase reporter gene). Cells were incubated with compound 128 and roscovitine, respectively, and the transcriptional activity of p53 was detected by fluorimetry as a β-galactosidase reporter activity on fluorogenic substrate (a). Formaldehyde-fixed Arn8 cells treated with compound 128 show blue signal on a microphotograph due to X-gal cleavage (b), while untreated cells remain unstained (c). Both compounds proved to activate p53-dependent transcription in Arn8 reporter cell line.
Figure 4:
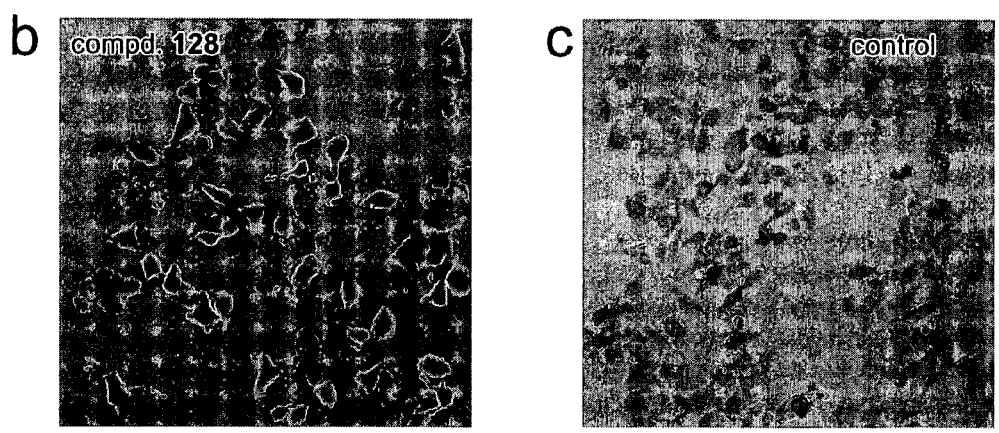

Effects of prepared compounds on activation of p53 protein were analysed in human melanoma cell line Arn8. Induction of wt p53 in these cells treated with 5 μM compound 128 leads to activation of responsive promoter and consequently to expression of β-galactosidase. The total β-galactosidase activity in Arn8 cells was quantified using a fluorimetric assay. The results show strong activity of β-galactosidase at periods of time 12 and 24 hours after treatment giving evidence of transcriptionally active p53 protein in comparison with control cells treated with DMSO (typical dose-response curve is illustrated in FIG. 4). Decrease of fluorescence signal (β-galacosidase activity) at higher concentrations of the compounds can be explained by global block of transcription that leads to decreased expression of the reporter gene. The activity of p53-dependent transcription in Arn8 cells was also checked by a colorimetric assay; typical green-blue signal of cleaved X-gal in treated cells is documented on microphotographs shown in FIG. 4b.

Figure 5:
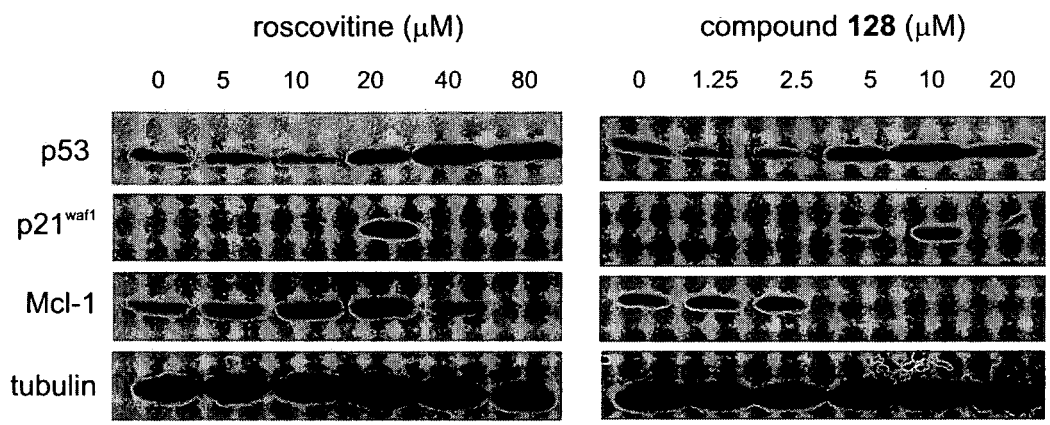
FIG. 5 shows accumulation of tumor suppressor protein p53, expression of p53-regulated CDK inhibitor p21$^{Waf1}$ and downregulation of antiapoptotic protein Mcl-1 in breast carcinoma cell line MCF7 after treatment with compound 128 and roscovitine. The cells were treated for 24 h in a concentration dependent manner with the compounds, harvested and whole cell lysates were prepared. The expression of cell cycle regulators and proteins involved in apoptosis were detected by immunoblotting.
Figure 6:
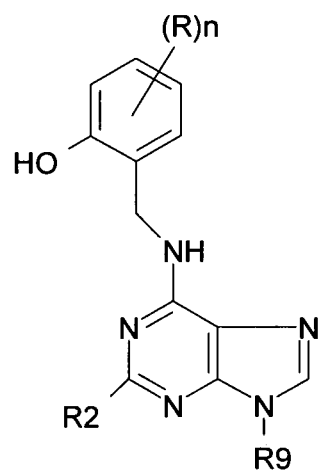
FIG. 6 shows the general formula I.

This transcription activity was also proved by analysing p53 and p21$^{WAF1}$ expression in MCF-7 cells. The induction of p53 protein was apparent in 4 hrs but enhanced level of p21$^{WAF1}$ protein was observed only 12 hours after treatment with compound 128 (FIG. 5). The periods of time 12 and 24 hrs were chosen, since the level of protein expression reached a steady state.

Most of the tested compounds had comparable effects but the concentrations of the tested compound inducing maximum of β-galactosidase activity differed from each to another. These results are presented in Table 15 as concentration inducing maximum of β-galactosidase activity. In summary, it has been documented that the compounds are powerful inducers of p53 expression and activation in cells bearing wild type of TP53 gene.

We analysed also the expression of p53 protein in other cell lines, including BT549 (mut p53) and BT474 (mut p53) breast cancer cell lines, HT29 (mut p53) colorectal cancer cell line, osteosarcoma cell line HOS (mut p53) and RPMI8226 multiple myeloma (mut p53). Importantly, no induction of p53 was observed following exposure of cell lines expressing mutant p53. Moreover, no strong correlation was observed between the sensitivity of cell lines to the compounds and the presence of wild-type or mutant p53.

Then, we also determined effect of the compounds on the cell lines expressing some temperature-sensitive mutants of p53. For example, in BT474 and RPMI-8226 cells bearing temperature-sensitive mutant of p53 (E285K), p53 protein switches between mutant and wild-type conformation in a temperature-dependent manner. At restrictive (37° C.) temperature mutated p53 protein is expressed, while after shift to a permissive (30° C.) temperature p53 is folded correctly and functional. To analyze the functional involvement of p53 in the efficiency of the treatment with the compounds, we cultivated RPMI-8226 cells independently at two different temperatures (restrictive or permissive), and exposed them to increasing doses of selected compounds. The cell lysates were prepared and the levels of cell cycle regulators were analysed by immunoblotting. Compound 128 caused accumulation of wild-type p53 protein in cells maintained at permissive temperature, but did not change the levels of mutant p53 in cells cultivated at restrictive temperature. This indicates that the compound 128 promote stabilization of wild-type p53 protein. Moreover, the monitoring of the expression of p53 targets such as p21$^{waf1}$ and MDM2 revealed their appearance following treatment with CDK inhibitors solely in cells maintained at permissive temperature, but not in cells kept at restrictive temperature.

Remarkably, cells under permissive conditions underwent apoptosis at even lower concentrations of compound 128 and roscovitine. We have observed fragmentation of PARP-1 to occur in cells treated with about two-fold lower drug concentrations that in cells kept in restrictive temperature. Similarly, expression of anti-apoptotic protein Mcl-1 was also suppressed more efficiently at 30° C. by both compounds. Also activities of caspases-3/7 extracted from cells kept under different conditions significantly differed, i.e. they were higher in lysates prepared from cells kept at 30° C. These data evidence that wild-type p53 protein expressed in RPMI-8226 cells cultured at permissive temperature facilitates induction of apoptosis upon treatment with the compounds.

TABLE 12

The effect of selected substituted 6-(2-hydroxybenzylamino)purine derivatives on induction of p53 protein in Arn8 cells stable transfected with a β-galactosidase reporter gene (++ very strong, + weak, − no effect).

| | PURINE SUBSTITUENT | | | p53 (effect/peak concentration in |
| No | R6 | R2 | R9 | μM) |
| --- | --- | --- | --- | --- |
| ROSC | benzylamino | (1-hydroxymethylpropyl)amino | isopropyl | ++/23.0 |
| OCII | 2-hydroxybenzylamino | (1-hydroxymethylpropyl)amino | isopropyl | ++/12.0 |
| 79 | 2-hydroxy-5-chlorobenzylamino | (1-hydroxymethylpropyl)amino | isopropyl | ++/8.0 |
| 89 | 2-hydroxy-5-fluorobenzylamino | (1-hydroxymethylpropyl)amino | isopropyl | ++/6.0 |
| 107 | 2-hydroxy-5-methylbenzylamino | (1-hydroxymethylpropyl)amino | isopropyl | ++/6.0 |
| 114 | 2,3-dihydroxybenzylamino | (1-hydroxymethylpropyl)amino | isopropyl | ++/12.0 |
| 119 | 2,4-dihydroxybenzylamino | (1-hydroxymethylpropyl)amino | isopropyl | +/12.0 |
| 123 | 2,5-dihydroxybenzylamino | (1-hydroxymethylpropyl)amino | isopropyl | +/11.0 |
| 125 | 2-hydroxy-3-methoxybenzylamino | 2-aminocyclohexylamino | isopropyl | ++/10.0 |
| 126 | 2-hydroxy-3-methoxybenzylamino | 4-aminocyclohexylamino | isopropyl | ++/11.0 |
| 128 | 2-hydroxy-3-methoxybenzylamino | (1-hydroxymethylpropyl)amino | isopropyl | ++/8.0 |

Example 8

In Vivo Anticancer Activity

Screening of biological activity of compound 128 was performed on survival model of P388D1 leukemia transplanted intraperitoneally with 2.10$^5$ cells. DBA-2 mice were used as a host. One day following the leukemia transplantation, treatment with 128 was initiated. The drug was given orally by gastric gavages in total volume of 200 μl/dose twice daily at dose 250 mg/kg in two chemotherapy cycles (Days 1-3 and 7-9). The compound 128 was solubilized in 5% N-methyl-2-pyrollidine, 30% polyethylene glycol 400, 65% tartar buffer (pH 3.0). Survival analysis of treated animals (10 mice/group) was preformed in comparison with vehicle treated mice using Kaplan-Meier method and the significance was evaluated by the log-rank test. Body weight of experimental animals was evaluated in parallel in order to reflect toxicity and efficacy of therapy. Comparative analysis of body weight was performed using non-parametric t-test.

Results of our analysis demonstrated that compound 128 is reducing body weight of treated animals, which is in the model of intraperitoneally transplanted P388D1 leukemia indicative for both toxicity and efficacy of the treatment (reduction of ascites and intraperitoneal tumor formation).

Survival analysis demonstrated significantly better survival of mice treated with 128 (P=0.0427) that has been translated to longer mean survival time (27.4 days for drug treated group versus 13.2 days for vehicle treated group).

More detailed analysis of anticancer activity of compound 128 was performed on human xenograft model of A549 lung adenocarcinoma transplanted to CD-1 SCID mice. Animals were transplanted subcutaneously with $2.10^6$ A549 cells into lower back. Approximately one month later, majority of animals developed palpable tumors and therapy was initiated. The drug was given orally by gastric gavages in total volume of 200 μl/dose twice daily at dose 150 mg/kg in two chemotherapy cycles (Days 1-3 and 7-9). The compound 128 was solubilized in 5% N-methyl-2-pyrollidine, 30% polyethylene glycol 400, 65% tartar buffer (pH 3.0). Primary endpoint for analysis was reduction of tumor volume (10 mice/group), which was quantified by caliperation. Analysis of treated animals was preformed in comparison with vehicle treated mice. Body weight of experimental animals was also evaluated in parallel in order to reflect toxicity of the therapy. Comparative analysis of tumor volumes and body weights was performed using non-parametric t-test.

Results of our analysis demonstrated that compound 128 has good tolerability. There was only slight reduction the body weight of treated animals, which was however significant in one time point (Day 52) only.

Tumor volume analysis showed significantly smaller tumors in mice treated with 128 (P=0.0506) that has been translated to longer mean survival time (39.1 days for drug treated group versus 13.2 days for vehicle treated group).

Example 9

Dry Capsules 5000 capsules, each of which contains 0.25 g of a compound of the formula I as an active ingredient, are prepared as follows:
Composition

| Active ingredient | 1250 g |
| Talc | 180 g |
| Wheat starch | 120 g |
| Magnesium stearate | 80 g |
| Lactose | 20 g |

Preparation Process:

The powdered substances mentioned are pressed through a sieve of mesh width 0.6 mm. Portions of 0.33 g of the mixture are transferred to gelatine capsules with the aid of a capsule-filling machine.

Example 10

Soft Capsules 5000 soft gelatine capsules, each of which contains 0.05 g of a compound of the formula I as an active ingredient, are prepared as follows:
Composition

| Active ingredient | 250 g |
| Lauroglycol | 2 liters |

Preparation Process:

The powdered active ingredient is suspended in Lauroglykol® (propylene glycol laurate, Gattefossé S. A., Saint Priest, France) and ground in a wet-pulveriser to a particle size of about 1 to 3 μm. Portions of in each case 0.419 g of the mixture are then transferred to soft gelatine capsules by means of a capsule-filling machine.

Example 11

Soft Capsules 5000 soft gelatine capsules, each of which contains 0.05 g of a compound of the formula I as an active ingredient, are prepared as follows:
Composition

| Active ingredient | 250 g |
| PEG 400 | 1 liter |
| Tween 80 | 1 liter |

Preparation Process:

The powdered active ingredient is suspended in PEG 400 (polyethylene glycol of Mr between 380 and about 420, Sigma, Fluka, Aldrich, USA) and Tween® 80 (polyoxyethylene sorbitan monolaurate, Atlas Chem. Inc., Inc., USA, supplied by Sigma, Fluka, Aldrich, USA) and ground in a wet-pulveriser to a particle size of about 1 to 3 mm. Portions of in each case 0.43 g of the mixture are then transferred to soft gelatine capsules by means of a capsule-filling machine.

The invention claimed is:
1. A compound of formula I

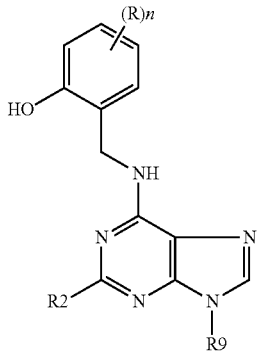

wherein
(R)n represents n substituents R, which can be the same or different, the substituents R being selected from the group consisting of alkyl, alkoxy, amino, halogen, mercapto and nitro, wherein n is from 1 to 4, and
R2 is R2'—NH— wherein
R2' is selected from the group consisting of alkyl, alkenyl, cycloalkyl, and cycloalkyl alkyl, wherein each of the groups can optionally be substituted by one or more substituents selected from the group consisting of amino, hydroxy, mercapto, and alkoxy, and
R9 is selected from the group consisting of alkyl, alkenyl, cycloalkyl, cycloalkyl alkyl, aryl and arylalkyl group,
or a pharmaceutically acceptable salt thereof.

2. A pharmaceutical composition comprising a compound according to claim 1 and a pharmaceutically acceptable carrier.

3. The pharmaceutical composition of claim 2, characterized in that it further contains at least one additional anti-tumour agent.

4. The pharmaceutical composition of claim 3, wherein the additional anti-tumor agent is selected from mitoxantrone and cis-platinum.

5. The compound according to claim 1, the compound being selected from the group consisting of:
2-({6-[(2-hydroxy-5-chlorobenzyl)amino]-9-(methyl)-9H-purin-2-yl}amino)butan-1-ol,
2-({6-[(2-hydroxy-5-chlorobenzyl)amino]-9-(ethyl)-9H-purin-2-yl}amino)butan-1-ol,
2-({6-[(2-hydroxy-5-chlorobenzyl)amino]-9-(isopropyl)-9H-purin-2-yl}amino)butan-1-ol,
2-({6-[(2-hydroxy-5-chlorobenzyl)amino]-9-(3-pentyl)-9H-purin-2-yl}amino)butan-1-ol,
2-({6-[(2-hydroxy-5-chlorobenzyl)amino]-9-(cyclohexyl)-9H-purin-2-yl}amino)butan-1-ol,
2-({6-[(2-hydroxy-5-chlorobenzyl)amino]-9-(benzyl)-9H-purin-2-yl}amino)butan-1-ol,
N6-(2-hydroxy-5-chlorobenzyl)-N2-(2-aminopropyl)-9-(methyl)-9H-purin-2,6-diamine,
N6-(2-hydroxy-5-chlorobenzyl)-N2-(2-aminopropyl)-9-(ethyl)-9H-purin-2,6-diamine,
N6-(2-hydroxy-5-chlorobenzyl)-N2-(2-aminopropyl)-9-(isopropyl)-9H-purin-2,6-diamine,
N6-(2-hydroxy-5-chlorobenzyl)-N2-(2-aminopropyl)-9-(3-pentyl)-9H-purin-2,6-diamine,
N6-(2-hydroxy-5-chlorobenzyl)-N2-(2-aminopropyl)-9-(cyclohexyl)-9H-purin-2,6-diamine,
N6-(2-hydroxy-5-chlorobenzyl)-N2-(2-aminopropyl)-9-(benzyl)-9H-purin-2,6-diamine,
2-({6-[(2-hydroxy-5-chlorobenzyl)amino]-9-(methyl)-9H-purin-2-yl}amino)-3-methyl-butan-1-ol,
2-({6-[(2-hydroxy-5-chlorobenzyl)amino]-9-(ethyl)-9H-purin-2-yl}amino)-3-methyl-butan-1-ol,
2-({6-[(2-hydroxy-5-chlorobenzyl)amino]-9-(isopropyl)-9H-purin-2-yl}amino)-3-methyl-butan-1-ol,
2-({6-[(2-hydroxy-5-chlorobenzyl)amino]-9-(3-pentyl)-9H-purin-2-yl}amino)-3-methyl-butan-1-ol,
2-({6-[(2-hydroxy-5-chlorobenzyl)amino]-9-(cyclohexyl)-9H-purin-2-yl}amino)-3-methyl-butan-1-ol,
2-({6-[(2-hydroxy-5-chlorobenzyl)amino]-9-(benzyl)-9H-purin-2-yl}amino)-3-methyl-butan-1-ol,
N6-(2-hydroxy-5-chlorobenzyl)-N2-(4-aminocyclohexyl)-9-(methyl)-9H-purin-2,6-diamine,
N6-(2-hydroxy-5-chlorobenzyl)-N2-(4-aminocyclohexyl)-9-(ethyl)-9H-purin-2,6-diamine,
N6-(2-hydroxy-5-chlorobenzyl)-N2-(4-aminocyclohexyl)-9-(isopropyl)-9H-purin-2,6-diamine,
N6-(2-hydroxy-5-chlorobenzyl)-N2-(4-aminocyclohexyl)-9-(3-pentyl)-9H-purin-2,6-diamine,
N6-(2-hydroxy-5-chlorobenzyl)-N2-(4-aminocyclohexyl)-9-(cyclohexyl)-9H-purin-2,6-diamine,
N6-(2-hydroxy-5-chlorobenzyl)-N2-(4-aminocyclohexyl)-9-(benzyl)-9H-purin-2,6-diamine,
1-({6-[(2-hydroxy-5-chlorobenzyl)amino]-9-(methyl)-9H-purin-2-yl}amino)-2-methyl-propan-2-ol,
1-({6-[(2-hydroxy-5-chlorobenzyl)amino]-9-(ethyl)-9H-purin-2-yl}amino)-2-methyl-propan-2-ol,
1-({6-[(2-hydroxy-5-chlorobenzyl)amino]-9-(isopropyl)-9H-purin-2-yl}amino)-2-methyl-propan-2-ol,
1-({6-[(2-hydroxy-5-chlorobenzyl)amino]-9-(3-pentyl)-9H-purin-2-yl}amino)-2-methyl-propan-2-ol,
1-({6-[(2-hydroxy-5-chlorobenzyl)amino]-9-(cyclohexyl)-9H-purin-2-yl}amino)-2-methyl-propan-2-ol,
1-({6-[(2-hydroxy-5-chlorobenzyl)amino]-9-(benzyl)-9H-purin-2-yl}amino)-2-methyl-propan-2-ol,
3-({6-[(2-hydroxy-5-chlorobenzyl)amino]-9-(methyl)-9H-purin-2-yl}amino)-2-methyl-butan-2-ol,
3-({6-[(2-hydroxy-5-chlorobenzyl)amino]-9-(ethyl)-9H-purin-2-yl}amino)-2-methyl-butan-2-ol,
3-({6-[(2-hydroxy-5-chlorobenzyl)amino]-9-(isopropyl)-9H-purin-2-yl}amino)-2-methyl-butan-2-ol,
3-({6-[(2-hydroxy-5-chlorobenzyl)amino]-9-(3-pentyl)-9H-purin-2-yl}amino)-2-methyl-butan-2-ol,
3-({6-[(2-hydroxy-5-chlorobenzyl)amino]-9-(cyclohexyl)-9H-purin-2-yl}amino)-2-methyl-butan-2-ol,
3-({6-[(2-hydroxy-5-chlorobenzyl)amino]-9-(benzyl)-9H-purin-2-yl}amino)-2-methyl-butan-2-ol,
4-({6-[(2-hydroxy-5-chlorobenzyl)amino]-9-(methyl)-9H-purin-2-yl}amino)-2-methyl-butan-2-ol,
4-({6-[(2-hydroxy-5-chlorobenzyl)amino]-9-(ethyl)-9H-purin-2-yl}amino)-2-methyl-butan-2-ol,
4-({6-[(2-hydroxy-5-chlorobenzyl)amino]-9-(isopropyl)-9H-purin-2-yl}amino)-2-methyl-butan-2-ol,
4-({6-[(2-hydroxy-5-chlorobenzyl)amino]-9-(3-pentyl)-9H-purin-2-yl}amino)-2-methyl-butan-2-ol,
4-({6-[(2-hydroxy-5-chlorobenzyl)amino]-9-(cyclohexyl)-9H-purin-2-yl}amino)-2-methyl-butan-2-ol,
4-({6-[(2-hydroxy-5-chlorobenzyl)amino]-9-(benzyl)-9H-purin-2-yl}amino)-2-methyl-butan-2-ol,
4-({6-[(2-hydroxy-5-chlorobenzyl)amino]-9-(methyl)-9H-purin-2-yl}amino)-2-methyl-pentan-2-ol,
4-({6-[(2-hydroxy-5-chlorobenzyl)amino]-9-(ethyl)-9H-purin-2-yl}amino)-2-methyl-pentan-2-ol, 4-({6-[(2-hydroxy-5-chlorobenzyl)amino]-9-(isopropyl)-9H-purin-2-yl}amino)-2-methyl-pentan-2-ol,
4-({6-[(2-hydroxy-5-chlorobenzyl)amino]-9-(3-pentyl)-9H-purin-2-yl}amino)-2-methyl-pentan-2-ol,
4-({6-[(2-hydroxy-5-chlorobenzyl)amino]-9-(cyclohexyl)-9H-purin-2-yl}amino)-2-methyl-pentan-2-ol,
4-({6-[(2-hydroxy-5-chlorobenzyl)amino]-9-(benzyl)-9H-purin-2-yl}amino)-2-methyl-pentan-2-ol,
1-({6-[(2-hydroxy-5-chlorobenzyl)amino]-9-(methyl)-9H-purin-2-yl}amino)propan-2-ol,
1-({6-[(2-hydroxy-5-chlorobenzyl)amino]-9-(ethyl)-9H-purin-2-yl}amino)propan-2-ol,
1-({6-[(2-hydroxy-5-chlorobenzyl)amino]-9-(isopropyl)-9H-purin-2-yl}amino)propan-2-ol,
1-({6-[(2-hydroxy-5-chlorobenzyl)amino]-9-(3-pentyl)-9H-purin-2-yl}amino)propan-2-ol,
1-({6-[(2-hydroxy-5-chlorobenzyl)amino]-9-(cyclohexyl)-9H-purin-2-yl}amino)propan-2-ol,
1-({6-[(2-hydroxy-5-chlorobenzyl)amino]-9-(benzyl)-9H-purin-2-yl}amino)propan-2-ol,
4-({6-[(2-hydroxy-5-chlorobenzyl)amino]-9-(methyl)-9H-purin-2-yl}amino)-2,3-dimethyl-butan-2-ol,
4-({6-[(2-hydroxy-5-chlorobenzyl)amino]-9-(ethyl)-9H-purin-2-yl}amino)-2,3-dimethyl-butan-2-ol,
4-({6-[(2-hydroxy-5-chlorobenzyl)amino]-9-(isopropyl)-9H-purin-2-yl}amino)-2,3-dimethyl-butan-2-ol,
4-({6-[(2-hydroxy-5-chlorobenzyl)amino]-9-(3-pentyl)-9H-purin-2-yl}amino)-2,3-dimethyl-butan-2-ol,
4-({6-[(2-hydroxy-5-chlorobenzyl)amino]-9-(cyclohexyl)-9H-purin-2-yl}amino)-2,3-dimethyl-butan-2-ol,
4-({6-[(2-hydroxy-5-chlorobenzyl)amino]-9-(benzyl)-9H-purin-2-yl}amino)-2,3-dimethyl-butan-2-ol,
3-({6-[(2-hydroxy-5-chlorobenzyl)amino]-9-(methyl)-9H-purin-2-yl}amino)-2-methyl-pentan-2-ol,
3-({6-[(2-hydroxy-5-chlorobenzyl)amino]-9-(ethyl)-9H-purin-2-yl}amino)-2-methyl-pentan-2-ol,
3-({6-[(2-hydroxy-5-chlorobenzyl)amino]-9-(isopropyl)-9H-purin-2-yl}amino)-2-methyl-pentan-2-ol,
3-({6-[(2-hydroxy-5-chlorobenzyl)amino]-9-(3-pentyl)-9H-purin-2-yl}amino)-2-methyl-pentan-2-ol,
3-({6-[(2-hydroxy-5-chlorobenzyl)amino]-9-(cyclohexyl)-9H-purin-2-yl}amino)-2-methyl-pentan-2-ol,
3-({6-[(2-hydroxy-5-chlorobenzyl)amino]-9-(benzyl)-9H-purin-2-yl}amino)-2-methyl-pentan-2-ol,
3-({6-[(2-hydroxy-5-chlorobenzyl)amino]-9-(methyl)-9H-purin-2-yl]amino}pentan-2-ol,
3-({6-[(2-hydroxy-5-chlorobenzyl)amino]-9-(ethyl)-9H-purin-2-yl]amino}pentan-2-ol,
3-({6-[(2-hydroxy-5-chlorobenzyl)amino]-9-(isopropyl)-9H-purin-2-yl]amino}pentan-2-ol,
3-({6-[(2-hydroxy-5-chlorobenzyl)amino]-9-(3-pentyl)-9H-purin-2-yl]amino}pentan-2-ol,
3-({6-[(2-hydroxy-5-chlorobenzyl)amino]-9-(cyclohexyl)-9H-purin-2-yl]amino}pentan-2-ol,
3-({6-[(2-hydroxy-5-chlorobenzyl)amino]-9-(benzyl)-9H-purin-2-yl]amino}pentan-2-ol,
1-({6-[(2-hydroxy-5-chlorobenzyl)amino]-9-(methyl)-9H-purin-2-yl}amino)-2-methyl-propan-2-ol,
1-({6-[(2-hydroxy-5-chlorobenzyl)amino]-9-(ethyl)-9H-purin-2-yl}amino)-2-methyl-propan-2-ol,
1-({6-[(2-hydroxy-5-chlorobenzyl)amino]-9-(isopropyl)-9H-purin-2-yl}amino)-2-methyl-propan-2-ol,
1-({6-[(2-hydroxy-5-chlorobenzyl)amino]-9-(3-pentyl)-9H-purin-2-yl}amino)-2-methyl-propan-2-ol,
1-({6-[(2-hydroxy-5-chlorobenzyl)amino]-9-(cyclohexyl)-9H-purin-2-yl}amino)-2-methyl-propan-2-ol,
1-({6-[(2-hydroxy-5-chlorobenzyl)amino]-9-(benzyl)-9H-purin-2-yl}amino)-2-methyl-propan-2-ol,
2-({6-[(2-hydroxy-3-chlorobenzyl)amino]-9-(methyl)-9H-purin-2-yl}amino)butan-1-ol,
2-({6-[(2-hydroxy-3-chlorobenzyl)amino]-9-(ethyl)-9H-purin-2-yl}amino)butan-1-ol,
2-({6-[(2-hydroxy-3-chlorobenzyl)amino]-9-(isopropyl)-9H-purin-2-yl}amino)butan-1-ol,
2-({6-[(2-hydroxy-3-chlorobenzyl)amino]-9-(3-pentyl)-9H-purin-2-yl}amino)butan-1-ol,
2-({6-[(2-hydroxy-3-chlorobenzyl)amino]-9-(cyclohexyl)-9H-purin-2-yl}amino)butan-1-ol,
2-({6-[(2-hydroxy-3-chlorobenzyl)amino]-9-(benzyl)-9H-purin-2-yl}amino)butan-1-ol,
N6-(2-hydroxy-3-chlorobenzyl)-N2-(2-aminopropyl)-9-(methyl)-9H-purin-2,6-diamine,
N6-(2-hydroxy-3-chlorobenzyl)-N2-(2-aminopropyl)-9-(ethyl)-9H-purin-2,6-diamine,
N6-(2-hydroxy-3-chlorobenzyl)-N2-(2-aminopropyl)-9-(isopropyl)-9H-purin-2,6-diamine,
N6-(2-hydroxy-3-chlorobenzyl)-N2-(2-aminopropyl)-9-(3-pentyl)-9H-purin-2,6-diamine,
N6-(2-hydroxy-3-chlorobenzyl)-N2-(2-aminopropyl)-9-(cyclohexyl)-9H-purin-2,6-diamine,
N6-(2-hydroxy-3-chlorobenzyl)-N2-(2-aminopropyl)-9-(benzyl)-9H-purin-2,6-diamine,
2-({6-[(2-hydroxy-3-chlorobenzyl)amino]-9-(methyl)-9H-purin-2-yl}amino)-3-methyl-butan-1-ol,
2-({6-[(2-hydroxy-3-chlorobenzyl)amino]-9-(ethyl)-9H-purin-2-yl}amino)-3-methyl-butan-1-ol,
2-({6-[(2-hydroxy-3-chlorobenzyl)amino]-9-(isopropyl)-9H-purin-2-yl}amino)-3-methyl-butan-1-ol,
2-({6-[(2-hydroxy-3-chlorobenzyl)amino]-9-(3-pentyl)-9H-purin-2-yl}amino)-3-methyl-butan-1-ol,
2-({6-[(2-hydroxy-3-chlorobenzyl)amino]-9-(cyclohexyl)-9H-purin-2-yl}amino)-3-methyl-butan-1-ol,
2-({6-[(2-hydroxy-3-chlorobenzyl)amino]-9-(benzyl)-9H-purin-2-yl}amino)-3-methyl-butan-1-ol,
N6-(2-hydroxy-3-chlorobenzyl)-N2-(4-aminocyclohexyl)-9-(methyl)-9H-purin-2,6-diamine,
N6-(2-hydroxy-3-chlorobenzyl)-N2-(4-aminocyclohexyl)-9-(ethyl)-9H-purin-2,6-diamine,
N6-(2-hydroxy-3-chlorobenzyl)-N2-(4-aminocyclohexyl)-9-(isopropyl)-9H-purin-2,6-diamine,
N6-(2-hydroxy-3-chlorobenzyl)-N2-(4-aminocyclohexyl)-9-(3-pentyl)-9H-purin-2,6-diamine,
N6-(2-hydroxy-3-chlorobenzyl)-N2-(4-aminocyclohexyl)-9-(cyclohexyl)-9H-purin-2,6-diamine,
N6-(2-hydroxy-3-chlorobenzyl)-N2-(4-aminocyclohexyl)-9-(benzyl)-9H-purin-2,6-diamine,
1-({6-[(2-hydroxy-3-chlorobenzyl)amino]-9-(methyl)-9H-purin-2-yl}amino)propan-2-ol,
1-({6-[(2-hydroxy-3-chlorobenzyl)amino]-9-(ethyl)-9H-purin-2-yl}amino)propan-2-ol,
1-({6-[(2-hydroxy-3-chlorobenzyl)amino]-9-(isopropyl)-9H-purin-2-yl}amino)propan-2-ol,
1-({6-[(2-hydroxy-3-chlorobenzyl)amino]-9-(3-pentyl)-9H-purin-2-yl}amino)propan-2-ol,
1-({6-[(2-hydroxy-3-chlorobenzyl)amino]-9-(cyclohexyl)-9H-purin-2-yl}amino)propan-2-ol,
1-({6-[(2-hydroxy-3-chlorobenzyl)amino]-9-(benzyl)-9H-purin-2-yl}amino)propan-2-ol,
1-({6-[(2-hydroxy-3-chlorobenzyl)amino]-9-(methyl)-9H-purin-2-yl}amino)-2-methyl-propan-2-ol,
1-({6-[(2-hydroxy-3-chlorobenzyl)amino]-9-(ethyl)-9H-purin-2-yl}amino)-2-methyl-propan-2-ol, 1-({6-[(2-hydroxy-3-chlorobenzyl)amino]-9-(isopropyl)-9H-purin-2-yl}amino)-2-methyl-propan-2-ol,
1-({6-[(2-hydroxy-3-chlorobenzyl)amino]-9-(3-pentyl)-9H-purin-2-yl}amino)-2-methyl-propan-2-ol,
1-({6-[(2-hydroxy-3-chlorobenzyl)amino]-9-(cyclohexyl)-9H-purin-2-yl}amino)-2-methyl-propan-2-ol,
1-({6-[(2-hydroxy-3-chlorobenzyl)amino]-9-(benzyl)-9H-purin-2-yl}amino)-2-methyl-propan-2-ol,
3-({6-[(2-hydroxy-3-chlorobenzyl)amino]-9-(methyl)-9H-purin-2-yl}amino)-2-methyl-butan-2-ol,
3-({6-[(2-hydroxy-3-chlorobenzyl)amino]-9-(ethyl)-9H-purin-2-yl}amino)-2-methyl-butan-2-ol,
3-({6-[(2-hydroxy-3-chlorobenzyl)amino]-9-(isopropyl)-9H-purin-2-yl}amino)-2-methyl-butan-2-ol,
3-({6-[(2-hydroxy-3-chlorobenzyl)amino]-9-(3-pentyl)-9H-purin-2-yl}amino)-2-methyl-butan-2-ol,
3-({6-[(2-hydroxy-3-chlorobenzyl)amino]-9-(cyclohexyl)-9H-purin-2-yl}amino)-2-methyl-butan-2-ol,
3-({6-[(2-hydroxy-3-chlorobenzyl)amino]-9-(benzyl)-9H-purin-2-yl}amino)-2-methyl-butan-2-ol,
4-({6-[(2-hydroxy-3-chlorobenzyl)amino]-9-(methyl)-9H-purin-2-yl}amino)-2-methyl-butan-2-ol,
4-({6-[(2-hydroxy-3-chlorobenzyl)amino]-9-(ethyl)-9H-purin-2-yl}amino)-2-methyl-butan-2-ol,
4-({6-[(2-hydroxy-3-chlorobenzyl)amino]-9-(isopropyl)-9H-purin-2-yl}amino)-2-methyl-butan-2-ol,
4-({6-[(2-hydroxy-3-chlorobenzyl)amino]-9-(3-pentyl)-9H-purin-2-yl}amino)-2-methyl-butan-2-ol,
4-({6-[(2-hydroxy-3-chlorobenzyl)amino]-9-(cyclohexyl)-9H-purin-2-yl}amino)-2-methyl-butan-2-ol,
4-({6-[(2-hydroxy-3-chlorobenzyl)amino]-9-(benzyl)-9H-purin-2-yl}amino)-2-methyl-butan-2-ol,
4-({6-[(2-hydroxy-3-chlorobenzyl)amino]-9-(methyl)-9H-purin-2-yl}amino)-2-methyl-pentan-2-ol,
4-({6-[(2-hydroxy-3-chlorobenzyl)amino]-9-(ethyl)-9H-purin-2-yl}amino)-2-methyl-pentan-2-ol,
4-({6-[(2-hydroxy-3-chlorobenzyl)amino]-9-(isopropyl)-9H-purin-2-yl}amino)-2-methyl-pentan-2-ol,
4-({6-[(2-hydroxy-3-chlorobenzyl)amino]-9-(3-pentyl)-9H-purin-2-yl}amino)-2-methyl-pentan-2-ol,
4-({6-[(2-hydroxy-3-chlorobenzyl)amino]-9-(cyklohexyl)-9H-purin-2-yl}amino)-2-methyl-pentan-2-ol,
4-({6-[(2-hydroxy-3-chlorobenzyl)amino]-9-(benzyl)-9H-purin-2-yl}amino)-2-methyl-pentan-2-ol,
4-({6-[(2-hydroxy-3-chlorobenzyl)amino]-9-(methyl)-9H-purin-2-yl}amino)-2,3-dimethyl-butan-2-ol,
4-({6-[(2-hydroxy-3-chlorobenzyl)amino]-9-(ethyl)-9H-purin-2-yl}amino)-2,3-dimethyl-butan-2-ol,
4-({6-[(2-hydroxy-3-chlorobenzyl)amino]-9-(isopropyl)-9H-purin-2-yl}amino)-2,3-dimethyl-butan-2-ol,
4-({6-[(2-hydroxy-3-chlorobenzyl)amino]-9-(3-pentyl)-9H-purin-2-yl}amino)-2,3-dimethyl-butan-2-ol,
4-({6-[(2-hydroxy-3-chlorobenzyl)amino]-9-(cyklohexyl)-9H-purin-2-yl}amino)-2,3-dimethyl-butan-2-ol,
4-({6-[(2-hydroxy-3-chlorobenzyl)amino]-9-(benzyl)-9H-purin-2-yl}amino)-2,3-dimethyl-butan-2-ol,
3-({6-[(2-hydroxy-3-chlorobenzyl)amino]-9-(methyl)-9H-purin-2-yl}amino)-2-methyl-pentan-2-ol,
3-({6-[(2-hydroxy-3-chlorobenzyl)amino]-9-(ethyl)-9H-purin-2-yl}amino)-2-methyl-pentan-2-ol,
3-({6-[(2-hydroxy-3-chlorobenzyl)amino]-9-(isopropyl)-9H-purin-2-yl}amino)-2-methyl-pentan-2-ol,
3-({6-[(2-hydroxy-3-chlorobenzyl)amino]-9-(3-pentyl)-9H-purin-2-yl}amino)-2-methyl-pentan-2-ol,
3-({6-[(2-hydroxy-3-chlorobenzyl)amino]-9-(cyclohexyl)-9H-purin-2-yl}amino)-2-methyl-pentan-2-ol,
3-({6-[(2-hydroxy-3-chlorobenzyl)amino]-9-(benzyl)-9H-purin-2-yl}amino)-2-methyl-pentan-2-ol,
3-({6-[(2-hydroxy-3-chlorobenzyl)amino]-9-(methyl)-9H-purin-2-yl]amino}pentan-2-ol,
3-({6-[(2-hydroxy-3-chlorobenzyl)amino]-9-(ethyl)-9H-purin-2-yl]amino}pentan-2-ol,
3-({6-[(2-hydroxy-3-chlorobenzyl)amino]-9-(isopropyl)-9H-purin-2-yl]amino}pentan-2-ol,
3-({6-[(2-hydroxy-3-chlorobenzyl)amino]-9-(3-pentyl)-9H-purin-2-yl]amino}pentan-2-ol,
3-({6-[(2-hydroxy-3-chlorobenzyl)amino]-9-(cyklohexyl)-9H-purin-2-yl]amino}pentan-2-ol,
3-({6-[(2-hydroxy-3-chlorobenzyl)amino]-9-(benzyl)-9H-purin-2-yl]amino}pentan-2-ol,
1-({6-[(2-hydroxy-3-chlorobenzyl)amino]-9-(methyl)-9H-purin-2-yl}amino)-2-methyl-propan-2-ol,
1-({6-[(2-hydroxy-3-chlorobenzyl)amino]-9-(ethyl)-9H-purin-2-yl}amino)-2-methyl-propan-2-ol,
1-({6-[(2-hydroxy-3-chlorobenzyl)amino]-9-(isopropyl)-9H-purin-2-yl}amino)-2-methyl-propan-2-ol,
1-({6-[(2-hydroxy-3-chlorobenzyl)amino]-9-(3-pentyl)-9H-purin-2-yl}amino)-2-methyl-propan-2-ol,
1-({6-[(2-hydroxy-3-chlorobenzyl)amino]-9-(cyklohexyl)-9H-purin-2-yl}amino)-2-methyl-propan-2-ol,
1-({6-[(2-hydroxy-3-chlorobenzyl)amino]-9-(benzyl)-9H-purin-2-yl}amino)-2-methyl-propan-2-ol,
2-({6-[(2-hydroxy-5-fluorobenzyl)amino]-9-(methyl)-9H-purin-2-yl}amino)butan-1-ol,
2-({6-[(2-hydroxy-5-fluorobenzyl)amino]-9-(ethyl)-9H-purin-2-yl}amino)butan-1-ol,
2-({6-[(2-hydroxy-5-fluorobenzyl)amino]-9-(isopropyl)-9H-purin-2-yl}amino)butan-1-ol,
2-({6-[(2-hydroxy-5-fluorobenzyl)amino]-9-(3-pentyl)-9H-purin-2-yl}amino)butan-1-ol,
2-({6-[(2-hydroxy-5-fluorobenzyl)amino]-9-(cyklohexyl)-9H-purin-2-yl}amino)butan-1-ol,
2-({6-[(2-hydroxy-5-fluorobenzyl)amino]-9-(benzyl)-9H-purin-2-yl}amino)butan-1-ol,
N6-(2-hydroxy-5-fluorobenzyl)-N2-(2-aminopropyl)-9-(methyl)-9H-purin-2,6-diamine,
N6-(2-hydroxy-5-fluorobenzyl)-N2-(2-aminopropyl)-9-(ethyl)-9H-purin-2,6-diamine,
N6-(2-hydroxy-5-fluorobenzyl)-N2-(2-aminopropyl)-9-(isopropyl)-9H-purin-2,6-diamine,
N6-(2-hydroxy-5-fluorobenzyl)-N2-(2-aminopropyl)-9-(3-pentyl)-9H-purin-2,6-diamine,
N6-(2-hydroxy-5-fluorobenzyl)-N2-(2-aminopropyl)-9-(cyklohexyl)-9H-purin-2,6-diamine,
N6-(2-hydroxy-5-fluorobenzyl)-N2-(2-aminopropyl)-9-(benzyl)-9H-purin-2,6-diamine,
1-({6-[(2-hydroxy-5-fluorobenzyl)amino]-9-(methyl)-9H-purin-2-yl}amino)propan-2-ol,
1-({6-[(2-hydroxy-5-fluorobenzyl)amino]-9-(ethyl)-9H-purin-2-yl}amino)propan-2-ol,
1-({6-[(2-hydroxy-5-fluorobenzyl)amino]-9-(isopropyl)-9H-purin-2-yl}amino)propan-2-ol,
1-({6-[(2-hydroxy-5-fluorobenzyl)amino]-9-(3-pentyl)-9H-purin-2-yl}amino)propan-2-ol,
1-({6-[(2-hydroxy-5-fluorobenzyl)amino]-9-(cyklohexyl)-9H-purin-2-yl}amino)propan-2-ol,
1-({6-[(2-hydroxy-5-fluorobenzyl)amino]-9-(benzyl)-9H-purin-2-yl}amino)propan-2-ol,
2-({6-[(2-hydroxy-5-fluorobenzyl)amino]-9-(methyl)-9H-purin-2-yl}amino)-3-methyl-butan-1-ol,
2-({6-[(2-hydroxy-5-fluorobenzyl)amino]-9-(ethyl)-9H-purin-2-yl}amino)-3-methyl-butan-1-ol, 2-({6-[(2-hydroxy-5-fluorobenzyl)amino]-9-(isopropyl)-9H-purin-2-yl}amino)-3-methyl-butan-1-ol,
2-({6-[(2-hydroxy-5-fluorobenzyl)amino]-9-(3-pentyl)-9H-purin-2-yl}amino)-3-methyl-butan-1-ol,
2-({6-[(2-hydroxy-5-fluorobenzyl)amino]-9-(cyklohexyl)-9H-purin-2-yl}amino)-3-methyl-butan-1-ol,
2-({6-[(2-hydroxy-5-fluorobenzyl)amino]-9-(benzyl)-9H-purin-2-yl}amino)-3-methyl-butan-1-ol,
N6-(2-hydroxy-5-fluorobenzyl)-N2-(4-aminocyclohexyl)-9-(methyl)-9H-purin-2,6-diamine,
N6-(2-hydroxy-5-fluorobenzyl)-N2-(4-aminocyclohexyl)-9-(ethyl)-9H-purin-2,6-diamine,
N6-(2-hydroxy-5-fluorobenzyl)-N2-(4-aminocyclohexyl)-9-(isopropyl)-9H-purin-2,6-diamine,
N6-(2-hydroxy-5-fluorobenzyl)-N2-(4-aminocyclohexyl)-9-(3-pentyl)-9H-purin-2,6-diamine,
N6-(2-hydroxy-5-fluorobenzyl)-N2-(4-aminocyclohexyl)-9-(cyklohexyl)-9H-purin-2,6-diamine,
N6-(2-hydroxy-5-fluorobenzyl)-N2-(4-aminocyclohexyl)-9-(benzyl)-9H-purin-2,6-diamine,
1-({6-[(2-hydroxy-5-fluorobenzyl)amino]-9-(methyl)-9H-purin-2-yl}amino)-2-methyl-propan-2-ol,
1-({6-[(2-hydroxy-5-fluorobenzyl)amino]-9-(ethyl)-9H-purin-2-yl}amino)-2-methyl-propan-2-ol,
1-({6-[(2-hydroxy-5-fluorobenzyl)amino]-9-(isopropyl)-9H-purin-2-yl}amino)-2-methyl-propan-2-ol,
1-({6-[(2-hydroxy-5-fluorobenzyl)amino]-9-(3-pentyl)-9H-purin-2-yl}amino)-2-methyl-propan-2-ol,
1-({6-[(2-hydroxy-5-fluorobenzyl)amino]-9-(cyklohexyl)-9H-purin-2-yl}amino)-2-methyl-propan-2-ol,
1-({6-[(2-hydroxy-5-fluorobenzyl)amino]-9-(benzyl)-9H-purin-2-yl}amino)-2-methyl-propan-2-ol,
3-({6-[(2-hydroxy-5-fluorobenzyl)amino]-9-(methyl)-9H-purin-2-yl}amino)-2-methyl-butan-2-ol,
3-({6-[(2-hydroxy-5-fluorobenzyl)amino]-9-(ethyl)-9H-purin-2-yl}amino)-2-methyl-butan-2-ol,
3-({6-[(2-hydroxy-5-fluorobenzyl)amino]-9-(isopropyl)-9H-purin-2-yl}amino)-2-methyl-butan-2-ol,
3-({6-[(2-hydroxy-5-fluorobenzyl)amino]-9-(3-pentyl)-9H-purin-2-yl}amino)-2-methyl-butan-2-ol,
3-({6-[(2-hydroxy-5-fluorobenzyl)amino]-9-(cyklohexyl)-9H-purin-2-yl}amino)-2-methyl-butan-2-ol,
3-({6-[(2-hydroxy-5-fluorobenzyl)amino]-9-(benzyl)-9H-purin-2-yl}amino)-2-methyl-butan-2-ol,
4-({6-[(2-hydroxy-5-fluorobenzyl)amino]-9-(methyl)-9H-purin-2-yl}amino)-2-methyl-butan-2-ol,
4-({6-[(2-hydroxy-5-fluorobenzyl)amino]-9-(ethyl)-9H-purin-2-yl}amino)-2-methyl-butan-2-ol,
4-({6-[(2-hydroxy-5-fluorobenzyl)amino]-9-(isopropyl)-9H-purin-2-yl}amino)-2-methyl-butan-2-ol,
4-({6-[(2-hydroxy-5-fluorobenzyl)amino]-9-(3-pentyl)-9H-purin-2-yl}amino)-2-methyl-butan-2-ol,
4-({6-[(2-hydroxy-5-fluorobenzyl)amino]-9-(cyklohexyl)-9H-purin-2-yl}amino)-2-methyl-butan-2-ol,
4-({6-[(2-hydroxy-5-fluorobenzyl)amino]-9-(benzyl)-9H-purin-2-yl}amino)-2-methyl-butan-2-ol,
4-({6-[(2-hydroxy-5-fluorobenzyl)amino]-9-(methyl)-9H-purin-2-yl}amino)-2-methyl-pentan-2-ol,
4-({6-[(2-hydroxy-5-fluorobenzyl)amino]-9-(ethyl)-9H-purin-2-yl}amino)-2-methyl-pentan-2-ol,
4-({6-[(2-hydroxy-5-fluorobenzyl)amino]-9-(isopropyl)-9H-purin-2-yl}amino)-2-methyl-pentan-2-ol,
4-({6-[(2-hydroxy-5-fluorobenzyl)amino]-9-(3-pentyl)-9H-purin-2-yl}amino)-2-methyl-pentan-2-ol,
4-({6-[(2-hydroxy-5-fluorobenzyl)amino]-9-(cyklohexyl)-9H-purin-2-yl}amino)-2-methyl-pentan-2-ol,
4-({6-[(2-hydroxy-5-fluorobenzyl)amino]-9-(benzyl)-9H-purin-2-yl}amino)-2-methyl-pentan-2-ol,
4-({6-[(2-hydroxy-5-fluorobenzyl)amino]-9-(methyl)-9H-purin-2-yl}amino)-2,3-dimethyl-butan-2-ol,
4-({6-[(2-hydroxy-5-fluorobenzyl)amino]-9-(ethyl)-9H-purin-2-yl}amino)-2,3-dimethyl-butan-2-ol,
4-({6-[(2-hydroxy-5-fluorobenzyl)amino]-9-(isopropyl)-9H-purin-2-yl}amino)-2,3-dimethyl-butan-2-ol,
4-({6-[(2-hydroxy-5-fluorobenzyl)amino]-9-(3-pentyl)-9H-purin-2-yl}amino)-2,3-dimethyl-butan-2-ol,
4-({6-[(2-hydroxy-5-fluorobenzyl)amino]-9-(cyklohexyl)-9H-purin-2-yl}amino)-2,3-dimethyl-butan-2-ol,
4-({6-[(2-hydroxy-5-fluorobenzyl)amino]-9-(benzyl)-9H-purin-2-yl}amino)-2,3-dimethyl-butan-2-ol,
3-({6-[(2-hydroxy-5-fluorobenzyl)amino]-9-(methyl)-9H-purin-2-yl}amino)-2-methyl-pentan-2-ol,
3-({6-[(2-hydroxy-5-fluorobenzyl)amino]-9-(ethyl)-9H-purin-2-yl}amino)-2-methyl-pentan-2-ol,
3-({6-[(2-hydroxy-5-fluorobenzyl)amino]-9-(isopropyl)-9H-purin-2-yl}amino)-2-methyl-pentan-2-ol,
3-({6-[(2-hydroxy-5-fluorobenzyl)amino]-9-(3-pentyl)-9H-purin-2-yl}amino)-2-methyl-pentan-2-ol,
3-({6-[(2-hydroxy-5-fluorobenzyl)amino]-9-(cyklohexyl)-9H-purin-2-yl}amino)-2-methyl-pentan-2-ol,
3-({6-[(2-hydroxy-5-fluorobenzyl)amino]-9-(benzyl)-9H-purin-2-yl}amino)-2-methyl-pentan-2-ol,
3-({6-[(2-hydroxy-5-fluorobenzyl)amino]-9-(methyl)-9H-purin-2-yl]amino}pentan-2-ol,
3-({6-[(2-hydroxy-5-fluorobenzyl)amino]-9-(ethyl)-9H-purin-2-yl]amino}pentan-2-ol,
3-({6-[(2-hydroxy-5-fluorobenzyl)amino]-9-(isopropyl)-9H-purin-2-yl]amino}pentan-2-ol,
3-({6-[(2-hydroxy-5-fluorobenzyl)amino]-9-(3-pentyl)-9H-purin-2-yl]amino}pentan-2-ol,
3-({6-[(2-hydroxy-5-fluorobenzyl)amino]-9-(cyklohexyl)-9H-purin-2-yl]amino}pentan-2-ol,
3-({6-[(2-hydroxy-5-fluorobenzyl)amino]-9-(benzyl)-9H-purin-2-yl]amino}pentan-2-ol,
1-({6-[(2-hydroxy-5-fluorobenzyl)amino]-9-(methyl)-9H-purin-2-yl}amino)-2-methyl-propan-2-ol,
1-({6-[(2-hydroxy-5-fluorobenzyl)amino]-9-(ethyl)-9H-purin-2-yl}amino)-2-methyl-propan-2-ol,
1-({6-[(2-hydroxy-5-fluorobenzyl)amino]-9-(isopropyl)-9H-purin-2-yl}amino)-2-methyl-propan-2-ol,
1-({6-[(2-hydroxy-5-fluorobenzyl)amino]-9-(3-pentyl)-9H-purin-2-yl}amino)-2-methyl-propan-2-ol,
1-({6-[(2-hydroxy-5-fluorobenzyl)amino]-9-(cyklohexyl)-9H-purin-2-yl}amino)-2-methyl-propan-2-ol,
1-({6-[(2-hydroxy-5-fluorobenzyl)amino]-9-(benzyl)-9H-purin-2-yl}amino)-2-methyl-propan-2-ol,
2-({6-[(2-hydroxy-5-iodobenzyl)amino]-9-(methyl)-9H-purin-2-yl}amino)butan-1-ol,
2-({6-[(2-hydroxy-5-iodobenzyl)amino]-9-(ethyl)-9H-purin-2-yl}amino)butan-1-ol,
2-({6-[(2-hydroxy-5-iodobenzyl)amino]-9-(isopropyl)-9H-purin-2-yl}amino)butan-1-ol,
2-({6-[(2-hydroxy-5-iodobenzyl)amino]-9-(3-pentyl)-9H-purin-2-yl}amino)butan-1-ol,
2-({6-[(2-hydroxy-5-iodobenzyl)amino]-9-(cyklohexyl)-9H-purin-2-yl}amino)butan-1-ol,
2-({6-[(2-hydroxy-5-iodobenzyl)amino]-9-(benzyl)-9H-purin-2-yl}amino)butan-1-ol,
N6-(2-hydroxy-5-iodobenzyl)-N2-(2-aminopropyl)-9-(methyl)-9H-purin-2,6-diamine,
N6-(2-hydroxy-5-iodobenzyl)-N2-(2-aminopropyl)-9-(ethyl)-9H-purin-2,6-diamine, N6-(2-hydroxy-5-iodobenzyl)-N2-(2-aminopropyl)-9-(isopropyl)-9H-purin-2,6-diamine,
N6-(2-hydroxy-5-iodobenzyl)-N2-(2-aminopropyl)-9-(3-pentyl)-9H-purin-2,6-diamine,
N6-(2-hydroxy-5-iodobenzyl)-N2-(2-aminopropyl)-9-(cyklohexyl)-9H-purin-2,6-diamine,
N6-(2-hydroxy-5-iodobenzyl)-N2-(2-aminopropyl)-9-(benzyl)-9H-purin-2,6-diamine,
2-({6-[(2-hydroxy-5-iodobenzyl)amino]-9-(methyl)-9H-purin-2-yl}amino)-3-methyl-butan-1-ol,
2-({6-[(2-hydroxy-5-iodobenzyl)amino]-9-(ethyl)-9H-purin-2-yl}amino)-3-methyl-butan-1-ol,
2-({6-[(2-hydroxy-5-iodobenzyl)amino]-9-(isopropyl)-9H-purin-2-yl}amino)-3-methyl-butan-1-ol,
2-({6-[(2-hydroxy-5-iodobenzyl)amino]-9-(3-pentyl)-9H-purin-2-yl}amino)-3-methyl-butan-1-ol,
2-({6-[(2-hydroxy-5-iodobenzyl)amino]-9-(cyklohexyl)-9H-purin-2-yl}amino)-3-methyl-butan-1-ol,
2-({6-[(2-hydroxy-5-iodobenzyl)amino]-9-(benzyl)-9H-purin-2-yl}amino)-3-methyl-butan-1-ol,
1-({6-[(2-hydroxy-5-iodobenzyl)amino]-9-(methyl)-9H-purin-2-yl}amino)propan-2-ol,
1-({6-[(2-hydroxy-5-iodobenzyl)amino]-9-(ethyl)-9H-purin-2-yl}amino)propan-2-ol,
1-({6-[(2-hydroxy-5-iodobenzyl)amino]-9-(isopropyl)-9H-purin-2-yl}amino)propan-2-ol,
1-({6-[(2-hydroxy-5-iodobenzyl)amino]-9-(3-pentyl)-9H-purin-2-yl}amino)propan-2-ol,
1-({6-[(2-hydroxy-5-iodobenzyl)amino]-9-(cyklohexyl)-9H-purin-2-yl}amino)propan-2-ol,
1-({6-[(2-hydroxy-5-iodobenzyl)amino]-9-(benzyl)-9H-purin-2-yl}amino)propan-2-ol,
N6-(2-hydroxy-5-iodobenzyl)-N2-(4-aminocyclohexyl)-9-(methyl)-9H-purin-2,6-diamine,
N6-(2-hydroxy-5-iodobenzyl)-N2-(4-aminocyclohexyl)-9-(ethyl)-9H-purin-2,6-diamine,
N6-(2-hydroxy-5-iodobenzyl)-N2-(4-aminocyclohexyl)-9-(isopropyl)-9H-purin-2,6-diamine,
N6-(2-hydroxy-5-iodobenzyl)-N2-(4-aminocyclohexyl)-9-(3-pentyl)-9H-purin-2,6-diamine,
N6-(2-hydroxy-5-iodobenzyl)-N2-(4-aminocyclohexyl)-9-(cyklohexyl)-9H-purin-2,6-diamine,
N6-(2-hydroxy-5-iodobenzyl)-N2-(4-aminocyclohexyl)-9-(benzyl)-9H-purin-2,6-diamine,
1-({6-[(2-hydroxy-5-iodobenzyl)amino]-9-(methyl)-9H-purin-2-yl}amino)-2-methyl-propan-2-ol,
1-({6-[(2-hydroxy-5-iodobenzyl)amino]-9-(ethyl)-9H-purin-2-yl}amino)-2-methyl-propan-2-ol,
1-({6-[(2-hydroxy-5-iodobenzyl)amino]-9-(isopropyl)-9H-purin-2-yl}amino)-2-methyl-propan-2-ol,
1-({6-[(2-hydroxy-5-iodobenzyl)amino]-9-(3-pentyl)-9H-purin-2-yl}amino)-2-methyl-propan-2-ol,
1-({6-[(2-hydroxy-5-iodobenzyl)amino]-9-(cyklohexyl)-9H-purin-2-yl}amino)-2-methyl-propan-2-ol,
1-({6-[(2-hydroxy-5-iodobenzyl)amino]-9-(benzyl)-9H-purin-2-yl}amino)-2-methyl-propan-2-ol,
3-({6-[(2-hydroxy-5-iodobenzyl)amino]-9-(methyl)-9H-purin-2-yl}amino)-2-methyl-butan-2-ol,
3-({6-[(2-hydroxy-5-iodobenzyl)amino]-9-(ethyl)-9H-purin-2-yl}amino)-2-methyl-butan-2-ol,
3-({6-[(2-hydroxy-5-iodobenzyl)amino]-9-(isopropyl)-9H-purin-2-yl}amino)-2-methyl-butan-2-ol,
3-({6-[(2-hydroxy-5-iodobenzyl)amino]-9-(3-pentyl)-9H-purin-2-yl}amino)-2-methyl-butan-2-ol,
3-({6-[(2-hydroxy-5-iodobenzyl)amino]-9-(cyklohexyl)-9H-purin-2-yl}amino)-2-methyl-butan-2-ol,
3-({6-[(2-hydroxy-5-iodobenzyl)amino]-9-(benzyl)-9H-purin-2-yl}amino)-2-methyl-butan-2-ol,
4-({6-[(2-hydroxy-5-iodobenzyl)amino]-9-(methyl)-9H-purin-2-yl}amino)-2-methyl-butan-2-ol,
4-({6-[(2-hydroxy-5-iodobenzyl)amino]-9-(ethyl)-9H-purin-2-yl}amino)-2-methyl-butan-2-ol,
4-({6-[(2-hydroxy-5-iodobenzyl)amino]-9-(isopropyl)-9H-purin-2-yl}amino)-2-methyl-butan-2-ol,
4-({6-[(2-hydroxy-5-iodobenzyl)amino]-9-(3-pentyl)-9H-purin-2-yl}amino)-2-methyl-butan-2-ol,
4-({6-[(2-hydroxy-5-iodobenzyl)amino]-9-(cyklohexyl)-9H-purin-2-yl}amino)-2-methyl-butan-2-ol,
4-({6-[(2-hydroxy-5-iodobenzyl)amino]-9-(benzyl)-9H-purin-2-yl}amino)-2-methyl-butan-2-ol,
4-({6-[(2-hydroxy-5-iodobenzyl)amino]-9-(methyl)-9H-purin-2-yl}amino)-2-methyl-pentan-2-ol,
4-({6-[(2-hydroxy-5-iodobenzyl)amino]-9-(ethyl)-9H-purin-2-yl}amino)-2-methyl-pentan-2-ol,
4-({6-[(2-hydroxy-5-iodobenzyl)amino]-9-(isopropyl)-9H-purin-2-yl}amino)-2-methyl-pentan-2-ol,
4-({6-[(2-hydroxy-5-iodobenzyl)amino]-9-(3-pentyl)-9H-purin-2-yl}amino)-2-methyl-pentan-2-ol,
4-({6-[(2-hydroxy-5-iodobenzyl)amino]-9-(cyklohexyl)-9H-purin-2-yl}amino)-2-methyl-pentan-2-ol,
4-({6-[(2-hydroxy-5-iodobenzyl)amino]-9-(benzyl)-9H-purin-2-yl}amino)-2-methyl-pentan-2-ol,
4-({6-[(2-hydroxy-5-iodobenzyl)amino]-9-(methyl)-9H-purin-2-yl}amino)-2,3-dimethyl-butan-2-ol,
4-({6-[(2-hydroxy-5-iodobenzyl)amino]-9-(ethyl)-9H-purin-2-yl}amino)-2,3-dimethyl-butan-2-ol,
4-({6-[(2-hydroxy-5-iodobenzyl)amino]-9-(isopropyl)-9H-purin-2-yl}amino)-2,3-dimethyl-butan-2-ol,
4-({6-[(2-hydroxy-5-iodobenzyl)amino]-9-(3-pentyl)-9H-purin-2-yl}amino)-2,3-dimethyl-butan-2-ol,
4-({6-[(2-hydroxy-5-iodobenzyl)amino]-9-(cyklohexyl)-9H-purin-2-yl}amino)-2,3-dimethyl-butan-2-ol,
4-({6-[(2-hydroxy-5-iodobenzyl)amino]-9-(benzyl)-9H-purin-2-yl}amino)-2,3-dimethyl-butan-2-ol,
3-({6-[(2-hydroxy-5-iodobenzyl)amino]-9-(methyl)-9H-purin-2-yl}amino)-2-methyl-pentan-2-ol,
3-({6-[(2-hydroxy-5-iodobenzyl)amino]-9-(ethyl)-9H-purin-2-yl}amino)-2-methyl-pentan-2-ol,
3-({6-[(2-hydroxy-5-iodobenzyl)amino]-9-(isopropyl)-9H-purin-2-yl}amino)-2-methyl-pentan-2-ol,
3-({6-[(2-hydroxy-5-iodobenzyl)amino]-9-(3-pentyl)-9H-purin-2-yl}amino)-2-methyl-pentan-2-ol,
3-({6-[(2-hydroxy-5-iodobenzyl)amino]-9-(cyklohexyl)-9H-purin-2-yl}amino)-2-methyl-pentan-2-ol,
3-({6-[(2-hydroxy-5-iodobenzyl)amino]-9-(benzyl)-9H-purin-2-yl}amino)-2-methyl-pentan-2-ol,
3-({6-[(2-hydroxy-5-iodobenzyl)amino]-9-(methyl)-9H-purin-2-yl]amino}pentan-2-ol,
3-({6-[(2-hydroxy-5-iodobenzyl)amino]-9-(ethyl)-9H-purin-2-yl]amino}pentan-2-ol,
3-({6-[(2-hydroxy-5-iodobenzyl)amino]-9-(isopropyl)-9H-purin-2-yl]amino}pentan-2-ol,
3-({6-[(2-hydroxy-5-iodobenzyl)amino]-9-(3-pentyl)-9H-purin-2-yl]amino}pentan-2-ol,
3-({6-[(2-hydroxy-5-iodobenzyl)amino]-9-(cyklohexyl)-9H-purin-2-yl]amino}pentan-2-ol,
3-({6-[(2-hydroxy-5-iodobenzyl)amino]-9-(benzyl)-9H-purin-2-yl]amino}pentan-2-ol,
1-({6-[(2-hydroxy-5-iodobenzyl)amino]-9-(methyl)-9H-purin-2-yl}amino)-2-methyl-propan-2-ol,
1-({6-[(2-hydroxy-5-iodobenzyl)amino]-9-(ethyl)-9H-purin-2-yl}amino)-2-methyl-propan-2-ol, 1-({6-[(2-hydroxy-5-iodobenzyl)amino]-9-(isopropyl)-9H-purin-2-yl}amino)-2-methyl-propan-2-ol,
1-({6-[(2-hydroxy-5-iodobenzyl)amino]-9-(3-pentyl)-9H-purin-2-yl}amino)-2-methyl-propan-2-ol,
1-({6-[(2-hydroxy-5-iodobenzyl)amino]-9-(cyklohexyl)-9H-purin-2-yl}amino)-2-methyl-propan-2-ol,
1-({6-[(2-hydroxy-5-iodobenzyl)amino]-9-(benzyl)-9H-purin-2-yl}amino)-2-methyl-propan-2-ol,
2-({6-[(2-hydroxy-5-methylbenzyl)amino]-9-(methyl)-9H-purin-2-yl}amino)butan-1-ol,
2-({6-[(2-hydroxy-5-methylbenzyl)amino]-9-(ethyl)-9H-purin-2-yl}amino)butan-1-ol,
2-({6-[(2-hydroxy-5-methylbenzyl)amino]-9-(isopropyl)-9H-purin-2-yl}amino)butan-1-ol,
2-({6-[(2-hydroxy-5-methylbenzyl)amino]-9-(3-pentyl)-9H-purin-2-yl}amino)butan-1-ol,
2-({6-[(2-hydroxy-5-methylbenzyl)amino]-9-(cyklohexyl)-9H-purin-2-yl}amino)butan-1-ol,
2-({6-[(2-hydroxy-5-methylbenzyl)amino]-9-(benzyl)-9H-purin-2-yl}amino)butan-1-ol,
N6-(2-hydroxy-5-methylbenzyl)-N2-(2-aminopropyl)-9-(methyl)-9H-purin-2,6-diamine,
N6-(2-hydroxy-5-methylbenzyl)-N2-(2-aminopropyl)-9-(ethyl)-9H-purin-2,6-diamine,
N6-(2-hydroxy-5-methylbenzyl)-N2-(2-aminopropyl)-9-(isopropyl)-9H-purin-2,6-diamine,
N6-(2-hydroxy-5-methylbenzyl)-N2-(2-aminopropyl)-9-(3-pentyl)-9H-purin-2,6-diamine,
N6-(2-hydroxy-5-methylbenzyl)-N2-(2-aminopropyl)-9-(cyklohexyl)-9H-purin-2,6-diamine,
N6-(2-hydroxy-5-methylbenzyl)-N2-(2-aminopropyl)-9-(benzyl)-9H-purin-2,6-diamine,
2-({6-[(2-hydroxy-5-methylbenzyl)amino]-9-(methyl)-9H-purin-2-yl}amino)-3-methyl-butan-1-ol,
2-({6-[(2-hydroxy-5-methylbenzyl)amino]-9-(ethyl)-9H-purin-2-yl}amino)-3-methyl-butan-1-ol,
2-({6-[(2-hydroxy-5-methylbenzyl)amino]-9-(isopropyl)-9H-purin-2-yl}amino)-3-methyl-butan-1-ol,
2-({6-[(2-hydroxy-5-methylbenzyl)amino]-9-(3-pentyl)-9H-purin-2-yl}amino)-3-methyl-butan-1-ol,
2-({6-[(2-hydroxy-5-methylbenzyl)amino]-9-(cyklohexyl)-9H-purin-2-yl}amino)-3-methyl-butan-1-ol,
2-({6-[(2-hydroxy-5-methylbenzyl)amino]-9-(benzyl)-9H-purin-2-yl}amino)-3-methyl-butan-1-ol,
N6-(2-hydroxy-5-methylbenzyl)-N2-(4-aminocyclohexyl)-9-(methyl)-9H-purin-2,6-diamine,
N6-(2-hydroxy-5-methylbenzyl)-N2-(4-aminocyclohexyl)-9-(ethyl)-9H-purin-2,6-diamine,
N6-(2-hydroxy-5-methylbenzyl)-N2-(4-aminocyclohexyl)-9-(isopropyl)-9H-purin-2,6-diamine,
N6-(2-hydroxy-5-methylbenzyl)-N2-(4-aminocyclohexyl)-9-(3-pentyl)-9H-purin-2,6-diamine,
N6-(2-hydroxy-5-methylbenzyl)-N2-(4-aminocyclohexyl)-9-(cyklohexyl)-9H-purin-2,6-diamine,
N6-(2-hydroxy-5-methylbenzyl)-N2-(4-aminocyclohexyl)-9-(benzyl)-9H-purin-2,6-diamine,
1-({6-[(2-hydroxy-5-methylbenzyl)amino]-9-(methyl)-9H-purin-2-yl}amino)-2-methyl-propan-2-ol,
1-({6-[(2-hydroxy-5-methylbenzyl)amino]-9-(ethyl)-9H-purin-2-yl}amino)-2-methyl-propan-2-al,
1-({6-[(2-hydroxy-5-methylbenzyl)amino]-9-(isopropyl)-9H-purin-2-yl}amino)-2-methyl-propan-2-ol,
1-({6-[(2-hydroxy-5-methylbenzyl)amino]-9-(3-pentyl)-9H-purin-2-yl}amino)-2-methyl-propan-2-ol,
1-({6-[(2-hydroxy-5-methylbenzyl)amino]-9-(cyklohexyl)-9H-purin-2-yl}amino)-2-methyl-propan-2-ol,
1-({6-[(2-hydroxy-5-methylbenzyl)amino]-9-(benzyl)-9H-purin-2-yl}amino)-2-methyl-propan-2-ol,
1-({6-[(2-hydroxy-5-methylbenzyl)amino]-9-(methyl)-9H-purin-2-yl}amino)propan-2-ol,
1-({6-[(2-hydroxy-5-methylbenzyl)amino]-9-(ethyl)-9H-purin-2-yl}amino)propan-2-ol,
1-({6-[(2-hydroxy-5-methylbenzyl)amino]-9-(isopropyl)-9H-purin-2-yl}amino)propan-2-ol,
1-({6-[(2-hydroxy-5-methylbenzyl)amino]-9-(3-pentyl)-9H-purin-2-yl}amino)propan-2-ol,
1-({6-[(2-hydroxy-5-methylbenzyl)amino]-9-(cyklohexyl)-9H-purin-2-yl}amino)propan-2-ol
1-({6-[(2-hydroxy-5-methylbenzyl)amino]-9-(benzyl)-9H-purin-2-yl}amino)propan-2-ol,
3-({6-[(2-hydroxy-5-methylbenzyl)amino]-9-(methyl)-9H-purin-2-yl}amino)-2-methyl-butan-2-ol,
3-({6-[(2-hydroxy-5-methylbenzyl)amino]-9-(ethyl)-9H-purin-2-yl}amino)-2-methyl-butan-2-ol,
3-({6-[(2-hydroxy-5-methylbenzyl)amino]-9-(isopropyl)-9H-purin-2-yl}amino)-2-methyl-butan-2-ol,
3-({6-[(2-hydroxy-5-methylbenzyl)amino]-9-(3-pentyl)-9H-purin-2-yl}amino)-2-methyl-butan-2-ol,
3-({6-[(2-hydroxy-5-methylbenzyl)amino]-9-(cyklohexyl)-9H-purin-2-yl}amino)-2-methyl-butan-2-ol,
3-({6-[(2-hydroxy-5-methylbenzyl)amino]-9-(benzyl)-9H-purin-2-yl}amino)-2-methyl-butan-2-ol,
4-({6-[(2-hydroxy-5-methylbenzyl)amino]-9-(methyl)-9H-purin-2-yl}amino)-2-methyl-butan-2-ol,
4-({6-[(2-hydroxy-5-methylbenzyl)amino]-9-(ethyl)-9H-purin-2-yl}amino)-2-methyl-butan-2-ol,
4-({6-[(2-hydroxy-5-methylbenzyl)amino]-9-(isopropyl)-9H-purin-2-yl}amino)-2-methyl-butan-2-ol,
4-({6-[(2-hydroxy-5-methylbenzyl)amino]-9-(3-pentyl)-9H-purin-2-yl}amino)-2-methyl-butan-2-ol,
4-({6-[(2-hydroxy-5-methylbenzyl)amino]-9-(cyklohexyl)-9H-purin-2-yl}amino)-2-methyl-butan-2-ol,
4-({6-[(2-hydroxy-5-methylbenzyl)amino]-9-(benzyl)-9H-purin-2-yl}amino)-2-methyl-butan-2-ol,
4-({6-[(2-hydroxy-5-methylbenzyl)amino]-9-(methyl)-9H-purin-2-yl}amino)-2-methyl-pentan-2-ol,
4-({6-[(2-hydroxy-5-methylbenzyl)amino]-9-(ethyl)-9H-purin-2-yl}amino)-2-methyl-pentan-2-ol,
4-({6-[(2-hydroxy-5-methylbenzyl)amino]-9-(isopropyl)-9H-purin-2-yl}amino)-2-methyl-pentan-2-ol,
4-({6-[(2-hydroxy-5-methylbenzyl)amino]-9-(3-pentyl)-9H-purin-2-yl}amino)-2-methyl-pentan-2-ol,
4-({6-[(2-hydroxy-5-methylbenzyl)amino]-9-(cyklohexyl)-9H-purin-2-yl}amino)-2-methyl-pentan-2-ol,
4-({6-[(2-hydroxy-5-methylbenzyl)amino]-9-(benzyl)-9H-purin-2-yl}amino)-2-methyl-pentan-2-ol,
4-({6-[(2-hydroxy-5-methylbenzyl)amino]-9-(methyl)-9H-purin-2-yl}amino)-2,3-dimethyl-butan-2-ol,
4-({6-[(2-hydroxy-5-methylbenzyl)amino]-9-(ethyl)-9H-purin-2-yl}amino)-2,3-dimethyl-butan-2-ol,
4-({6-[(2-hydroxy-5-methylbenzyl)amino]-9-(isopropyl)-9H-purin-2-yl}amino)-2,3-dimethyl-butan-2-ol,
4-({6-[(2-hydroxy-5-methylbenzyl)amino]-9-(3-pentyl)-9H-purin-2-yl}amino)-2,3-dimethyl-butan-2-ol,
4-({6-[(2-hydroxy-5-methylbenzyl)amino]-9-(cyklohexyl)-9H-purin-2-yl}amino)-2,3-dimethyl-butan-2-ol,
4-({6-[(2-hydroxy-5-methylbenzyl)amino]-9-(benzyl)-9H-purin-2-yl}amino)-2,3-dimethyl-butan-2-ol,
3-({6-[(2-hydroxy-5-methylbenzyl)amino]-9-(methyl)-9H-purin-2-yl}amino)-2-methyl-pentan-2-ol,
3-({6-[(2-hydroxy-5-methylbenzyl)amino]-9-(ethyl)-9H-purin-2-yl}amino)-2-methyl-pentan-2-ol, 3-({6-[(2-hydroxy-5-methylbenzyl)amino]-9-(isopropyl)-9H-purin-2-yl}amino)-2-methyl-pentan-2-ol,
3-({6-[(2-hydroxy-5-methylbenzyl)amino]-9-(3-pentyl)-9H-purin-2-yl}amino)-2-methyl-pentan-2-ol,
3-({6-[(2-hydroxy-5-methylbenzyl)amino]-9-(cyklohexyl)-9H-purin-2-yl}amino)-2-methyl-pentan-2-ol,
3-({6-[(2-hydroxy-5-methylbenzyl)amino]-9-(benzyl)-9H-purin-2-yl}amino)-2-methyl-pentan-2-ol,
3-({6-[(2-hydroxy-5-methylbenzyl)amino]-9-(methyl)-9H-purin-2-yl]amino}pentan-2-ol,
3-({6-[(2-hydroxy-5-methylbenzyl)amino]-9-(ethyl)-9H-purin-2-yl]amino}pentan-2-ol,
3-({6-[(2-hydroxy-5-methylbenzyl)amino]-9-(isopropyl)-9H-purin-2-yl]amino}pentan-2-ol,
3-({6-[(2-hydroxy-5-methylbenzyl)amino]-9-(3-pentyl)-9H-purin-2-yl]amino}pentan-2-ol,
3-({6-[(2-hydroxy-5-methylbenzyl)amino]-9-(cyklohexyl)-9H-purin-2-yl]amino}pentan-2-ol,
3-({6-[(2-hydroxy-5-methylbenzyl)amino]-9-(benzyl)-9H-purin-2-yl]amino}pentan-2-ol,
1-({6-[(2-hydroxy-5-methylbenzyl)amino]-9-(methyl)-9H-purin-2-yl}amino)-2-methyl-propan-2-ol,
1-({6-[(2-hydroxy-5-methylbenzyl)amino]-9-(ethyl)-9H-purin-2-yl}amino)-2-methyl-propan-2-ol,
1-({6-[(2-hydroxy-5-methylbenzyl)amino]-9-(isopropyl)-9H-purin-2-yl}amino)-2-methyl-propan-2-ol,
1-({6-[(2-hydroxy-5-methylbenzyl)amino]-9-(3-pentyl)-9H-purin-2-yl}amino)-2-methyl-propan-2-ol,
1-({6-[(2-hydroxy-5-methylbenzyl)amino]-9-(cyklohexyl)-9H-purin-2-yl}amino)-2-methyl-propan-2-ol,
1-({6-[(2-hydroxy-5-methylbenzyl)amino]-9-(benzyl)-9H-purin-2-yl}amino)-2-methyl-propan-2-ol,
2-({6-[(2-hydroxy-3-methylbenzyl)amino]-9-(methyl)-9H-purin-2-yl}amino)butan-1-ol,
2-({6-[(2-hydroxy-3-methylbenzyl)amino]-9-(ethyl)-9H-purin-2-yl}amino)butan-1-ol,
2-({6-[(2-hydroxy-3-methylbenzyl)amino]-9-(isopropyl)-9H-purin-2-yl}amino)butan-1-ol,
2-({6-[(2-hydroxy-3-methylbenzyl)amino]-9-(3-pentyl)-9H-purin-2-yl}amino)butan-1-ol,
2-({6-[(2-hydroxy-3-methylbenzyl)amino]-9-(cyklohexyl)-9H-purin-2-yl}amino)butan-1-ol,
2-({6-[(2-hydroxy-3-methylbenzyl)amino]-9-(benzyl)-9H-purin-2-yl}amino)butan-1-ol,
N6-(2-hydroxy-3-methylbenzyl)-N2-(2-aminopropyl)-9-(methyl)-9H-purin-2,6-diamine,
N6-(2-hydroxy-3-methylbenzyl)-N2-(2-aminopropyl)-9-(ethyl)-9H-purin-2,6-diamine,
N6-(2-hydroxy-3-methylbenzyl)-N2-(2-aminopropyl)-9-(isopropyl)-9H-purin-2,6-diamine,
N6-(2-hydroxy-3-methylbenzyl)-N2-(2-aminopropyl)-9-(3-pentyl)-9H-purin-2,6-diamine,
N6-(2-hydroxy-3-methylbenzyl)-N2-(2-aminopropyl)-9-(cyklohexyl)-9H-purin-2,6-diamine,
N6-(2-hydroxy-3-methylbenzyl)-N2-(2-aminopropyl)-9-(benzyl)-9H-purin-2,6-diamine,
2-({6-[(2-hydroxy-5-fluorobenzyl)amino]-9-(methyl)-9H-purin-2-yl}amino)-3-methyl-butan-1-ol,
2-({6-[(2-hydroxy-5-fluorobenzyl)amino]-9-(ethyl)-9H-purin-2-yl}amino)-3-methyl-butan-1-ol,
2-({6-[(2-hydroxy-5-fluorobenzyl)amino]-9-(isopropyl)-9H-purin-2-yl}amino)-3-methyl-butan-1-ol,
2-({6-[(2-hydroxy-5-fluorobenzyl)amino]-9-(3-pentyl)-9H-purin-2-yl}amino)-3-methyl-butan-1-ol,
2-({6-[(2-hydroxy-5-fluorobenzyl)amino]-9-(cyklohexyl)-9H-purin-2-yl}amino)-3-methyl-butan-1-ol,
2-({6-[(2-hydroxy-5-fluorobenzyl)amino]-9-(benzyl)-9H-purin-2-yl}amino)-3-methyl-butan-1-ol,
N6-(2-hydroxy-3-methylbenzyl)-N2-(4-aminocyclohexyl)-9-(methyl)-9H-purin-2,6-diamine,
N6-(2-hydroxy-3-methylbenzyl)-N2-(4-aminocyclohexyl)-9-(ethyl)-9H-purin-2,6-diamine,
N6-(2-hydroxy-3-methylbenzyl)-N2-(4-aminocyclohexyl)-9-(isopropyl)-9H-purin-2,6-diamine,
N6-(2-hydroxy-3-methylbenzyl)-N2-(4-aminocyclohexyl)-9-(3-pentyl)-9H-purin-2,6-diamine,
N6-(2-hydroxy-3-methylbenzyl)-N2-(4-aminocyclohexyl)-9-(cyklohexyl)-9H-purin-2,6-diamine,
N6-(2-hydroxy-3-methylbenzyl)-N2-(4-aminocyclohexyl)-9-(benzyl)-9H-purin-2,6-diamine,
1-({6-[(2-hydroxy-3-methylbenzyl)amino]-9-(methyl)-9H-purin-2-yl}amino)-2-methyl-propan-2-ol,
1-({6-[(2-hydroxy-3-methylbenzyl)amino]-9-(ethyl)-9H-purin-2-yl}amino)-2-methyl-propan-2-ol,
1-({6-[(2-hydroxy-3-methylbenzyl)amino]-9-(isopropyl)-9H-purin-2-yl}amino)-2-methyl-propan-2-ol,
1-({6-[(2-hydroxy-3-methylbenzyl)amino]-9-(3-pentyl)-9H-purin-2-yl}amino)-2-methyl-propan-2-ol,
1-({6-[(2-hydroxy-3-methylbenzyl)amino]-9-(cyklohexyl)-9H-purin-2-yl}amino)-2-methyl-propan-2-ol,
1-({6-[(2-hydroxy-3-methylbenzyl)amino]-9-(benzyl)-9H-purin-2-yl}amino)-2-methyl-propan-2-ol,
1-({6-[(2-hydroxy-3-methylbenzyl)amino]-9-(methyl)-9H-purin-2-yl}amino)propan-2-ol,
1-({6-[(2-hydroxy-3-methylbenzyl)amino]-9-(ethyl)-9H-purin-2-yl}amino)propan-2-ol,
1-({6-[(2-hydroxy-3-methylbenzyl)amino]-9-(isopropyl)-9H-purin-2-yl}amino)propan-2-ol,
1-({6-[(2-hydroxy-3-methylbenzyl)amino]-9-(3-pentyl)-9H-purin-2-yl}amino)propan-2-ol,
1-({6-[(2-hydroxy-3-methylbenzyl)amino]-9-(cyklohexyl)-9H-purin-2-yl}amino)propan-2-ol
1-({6-[(2-hydroxy-3-methylbenzyl)amino]-9-(benzyl)-9H-purin-2-yl}amino)propan-2-ol,
3-({6-[(2-hydroxy-3-methylbenzyl)amino]-9-(methyl)-9H-purin-2-yl}amino)-2-methyl-butan-2-ol,
3-({6-[(2-hydroxy-3-methylbenzyl)amino]-9-(ethyl)-9H-purin-2-yl}amino)-2-methyl-butan-2-ol,
3-({6-[(2-hydroxy-3-methylbenzyl)amino]-9-(isopropyl)-9H-purin-2-yl}amino)-2-methyl-butan-2-ol,
3-({6-[(2-hydroxy-3-methylbenzyl)amino]-9-(3-pentyl)-9H-purin-2-yl}amino)-2-methyl-butan-2-ol,
3-({6-[(2-hydroxy-3-methylbenzyl)amino]-9-(cyklohexyl)-9H-purin-2-yl}amino)-2-methyl-butan-2-ol,
3-({6-[(2-hydroxy-3-methylbenzyl)amino]-9-(benzyl)-9H-purin-2-yl}amino)-2-methyl-butan-2-ol,
4-({6-[(2-hydroxy-3-methylbenzyl)amino]-9-(methyl)-9H-purin-2-yl}amino)-2-methyl-butan-2-ol,
4-({6-[(2-hydroxy-3-methylbenzyl)amino]-9-(ethyl)-9H-purin-2-yl}amino)-2-methyl-butan-2-ol,
4-({6-[(2-hydroxy-3-methylbenzyl)amino]-9-(isopropyl)-9H-purin-2-yl}amino)-2-methyl-butan-2-ol,
4-({6-[(2-hydroxy-3-methylbenzyl)amino]-9-(3-pentyl)-9H-purin-2-yl}amino)-2-methyl-butan-2-ol,
4-({6-[(2-hydroxy-3-methylbenzyl)amino]-9-(cyklohexyl)-9H-purin-2-yl}amino)-2-methyl-butan-2-ol,
4-({6-[(2-hydroxy-3-methylbenzyl)amino]-9-(benzyl)-9H-purin-2-yl}amino)-2-methyl-butan-2-ol,
4-({6-[(2-hydroxy-3-methylbenzyl)amino]-9-(methyl)-9H-purin-2-yl}amino)-2-methyl-pentan-2-ol,
4-({6-[(2-hydroxy-3-methylbenzyl)amino]-9-(ethyl)-9H-purin-2-yl}amino)-2-methyl-pentan-2-ol, 4-({6-[(2-hydroxy-3-methylbenzyl)amino]-9-(isopropyl)-9H-purin-2-yl}amino)-2-methyl-pentan-2-ol,
4-({6-[(2-hydroxy-3-methylbenzyl)amino]-9-(3-pentyl)-9H-purin-2-yl}amino)-2-methyl-pentan-2-ol,
4-({6-[(2-hydroxy-3-methylbenzyl)amino]-9-(cyklohexyl)-9H-purin-2-yl}amino)-2-methyl-pentan-2-ol,
4-({6-[(2-hydroxy-3-methylbenzyl)amino]-9-(benzyl)-9H-purin-2-yl}amino)-2-methyl-pentan-2-ol,
4-({6-[(2-hydroxy-3-methylbenzyl)amino]-9-(methyl)-9H-purin-2-yl}amino)-2,3-dimethyl-butan-2-ol,
4-({6-[(2-hydroxy-3-methylbenzyl)amino]-9-(ethyl)-9H-purin-2-yl}amino)-2,3-dimethyl-butan-2-ol,
4-({6-[(2-hydroxy-3-methylbenzyl)amino]-9-(isopropyl)-9H-purin-2-yl}amino)-2,3-dimethyl-butan-2-ol,
4-({6-[(2-hydroxy-3-methylbenzyl)amino]-9-(3-pentyl)-9H-purin-2-yl}amino)-2,3-dimethyl-butan-2-ol,
4-({6-[(2-hydroxy-3-methylbenzyl)amino]-9-(cyklohexyl)-9H-purin-2-yl}amino)-2,3-dimethyl-butan-2-ol,
4-({6-[(2-hydroxy-3-methylbenzyl)amino]-9-(benzyl)-9H-purin-2-yl}amino)-2,3-dimethyl-butan-2-ol,
3-({6-[(2-hydroxy-3-methylbenzyl)amino]-9-(methyl)-9H-purin-2-yl}amino)-2-methyl-pentan-2-ol,
3-({6-[(2-hydroxy-3-methylbenzyl)amino]-9-(ethyl)-9H-purin-2-yl}amino)-2-methyl-pentan-2-ol,
3-({6-[(2-hydroxy-3-methylbenzyl)amino]-9-(isopropyl)-9H-purin-2-yl}amino)-2-methyl-pentan-2-ol,
3-({6-[(2-hydroxy-3-methylbenzyl)amino]-9-(3-pentyl)-9H-purin-2-yl}amino)-2-methyl-pentan-2-ol,
3-({6-[(2-hydroxy-3-methylbenzyl)amino]-9-(cyklohexyl)-9H-purin-2-yl}amino)-2-methyl-pentan-2-ol,
3-({6-[(2-hydroxy-3-methylbenzyl)amino]-9-(benzyl)-9H-purin-2-yl}amino)-2-methyl-pentan-2-ol,
3-({6-[(2-hydroxy-3-methylbenzyl)amino]-9-(methyl)-9H-purin-2-yl]amino}pentan-2-ol,
3-({6-[(2-hydroxy-3-methylbenzyl)amino]-9-(ethyl)-9H-purin-2-yl]amino}pentan-2-ol,
3-({6-[(2-hydroxy-3-methylbenzyl)amino]-9-(isopropyl)-9H-purin-2-yl]amino}pentan-2-ol,
3-({6-[(2-hydroxy-3-methylbenzyl)amino]-9-(3-pentyl)-9H-purin-2-yl]amino}pentan-2-ol,
3-({6-[(2-hydroxy-3-methylbenzyl)amino]-9-(cyklohexyl)-9H-purin-2-yl]amino}pentan-2-ol,
3-({6-[(2-hydroxy-3-methylbenzyl)amino]-9-(benzyl)-9H-purin-2-yl]amino}pentan-2-ol,
1-({6-[(2-hydroxy-3-methylbenzyl)amino]-9-(methyl)-9H-purin-2-yl}amino)-2-methyl-propan-2-ol,
1-({6-[(2-hydroxy-3-methylbenzyl)amino]-9-(ethyl)-9H-purin-2-yl}amino)-2-methyl-propan-2-ol,
1-({6-[(2-hydroxy-3-methylbenzyl)amino]-9-(isopropyl)-9H-purin-2-yl}amino)-2-methyl-propan-2-ol,
1-({6-[(2-hydroxy-3-methylbenzyl)amino]-9-(3-pentyl)-9H-purin-2-yl}amino)-2-methyl-propan-2-ol,
1-({6-[(2-hydroxy-3-methylbenzyl)amino]-9-(cyklohexyl)-9H-purin-2-yl}amino)-2-methyl-propan-2-ol,
1-({6-[(2-hydroxy-3-methylbenzyl)amino]-9-(benzyl)-9H-purin-2-yl}amino)-2-methyl-propan-2-ol,
2-({6-[(2-hydroxy-3-methoxybenzyl)amino]-9-(methyl)-9H-purin-2-yl}amino)butan-1-ol,
2-({6-[(2-hydroxy-3-methoxybenzyl)amino]-9-(ethyl)-9H-purin-2-yl}amino)butan-1-ol,
2-({6-[(2-hydroxy-3-methoxybenzyl)amino]-9-(isopropyl)-9H-purin-2-yl}amino)butan-1-ol,
2-({6-[(2-hydroxy-3-methoxybenzyl)amino]-9-(3-pentyl)-9H-purin-2-yl}amino)butan-1-ol,
2-({6-[(2-hydroxy-3-methoxybenzyl)amino]-9-(cyklohexyl)-9H-purin-2-yl}amino)butan-1-ol
2-({6-[(2-hydroxy-3-methoxybenzyl)amino]-9-(benzyl)-9H-purin-2-yl}amino)butan-1-ol,
N6-(2-hydroxy-3-methoxybenzyl)-N2-(2-aminopropyl)-9-(methyl)-9H-purin-2,6-diamine,
N6-(2-hydroxy-3-methoxybenzyl)-N2-(2-aminopropyl)-9-(ethyl)-9H-purin-2,6-diamine,
N6-(2-hydroxy-3-methoxybenzyl)-N2-(2-aminopropyl)-9-(isopropyl)-9H-purin-2,6-diamine,
N6-(2-hydroxy-3-methoxybenzyl)-N2-(2-aminopropyl)-9-(3-pentyl)-9H-purin-2,6-diamine,
N6-(2-hydroxy-3-methoxybenzyl)-N2-(2-aminopropyl)-9-(cyklohexyl)-9H-purin-2,6-diamine,
N6-(2-hydroxy-3-methoxybenzyl)-N2-(2-aminopropyl)-9-(benzyl)-9H-purin-2,6-diamine,
2-({6-[(2-hydroxy-3-methoxybenzyl)amino]-9-(methyl)-9H-purin-2-yl}amino)-3-methyl-butan-1-ol,
2-({6-[(2-hydroxy-3-methoxybenzyl)amino]-9-(ethyl)-9H-purin-2-yl}amino)-3-methyl-butan-1-ol,
2-({6-[(2-hydroxy-3-methoxybenzyl)amino]-9-(isopropyl)-9H-purin-2-yl}amino)-3-methyl-butan-1-ol,
2-({6-[(2-hydroxy-3-methoxybenzyl)amino]-9-(3-pentyl)-9H-purin-2-yl}amino)-3-methyl-butan-1-ol,
2-({6-[(2-hydroxy-3-methoxybenzyl)amino]-9-(cyklohexyl)-9H-purin-2-yl}amino)-3-methyl-butan-1-ol,
2-({6-[(2-hydroxy-3-methoxybenzyl)amino]-9-(benzyl)-9H-purin-2-yl}amino)-3-methyl-butan-1-ol,
N6-(2-hydroxy-3-methoxybenzyl)-N2-(4-aminocyclohexyl)-9-(methyl)-9H-purin-2,6-diamine,
N6-(2-hydroxy-3-methoxybenzyl)-N2-(4-aminocyclohexyl)-9-(ethyl)-9H-purin-2,6-diamine,
N6-(2-hydroxy-3-methoxybenzyl)-N2-(4-aminocyclohexyl)-9-(isopropyl)-9H-purin-2,6-diamine,
N6-(2-hydroxy-3-methoxybenzyl)-N2-(4-aminocyclohexyl)-9-(3-pentyl)-9H-purin-2,6-diamine,
N6-(2-hydroxy-3-methoxybenzyl)-N2-(4-aminocyclohexyl)-9-(cyklohexyl)-9H-purin-2,6-diamine,
N6-(2-hydroxy-3-methoxybenzyl)-N2-(4-aminocyclohexyl)-9-(benzyl)-9H-purin-2,6-diamine,
1-({6-[(2-hydroxy-3-methoxybenzyl)amino]-9-(methyl)-9H-purin-2-yl}amino)-2-methyl-propan-2-ol,
1-({6-[(2-hydroxy-3-methoxybenzyl)amino]-9-(ethyl)-9H-purin-2-yl}amino)-2-methyl-propan-2-ol,
1-({6-[(2-hydroxy-3-methoxybenzyl)amino]-9-(isopropyl)-9H-purin-2-yl}amino)-2-methyl-propan-2-ol,
1-({6-[(2-hydroxy-3-methoxybenzyl)amino]-9-(3-pentyl)-9H-purin-2-yl}amino)-2-methyl-propan-2-ol,
1-({6-[(2-hydroxy-3-methoxybenzyl)amino]-9-(cyklohexyl)-9H-purin-2-yl}amino)-2-methyl-propan-2-ol,
1-({6-[(2-hydroxy-3-methoxybenzyl)amino]-9-(benzyl)-9H-purin-2-yl}amino)-2-methyl-propan-2-ol,
1-({6-[(2-hydroxy-3-methoxybenzyl)amino]-9-(methyl)-9H-purin-2-yl}amino)propan-2-ol,
1-({6-[(2-hydroxy-3-methoxybenzyl)amino]-9-(ethyl)-9H-purin-2-yl}amino)propan-2-ol,
1-({6-[(2-hydroxy-3-methoxybenzyl)amino]-9-(isopropyl)-9H-purin-2-yl}amino)propan-2-ol
1-({6-[(2-hydroxy-3-methoxybenzyl)amino]-9-(3-pentyl)-9H-purin-2-yl}amino)propan-2-ol,
1-({6-[(2-hydroxy-3-methoxybenzyl)amino]-9-(cyklohexyl)-9H-purin-2-yl}amino)propan-2-ol,
1-({6-[(2-hydroxy-3-methoxybenzyl)amino]-9-(benzyl)-9H-purin-2-yl}amino)propan-2-ol,
3-({6-[(2-hydroxy-3-methoxybenzyl)amino]-9-(methyl)-9H-purin-2-yl}amino)-2-methyl-butan-2-ol,
3-({6-[(2-hydroxy-3-methoxybenzyl)amino]-9-(ethyl)-9H-purin-2-yl}amino)-2-methyl-butan-2-ol, 3-({6-[(2-hydroxy-3-methoxybenzyl)amino]-9-(isopropyl)-9H-purin-2-yl}amino)-2-methyl-butan-2-ol,
3-({6-[(2-hydroxy-3-methoxybenzyl)amino]-9-(3-pentyl)-9H-purin-2-yl}amino)-2-methyl-butan-2-ol,
3-({6-[(2-hydroxy-3-methoxybenzyl)amino]-9-(cyklohexyl)-9H-purin-2-yl}amino)-2-methyl-butan-2-ol,
3-({6-[(2-hydroxy-3-methoxybenzyl)amino]-9-(benzyl)-9H-purin-2-yl}amino)-2-methyl-butan-2-ol,
4-({6-[(2-hydroxy-3-methoxybenzyl)amino]-9-(methyl)-9H-purin-2-yl}amino)-2-methyl-butan-2-ol,
4-({6-[(2-hydroxy-3-methoxybenzyl)amino]-9-(ethyl)-9H-purin-2-yl}amino)-2-methyl-butan-2-ol,
4-({6-[(2-hydroxy-3-methoxybenzyl)amino]-9-(isopropyl)-9H-purin-2-yl}amino)-2-methyl-butan-2-ol,
4-({6-[(2-hydroxy-3-methoxybenzyl)amino]-9-(3-pentyl)-9H-purin-2-yl}amino)-2-methyl-butan-2-ol,
4-({6-[(2-hydroxy-3-methoxybenzyl)amino]-9-(cyklohexyl)-9H-purin-2-yl}amino)-2-methyl-butan-2-ol,
4-({6-[(2-hydroxy-3-methoxybenzyl)amino]-9-(benzyl)-9H-purin-2-yl}amino)-2-methyl-butan-2-ol,
4-({6-[(2-hydroxy-3-methoxybenzyl)amino]-9-(methyl)-9H-purin-2-yl}amino)-2-methyl-pentan-2-ol,
4-({6-[(2-hydroxy-3-methoxybenzyl)amino]-9-(ethyl)-9H-purin-2-yl}amino)-2-methyl-pentan-2-ol,
4-({6-[(2-hydroxy-3-methoxybenzyl)amino]-9-(isopropyl)-9H-purin-2-yl}amino)-2-methyl-pentan-2-ol,
4-({6-[(2-hydroxy-3-methoxybenzyl)amino]-9-(3-pentyl)-9H-purin-2-yl}amino)-2-methyl-pentan-2-ol,
4-({6-[(2-hydroxy-3-methoxybenzyl)amino]-9-(cyklohexyl)-9H-purin-2-yl}amino)-2-methyl-pentan-2-ol,
4-({6-[(2-hydroxy-3-methoxybenzyl)amino]-9-(benzyl)-9H-purin-2-yl}amino)-2-methyl-pentan-2-ol,
4-({6-[(2-hydroxy-3-methoxybenzyl)amino]-9-(methyl)-9H-purin-2-yl}amino)-2,3-dimethyl-butan-2-ol,
4-({6-[(2-hydroxy-3-methoxybenzyl)amino]-9-(ethyl)-9H-purin-2-yl}amino)-2,3-dimethyl-butan-2-ol,
4-({6-[(2-hydroxy-3-methoxybenzyl)amino]-9-(isopropyl)-9H-purin-2-yl}amino)-2,3-dimethyl-butan-2-ol,
4-({6-[(2-hydroxy-3-methoxybenzyl)amino]-9-(3-pentyl)-9H-purin-2-yl}amino)-2,3-dimethyl-butan-2-ol,
4-({6-[(2-hydroxy-3-methoxybenzyl)amino]-9-(cyklohexyl)-9H-purin-2-yl}amino)-2,3-dimethyl-butan-2-ol,
4-({6-[(2-hydroxy-3-methoxybenzyl)amino]-9-(benzyl)-9H-purin-2-yl}amino)-2,3-dimethyl-butan-2-ol,
4-({6-[(2-hydroxy-3-methoxybenzyl)amino]-9-(methyl)-9H-purin-2-yl}amino)-2,3-dimethyl-butan-2-ol,
4-({6-[(2-hydroxy-3-methoxybenzyl)amino]-9-(ethyl)-9H-purin-2-yl}amino)-2,3-dimethyl-butan-2-ol,
4-({6-[(2-hydroxy-3-methoxybenzyl)amino]-9-(isopropyl)-9H-purin-2-yl}amino)-2,3-dimethyl-butan-2-ol,
4-({6-[(2-hydroxy-3-methoxybenzyl)amino]-9-(3-pentyl)-9H-purin-2-yl}amino)-2,3-dimethyl-butan-2-ol,
4-({6-[(2-hydroxy-3-methoxybenzyl)amino]-9-(cyklohexyl)-9H-purin-2-yl}amino)-2,3-dimethyl-butan-2-ol,
4-({6-[(2-hydroxy-3-methoxybenzyl)amino]-9-(benzyl)-9H-purin-2-yl}amino)-2,3-dimethyl-butan-2-ol,
3-({6-[(2-hydroxy-3-methoxybenzyl)amino]-9-(methyl)-9H-purin-2-yl}amino)-2-methyl-pentan-2-ol,
3-({6-[(2-hydroxy-3-methoxybenzyl)amino]-9-(ethyl)-9H-purin-2-yl}amino)-2-methyl-pentan-2-ol,
3-({6-[(2-hydroxy-3-methoxybenzyl)amino]-9-(isopropyl)-9H-purin-2-yl}amino)-2-methyl-pentan-2-ol,
3-({6-[(2-hydroxy-3-methoxybenzyl)amino]-9-(3-pentyl)-9H-purin-2-yl}amino)-2-methyl-pentan-2-ol,
3-({6-[(2-hydroxy-3-methoxybenzyl)amino]-9-(cyklohexyl)-9H-purin-2-yl}amino)-2-methyl-pentan-2-ol,
3-({6-[(2-hydroxy-3-methoxybenzyl)amino]-9-(benzyl)-9H-purin-2-yl}amino)-2-methyl-pentan-2-ol,
3-({6-[(2-hydroxy-3-methoxybenzyl)amino]-9-(methyl)-9H-purin-2-yl]amino}pentan-2-ol,
3-({6-[(2-hydroxy-3-methoxybenzyl)amino]-9-(ethyl)-9H-purin-2-yl]amino}pentan-2-ol,
3-({6-[(2-hydroxy-3-methoxybenzyl)amino]-9-(isopropyl)-9H-purin-2-yl]amino}pentan-2-ol
3-({6-[(2-hydroxy-3-methoxybenzyl)amino]-9-(3-pentyl)-9H-purin-2-yl]amino}pentan-2-ol,
3-({6-[(2-hydroxy-3-methoxybenzyl)amino]-9-(cyklohexyl)-9H-purin-2-yl]amino}pentan-2-ol,
3-({6-[(2-hydroxy-3-methoxybenzyl)amino]-9-(benzyl)-9H-purin-2-yl]amino}pentan-2-ol,
1-({6-[(2-hydroxy-3-methoxybenzyl)amino]-9-(methyl)-9H-purin-2-yl}amino)-2-methyl-propan-2-ol,
1-({6-[(2-hydroxy-3-methoxybenzyl)amino]-9-(ethyl)-9H-purin-2-yl}amino)-2-methyl-propan-2-ol,
1-({6-[(2-hydroxy-3-methoxybenzyl)amino]-9-(isopropyl)-9H-purin-2-yl}amino)-2-methyl-propan-2-ol,
1-({6-[(2-hydroxy-3-methoxybenzyl)amino]-9-(3-pentyl)-9H-purin-2-yl}amino)-2-methyl-propan-2-ol,
1-({6-[(2-hydroxy-3-methoxybenzyl)amino]-9-(cyklohexyl)-9H-purin-2-yl}amino)-2-methyl-propan-2-ol,
1-({6-[(2-hydroxy-3-methoxybenzyl)amino]-9-(benzyl)-9H-purin-2-yl}amino)-2-methyl-propan-2-ol,
1-({6-[(2-hydroxy-5-methoxybenzyl)amino]-9-(methyl)-9H-purin-2-yl}amino)propan-2-ol,
1-({6-[(2-hydroxy-5-methoxybenzyl)amino]-9-(ethyl)-9H-purin-2-yl}amino)propan-2-ol,
1-({6-[(2-hydroxy-5-methoxybenzyl)amino]-9-(isopropyl)-9H-purin-2-yl}amino)propan-2-ol
1-({6-[(2-hydroxy-5-methoxybenzyl)amino]-9-(3-pentyl)-9H-purin-2-yl}amino)propan-2-ol,
1-({6-[(2-hydroxy-5-methoxybenzyl)amino]-9-(cyklohexyl)-9H-purin-2-yl}amino)propan-2-ol,
1-({6-[(2-hydroxy-5-methoxybenzyl)amino]-9-(benzyl)-9H-purin-2-yl}amino)propan-2-ol,
2-({6-[(2-hydroxy-5-methoxybenzyl)amino]-9-(methyl)-9H-purin-2-yl}amino)butan-1-ol,
2-({6-[(2-hydroxy-5-methoxybenzyl)amino]-9-(ethyl)-9H-purin-2-yl}amino)butan-1-ol,
2-({6-[(2-hydroxy-5-methoxybenzyl)amino]-9-(isopropyl)-9H-purin-2-yl}amino)butan-1-ol,
2-({6-[(2-hydroxy-5-methoxybenzyl)amino]-9-(3-pentyl)-9H-purin-2-yl}amino)butan-1-ol,
2-({6-[(2-hydroxy-5-methoxybenzyl)amino]-9-(cyklohexyl)-9H-purin-2-yl}amino)butan-1-ol
2-({6-[(2-hydroxy-5-methoxybenzyl)amino]-9-(benzyl)-9H-purin-2-yl}amino)butan-1-ol,
N6-(2-hydroxy-5-methoxybenzyl)-N2-(2-aminopropyl)-9-(methyl)-9H-purin-2,6-diamine,
N6-(2-hydroxy-5-methoxybenzyl)-N2-(2-aminopropyl)-9-(ethyl)-9H-purin-2,6-diamine,
N6-(2-hydroxy-5-methoxybenzyl)-N2-(2-aminopropyl)-9-(isopropyl)-9H-purin-2,6-diamine,
N6-(2-hydroxy-5-methoxybenzyl)-N2-(2-aminopropyl)-9-(3-pentyl)-9H-purin-2,6-diamine,
N6-(2-hydroxy-5-methoxybenzyl)-N2-(2-aminopropyl)-9-(cyklohexyl)-9H-purin-2,6-diamine,
N6-(2-hydroxy-5-methoxybenzyl)-N2-(2-aminopropyl)-9-(benzyl)-9H-purin-2,6-diamine,
2-({6-[(2-hydroxy-5-fluorobenzyl)amino]-9-(methyl)-9H-purin-2-yl}amino)-3-methyl-butan-1-ol,
2-({6-[(2-hydroxy-5-fluorobenzyl)amino]-9-(ethyl)-9H-purin-2-yl}amino)-3-methyl-butan-1-ol, 2-({6-[(2-hydroxy-5-fluorobenzyl)amino]-9-(isopropyl)-9H-purin-2-yl}amino)-3-methyl-butan-1-ol,
2-({6-[(2-hydroxy-5-fluorobenzyl)amino]-9-(3-pentyl)-9H-purin-2-yl}amino)-3-methyl-butan-1-ol,
2-({6-[(2-hydroxy-5-fluorobenzyl)amino]-9-(cyklohexyl)-9H-purin-2-yl}amino)-3-methyl-butan-1-ol,
2-({6-[(2-hydroxy-5-fluorobenzyl)amino]-9-(benzyl)-9H-purin-2-yl}amino)-3-methyl-butan-1-ol,
N6-(2-hydroxy-5-methoxybenzyl)-N2-(4-aminocyclohexyl)-9-(methyl)-9H-purin-2,6-diamine,
N6-(2-hydroxy-5-methoxybenzyl)-N2-(4-aminocyclohexyl)-9-(ethyl)-9H-purin-2,6-diamine,
N6-(2-hydroxy-5-methoxybenzyl)-N2-(4-aminocyclohexyl)-9-(isopropyl)-9H-purin-2,6-diamine,
N6-(2-hydroxy-5-methoxybenzyl)-N2-(4-aminocyclohexyl)-9-(3-pentyl)-9H-purin-2,6-diamine,
N6-(2-hydroxy-5-methoxybenzyl)-N2-(4-aminocyclohexyl)-9-(cyklohexyl)-9H-purin-2,6-diamine,
N6-(2-hydroxy-5-methoxybenzyl)-N2-(4-aminocyclohexyl)-9-(benzyl)-9H-purin-2,6-diamine,
1-({6-[(2-hydroxy-5-methoxybenzyl)amino]-9-(methyl)-9H-purin-2-yl}amino)-2-methyl-propan-2-ol,
1-({6-[(2-hydroxy-5-methoxybenzyl)amino]-9-(ethyl)-9H-purin-2-yl}amino)-2-methyl-propan-2-ol,
1-({6-[(2-hydroxy-5-methoxybenzyl)amino]-9-(isopropyl)-9H-purin-2-yl}amino)-2-methyl-propan-2-ol,
1-({6-[(2-hydroxy-5-methoxybenzyl)amino]-9-(3-pentyl)-9H-purin-2-yl}amino)-2-methyl-propan-2-ol,
1-({6-[(2-hydroxy-5-methoxybenzyl)amino]-9-(cyklohexyl)-9H-purin-2-yl}amino)-2-methyl-propan-2-ol,
1-({6-[(2-hydroxy-5-methoxybenzyl)amino]-9-(benzyl)-9H-purin-2-yl}amino)-2-methyl-propan-2-ol,
3-({6-[(2-hydroxy-5-methoxybenzyl)amino]-9-(methyl)-9H-purin-2-yl}amino)-2-methyl-butan-2-ol,
3-({6-[(2-hydroxy-5-methoxybenzyl)amino]-9-(ethyl)-9H-purin-2-yl}amino)-2-methyl-butan-2-ol,
3-({6-[(2-hydroxy-5-methoxybenzyl)amino]-9-(isopropyl)-9H-purin-2-yl}amino)-2-methyl-butan-2-ol,
3-({6-[(2-hydroxy-5-methoxybenzyl)amino]-9-(3-pentyl)-9H-purin-2-yl}amino)-2-methyl-butan-2-ol,
3-({6-[(2-hydroxy-5-methoxybenzyl)amino]-9-(cyklohexyl)-9H-purin-2-yl}amino)-2-methyl-butan-2-ol,
3-({6-[(2-hydroxy-5-methoxybenzyl)amino]-9-(benzyl)-9H-purin-2-yl}amino)-2-methyl-butan-2-ol,
4-({6-[(2-hydroxy-5-methoxybenzyl)amino]-9-(methyl)-9H-purin-2-yl}amino)-2-methyl-butan-2-ol,
4-({6-[(2-hydroxy-5-methoxybenzyl)amino]-9-(ethyl)-9H-purin-2-yl}amino)-2-methyl-butan-2-al, 4-({6-[(2-hydroxy-5-methoxybenzyl)amino]-9-(isopropyl)-9H-purin-2-yl}amino)-2-methyl-butan-2-ol,
4-({6-[(2-hydroxy-5-methoxybenzyl)amino]-9-(3-pentyl)-9H-purin-2-yl}amino)-2-methyl-butan-2-ol,
4-({6-[(2-hydroxy-5-methoxybenzyl)amino]-9-(cyklohexyl)-9H-purin-2-yl}amino)-2-methyl-butan-2-ol,
4-({6-[(2-hydroxy-5-methoxybenzyl)amino]-9-(benzyl)-9H-purin-2-yl}amino)-2-methyl-butan-2-ol,
4-({6-[(2-hydroxy-5-methoxybenzyl)amino]-9-(methyl)-9H-purin-2-yl}amino)-2-methyl-pentan-2-ol,
4-({6-[(2-hydroxy-5-methoxybenzyl)amino]-9-(ethyl)-9H-purin-2-yl}amino)-2-methyl-pentan-2-ol,
4-({6-[(2-hydroxy-5-methoxybenzyl)amino]-9-(isopropyl)-9H-purin-2-yl}amino)-2-methyl-pentan-2-ol,
4-({6-[(2-hydroxy-5-methoxybenzyl)amino]-9-(3-pentyl)-9H-purin-2-yl}amino)-2-methyl-pentan-2-ol,
4-({6-[(2-hydroxy-5-methoxybenzyl)amino]-9-(cyklohexyl)-9H-purin-2-yl}amino)-2-methyl-pentan-2-ol,
4-({6-[(2-hydroxy-5-methoxybenzyl)amino]-9-(benzyl)-9H-purin-2-yl}amino)-2-methyl-pentan-2-ol,
4-({6-[(2-hydroxy-5-methoxybenzyl)amino]-9-(methyl)-9H-purin-2-yl}amino)-2,3-dimethyl-butan-2-ol,
4-({6-[(2-hydroxy-5-methoxybenzyl)amino]-9-(ethyl)-9H-purin-2-yl}amino)-2,3-dimethyl-butan-2-ol,
4-({6-[(2-hydroxy-5-methoxybenzyl)amino]-9-(isopropyl)-9H-purin-2-yl}amino)-2,3-dimeth yl-butan-2-ol,
4-({6-[(2-hydroxy-5-methoxybenzyl)amino]-9-(3-pentyl)-9H-purin-2-yl}amino)-2,3-dimethyl-butan-2-ol,
4-({6-[(2-hydroxy-5-methoxybenzyl)amino]-9-(cyklohexyl)-9H-purin-2-yl}amino)-2,3-dimethyl-butan-2-ol,
4-({6-[(2-hydroxy-5-methoxybenzyl)amino]-9-(benzyl)-9H-purin-2-yl}amino)-2,3-dimethyl-butan-2-ol,
3-({6-[(2-hydroxy-5-methoxybenzyl)amino]-9-(methyl)-9H-purin-2-yl}amino)-2-methyl-pentan-2-ol,
3-({6-[(2-hydroxy-5-methoxybenzyl)amino]-9-(ethyl)-9H-purin-2-yl}amino)-2-methyl-pentan-2-ol,
3-({6-[(2-hydroxy-5-methoxybenzyl)amino]-9-(isopropyl)-9H-purin-2-yl}amino)-2-methyl-pentan-2-ol,
3-({6-[(2-hydroxy-5-methoxybenzyl)amino]-9-(3-pentyl)-9H-purin-2-yl}amino)-2-methyl-pentan-2-ol,
3-({6-[(2-hydroxy-5-methoxybenzyl)amino]-9-(cyklohexyl)-9H-purin-2-yl}amino)-2-methyl-pentan-2-ol,
3-({6-[(2-hydroxy-5-methoxybenzyl)amino]-9-(benzyl)-9H-purin-2-yl}amino)-2-methyl-pentan-2-ol,
3-({6-[(2-hydroxy-5-methoxybenzyl)amino]-9-(methyl)-9H-purin-2-yl]amino}pentan-2-ol,
3-({6-[(2-hydroxy-5-methoxybenzyl)amino]-9-(ethyl)-9H-purin-2-yl]amino}pentan-2-ol,
3-({6-[(2-hydroxy-5-methoxybenzyl)amino]-9-(isopropyl)-9H-purin-2-yl]amino}pentan-2-ol
3-({6-[(2-hydroxy-5-methoxybenzyl)amino]-9-(3-pentyl)-9H-purin-2-yl]amino}pentan-2-ol,
3-({6-[(2-hydroxy-5-methoxybenzyl)amino]-9-(cyklohexyl)-9H-purin-2-yl]amino}pentan-2-ol,
3-({6-[(2-hydroxy-5-methoxybenzyl)amino]-9-(benzyl)-9H-purin-2-yl]amino}pentan-2-ol,
1-({6-[(2-hydroxy-5-methoxybenzyl)amino]-9-(methyl)-9H-purin-2-yl}amino)-2-methyl-propan-2-ol,
1-({6-[(2-hydroxy-5-methoxybenzyl)amino]-9-(ethyl)-9H-purin-2-yl}amino)-2-methyl-propan-2-ol,
1-({6-[(2-hydroxy-5-methoxybenzyl)amino]-9-(isopropyl)-9H-purin-2-yl}amino)-2-methyl-propan-2-ol,
1-({6-[(2-hydroxy-5-methoxybenzyl)amino]-9-(3-pentyl)-9H-purin-2-yl}amino)-2-methyl-propan-2-ol,
1-({6-[(2-hydroxy-5-methoxybenzyl)amino]-9-(cyklohexyl)-9H-purin-2-yl}amino)-2-methyl-propan-2-ol,
1-({6-[(2-hydroxy-5-methoxybenzyl)amino]-9-(benzyl)-9H-purin-2-yl}amino)-2-methyl-propan-2-ol,
3-({6-[(2-hydroxy-5-mercaptobenzyl)amino]-9-methyl-9H-purin-2-yl}amino)-2-methyl-pentan-2-ol,
3-({6-[(2-hydroxy-5-mercaptobenzyl)amino]-9-ethyl-9H-purin-2-yl}amino)-2-methyl-pentan-2-ol,
3-({6-[(2-hydroxy-5-mercaptobenzyl)amino]-9-isopropyl-9H-purin-2-yl}amino)-2-methyl-pentan-2-ol,
3-({6-[(2-hydroxy-5-mercaptobenzyl)amino]-9-cyclohexyl-9H-purin-2-yl}amino)-2-methyl-pentan-2-ol,
3-({6-[(2-hydroxy-5-mercaptobenzyl)amino]-9-benzyl-9H-purin-2-yl}amino)-2-methyl-pentan-2-ol,
3-({6-[(2-hydroxy-5-mercaptobenzyl)amino]-9-methyl-9H-purin-2-yl]amino}pentan-2-ol,
3-({6-[(2-hydroxy-5-mercaptobenzyl)amino]-9-ethyl-9H-purin-2-yl]amino}pentan-2-ol,
3-({6-[(2-hydroxy-5-mercaptobenzyl)amino]-9-isopropyl-9H-purin-2-yl]amino}pentan-2-ol, 3-({6-[(2-hydroxy-5-mercaptobenzyl)amino]-9-cyclohexyl-9H-purin-2-yl]amino}pentan-2-ol,
3-({6-[(2-hydroxy-5-mercaptobenzyl)amino]-9-benzyl-9H-purin-2-yl]amino}pentan-2-ol,
1-({6-[(2-hydroxy-5-mercaptobenzyl)amino]-9-cyclopropyl-9H-purin-2-yl}amino)-2-methyl-propan-2-ol,
1-({6-[(2-hydroxy-5-mercaptobenzyl)amino]-9-cyclohexyl-9H-purin-2-yl}amino)-2-methyl-propan-2-ol,
1-({6-[(2-hydroxy-5-mercaptobenzyl)amino]-9-benzyl-9H-purin-2-yl}amino)-2-methyl-propan-2-ol,
3-({6-[(2-hydroxy-5-nitrobenzyl)amino]-9-methyl-9H-purin-2-yl}amino)-2-methyl-pentan-2-ol,
3-({6-[(2-hydroxy-5-nitrobenzyl)amino]-9-ethyl-9H-purin-2-yl}amino)-2-methyl-pentan-2-ol,
3-({6-[(2-hydroxy-5-nitrobenzyl)amino]-9-isopropyl-9H-purin-2-yl}amino)-2-methyl-pentan-2-ol,
3-({6-[(2-hydroxy-5-nitrobenzyl)amino]-9-cyclohexyl-9H-purin-2-yl}amino)-2-methyl-pentan-2-ol,
3-({6-[(2-hydroxy-5-nitrobenzyl)amino]-9-benzyl-9H-purin-2-yl}amino)-2-methyl-pentan-2-ol,
3-({6-[(2-hydroxy-5-nitrobenzyl)amino]-9-methyl-9H-purin-2-yl]amino}pentan-2-ol,
3-({6-[(2-hydroxy-5-nitrobenzyl)amino]-9-ethyl-9H-purin-2-yl]amino}pentan-2-ol,
3-({6-[(2-hydroxy-5-nitrobenzyl)amino]-9-isopropyl-9H-purin-2-yl]amino}pentan-2-ol,
3-({6-[(2-hydroxy-5-nitrobenzyl)amino]-9-cyclohexyl-9H-purin-2-yl]amino}pentan-2-ol,
3-({6-[(2-hydroxy-5-nitrobenzyl)amino]-9-benzyl-9H-purin-2-yl]amino}pentan-2-ol,
1-({6-[(2-hydroxy-5-nitrobenzyl)amino]-9-cyclopropyl-9H-purin-2-yl}amino)-2-methyl-propan-2-ol,
1-({6-[(2-hydroxy-5-nitrobenzyl)amino]-9-cyclohexyl-9H-purin-2-yl}amino)-2-methyl-propan-2-ol,
1-({6-[(2-hydroxy-5-nitrobenzyl)amino]-9-benzyl-9H-purin-2-yl}amino)-2-methyl-propan-2-ol,
2-({6-[(2-hydroxy-5-aminobenzyl)amino]-9-(methyl)-9H-purin-2-yl}amino)butan-1-ol,
2-({6-[(2-hydroxy-5-aminobenzyl)amino]-9-(ethyl)-9H-purin-2-yl}amino)butan-1-ol,
2-({6-[(2-hydroxy-5-aminobenzyl)amino]-9-(isopropyl)-9H-purin-2-yl}amino)butan-1-ol,
2-({6-[(2-hydroxy-5-aminobenzyl)amino]-9-(3-pentyl)-9H-purin-2-yl}amino)butan-1-ol,
2-({6-[(2-hydroxy-5-aminobenzyl)amino]-9-(cyklohexyl)-9H-purin-2-yl}amino)butan-1-ol,
2-({6-[(2-hydroxy-5-aminobenzyl)amino]-9-(benzyl)-9H-purin-2-yl}amino)butan-1-ol,
N6-(2-hydroxy-5-aminobenzyl)-N2-(2-aminopropyl)-9-(methyl)-9H-purin-2,6-diamine,
N6-(2-hydroxy-5-aminobenzyl)-N2-(2-aminopropyl)-9-(ethyl)-9H-purin-2,6-diamine,
N6-(2-hydroxy-5-aminobenzyl)-N2-(2-aminopropyl)-9-(isopropyl)-9H-purin-2,6-diamine,
N6-(2-hydroxy-5-aminobenzyl)-N2-(2-aminopropyl)-9-(3-pentyl)-9H-purin-2,6-diamine,
N6-(2-hydroxy-5-aminobenzyl)-N2-(2-aminopropyl)-9-(cyklohexyl)-9H-purin-2,6-diamine,
N6-(2-hydroxy-5-aminobenzyl)-N2-(2-aminopropyl)-9-(benzyl)-9H-purin-2,6-diamine,
2-({6-[(2-hydroxy-5-aminobenzyl)amino]-9-(methyl)-9H-purin-2-yl}amino)-3-methyl-butan-1-ol,
2-({6-[(2-hydroxy-5-aminobenzyl)amino]-9-(ethyl)-9H-purin-2-yl}amino)-3-methyl-butan-1-ol,
2-({6-[(2-hydroxy-5-aminobenzyl)amino]-9-(isopropyl)-9H-purin-2-yl}amino)-3-methyl-butan-1-ol,
2-({6-[(2-hydroxy-5-aminobenzyl)amino]-9-(3-pentyl)-9H-purin-2-yl}amino)-3-methyl-butan-1-ol,
2-({6-[(2-hydroxy-5-aminobenzyl)amino]-9-(cyklohexyl)-9H-purin-2-yl}amino)-3-methyl-butan-1-ol,
2-({6-[(2-hydroxy-5-aminobenzyl)amino]-9-(benzyl)-9H-purin-2-yl}amino)-3-methyl-butan-1-ol,
N6-(2-hydroxy-5-aminobenzyl)-N2-(4-aminocyclohexyl)-9-(methyl)-9H-purin-2,6-diamine,
N6-(2-hydroxy-5-aminobenzyl)-N2-(4-aminocyclohexyl)-9-(ethyl)-9H-purin-2,6-diamine,
N6-(2-hydroxy-5-aminobenzyl)-N2-(4-aminocyclohexyl)-9-(isopropyl)-9H-purin-2,6-diamine,
N6-(2-hydroxy-5-aminobenzyl)-N2-(4-aminocyclohexyl)-9-(3-pentyl)-9H-purin-2,6-diamine,
N6-(2-hydroxy-5-aminobenzyl)-N2-(4-aminocyclohexyl)-9-(cyklohexyl)-9H-purin-2,6-diamine,
N6-(2-hydroxy-5-aminobenzyl)-N2-(4-aminocyclohexyl)-9-(benzyl)-9H-purin-2,6-diamine,
1-({6-[(2-hydroxy-5-aminobenzyl)amino]-9-(methyl)-9H-purin-2-yl}amino)-2-methyl-propan-2-ol,
1-({6-[(2-hydroxy-5-aminobenzyl)amino]-9-(ethyl)-9H-purin-2-yl}amino)-2-methyl-propan-2-ol,
1-({6-[(2-hydroxy-5-aminobenzyl)amino]-9-(isopropyl)-9H-purin-2-yl}amino)-2-methyl-propan-2-ol,
1-({6-[(2-hydroxy-5-aminobenzyl)amino]-9-(3-pentyl)-9H-purin-2-yl}amino)-2-methyl-propan-2-ol,
1-({6-[(2-hydroxy-5-aminobenzyl)amino]-9-(cyklohexyl)-9H-purin-2-yl}amino)-2-methyl-propan-2-ol,
1-({6-[(2-hydroxy-5-aminobenzyl)amino]-9-(benzyl)-9H-purin-2-yl}amino)-2-methyl-propan-2-ol,
3-({6-[(2-hydroxy-5-aminobenzyl)amino]-9-(methyl)-9H-purin-2-yl}amino)-2-methyl-butan-2-ol,
3-({6-[(2-hydroxy-5-aminobenzyl)amino]-9-(ethyl)-9H-purin-2-yl}amino)-2-methyl-butan-2-ol,
3-({6-[(2-hydroxy-5-aminobenzyl)amino]-9-(isopropyl)-9H-purin-2-yl}amino)-2-methyl-butan-2-ol,
3-({6-[(2-hydroxy-5-aminobenzyl)amino]-9-(3-pentyl)-9H-purin-2-yl}amino)-2-methyl-butan-2-ol,
3-({6-[(2-hydroxy-5-aminobenzyl)amino]-9-(cyklohexyl)-9H-purin-2-yl}amino)-2-methyl-butan-2-ol,
3-({6-[(2-hydroxy-5-aminobenzyl)amino]-9-(benzyl)-9H-purin-2-yl}amino)-2-methyl-butan-2-ol,
4-({6-[(2-hydroxy-5-aminobenzyl)amino]-9-(methyl)-9H-purin-2-yl}amino)-2-methyl-butan-2-ol,
4-({6-[(2-hydroxy-5-aminobenzyl)amino]-9-(ethyl)-9H-purin-2-yl}amino)-2-methyl-butan-2-ol,
4-({6-[(2-hydroxy-5-aminobenzyl)amino]-9-(isopropyl)-9H-purin-2-yl}amino)-2-methyl-butan-2-ol,
4-({6-[(2-hydroxy-5-aminobenzyl)amino]-9-(3-pentyl)-9H-purin-2-yl}amino)-2-methyl-butan-2-ol,
4-({6-[(2-hydroxy-5-aminobenzyl)amino]-9-(cyklohexyl)-9H-purin-2-yl}amino)-2-methyl-butan-2-ol,
4-({6-[(2-hydroxy-5-aminobenzyl)amino]-9-(benzyl)-9H-purin-2-yl}amino)-2-methyl-butan-2-ol,
4-({6-[(2-hydroxy-5-aminobenzyl)amino]-9-(methyl)-9H-purin-2-yl}amino)-2-methyl-pentan-2-ol,
4-({6-[(2-hydroxy-5-aminobenzyl)amino]-9-(ethyl)-9H-purin-2-yl}amino)-2-methyl-pentan-2-ol,
4-({6-[(2-hydroxy-5-aminobenzyl)amino]-9-(isopropyl)-9H-purin-2-yl}amino)-2-methyl-pentan-2-ol,
4-({6-[(2-hydroxy-5-aminobenzyl)amino]-9-(3-pentyl)-9H-purin-2-yl}amino)-2-methyl-pentan-2-ol,
4-({6-[(2-hydroxy-5-aminobenzyl)amino]-9-(cyklohexyl)-9H-purin-2-yl}amino)-2-methyl-pentan-2-ol,
4-({6-[(2-hydroxy-5-aminobenzyl)amino]-9-(benzyl)-9H-purin-2-yl}amino)-2-methyl-pentan-2-ol, 1-({6-[(2-hydroxy-5-aminobenzyl)amino]-9-(methyl)-9H-purin-2-yl}amino)propan-2-ol,
1-({6-[(2-hydroxy-5-aminobenzyl)amino]-9-(ethyl)-9H-purin-2-yl}amino)propan-2-ol,
1-({6-[(2-hydroxy-5-aminobenzyl)amino]-9-(isopropyl)-9H-purin-2-yl}amino)propan-2-ol,
1-({6-[(2-hydroxy-5-aminobenzyl)amino]-9-(3-pentyl)-9H-purin-2-yl}amino)propan-2-ol,
1-({6-[(2-hydroxy-5-aminobenzyl)amino]-9-(cyklohexyl)-9H-purin-2-yl}amino)propan-2-ol,
1-({6-[(2-hydroxy-5-aminobenzyl)amino]-9-(benzyl)-9H-purin-2-yl}amino)propan-2-ol,
4-({6-[(2-hydroxy-5-aminobenzyl)amino]-9-(methyl)-9H-purin-2-yl}amino)-2,3-dimethyl-butan-2-ol,
4-({6-[(2-hydroxy-5-aminobenzyl)amino]-9-(ethyl)-9H-purin-2-yl}amino)-2,3-dimethyl-butan-2-ol,
4-({6-[(2-hydroxy-5-aminobenzyl)amino]-9-(isopropyl)-9H-purin-2-yl}amino)-2,3-dimethyl-butan-2-ol,
4-({6-[(2-hydroxy-5-aminobenzyl)amino]-9-(3-pentyl)-9H-purin-2-yl}amino)-2,3-dimethyl-butan-2-ol,
4-({6-[(2-hydroxy-5-aminobenzyl)amino]-9-(cyklohexyl)-9H-purin-2-yl}amino)-2,3-dimethyl-butan-2-ol,
4-({6-[(2-hydroxy-5-aminobenzyl)amino]-9-(benzyl)-9H-purin-2-yl}amino)-2,3-dimethyl-butan-2-ol,
3-({6-[(2-hydroxy-5-aminobenzyl)amino]-9-(methyl)-9H-purin-2-yl}amino)-2-methyl-pentan-2-ol,
3-({6-[(2-hydroxy-5-aminobenzyl)amino]-9-(ethyl)-9H-purin-2-yl}amino)-2-methyl-pentan-2-ol,
3-({6-[(2-hydroxy-5-aminobenzyl)amino]-9-(isopropyl)-9H-purin-2-yl}amino)-2-methyl-pentan-2-ol,
3-({6-[(2-hydroxy-5-aminobenzyl)amino]-9-(3-pentyl)-9H-purin-2-yl}amino)-2-methyl-pentan-2-ol,
3-({6-[(2-hydroxy-5-aminobenzyl)amino]-9-(cyklohexyl)-9H-purin-2-yl}amino)-2-methyl-pentan-2-ol,
3-({6-[(2-hydroxy-5-aminobenzyl)amino]-9-(benzyl)-9H-purin-2-yl}amino)-2-methyl-pentan-2-ol,
3-({6-[(2-hydroxy-5-aminobenzyl)amino]-9-(methyl)-9H-purin-2-yl]amino}pentan-2-ol,
3-({6-[(2-hydroxy-5-aminobenzyl)amino]-9-(ethyl)-9H-purin-2-yl]amino}pentan-2-ol,
3-({6-[(2-hydroxy-5-aminobenzyl)amino]-9-(isopropyl)-9H-purin-2-yl]amino}pentan-2-ol,
3-({6-[(2-hydroxy-5-aminobenzyl)amino]-9-(3-pentyl)-9H-purin-2-yl]amino}pentan-2-ol,
3-({6-[(2-hydroxy-5-aminobenzyl)amino]-9-(cyklohexyl)-9H-purin-2-yl]amino}pentan-2-ol,
3-({6-[(2-hydroxy-5-aminobenzyl)amino]-9-(benzyl)-9H-purin-2-yl]amino}pentan-2-ol,
1-({6-[(2-hydroxy-5-aminobenzyl)amino]-9-(methyl)-9H-purin-2-yl}amino)-2-methyl-propan-2-ol,
1-({6-[(2-hydroxy-5-aminobenzyl)amino]-9-(ethyl)-9H-purin-2-yl}amino)-2-methyl-propan-2-ol,
1-({6-[(2-hydroxy-5-aminobenzyl)amino]-9-(isopropyl)-9H-purin-2-yl}amino)-2-methyl-propan-2-ol,
1-({6-[(2-hydroxy-5-aminobenzyl)amino]-9-(3-pentyl)-9H-purin-2-yl}amino)-2-methyl-propan-2-ol,
1-({6-[(2-hydroxy-5-aminobenzyl)amino]-9-(cyklohexyl)-9H-purin-2-yl}amino)-2-methyl-propan-2-ol, and
1-({6-[(2-hydroxy-5-aminobenzyl)amino]-9-(benzyl)-9H-purin-2-yl}amino)-2-methyl-propan-2-ol.

6. A compound of formula I

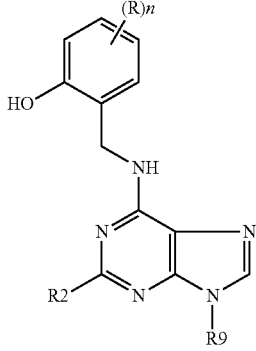

wherein
(R)n represents n substituents R, which can be the same or different, the substituents R being selected from the group consisting of alkyl, alkoxy, amino, halogen, mercapto and nitro, wherein n is from 1 to 4, and
R2 is R2'—NH— wherein
R2' is selected from the group consisting of alkyl, alkenyl, cycloalkyl, cycloalkyl alkyl, aryl, and arylalkyl, wherein each of the groups can optionally be substituted by one or more substituents selected from the group consisting of amino, mercapto, and alkoxy, and
R9 is selected from the group consisting of alkyl, alkenyl, cycloalkyl, cycloalkyl alkyl, aryl and arylalkyl group,
or a pharmaceutically acceptable salt thereof.

* * * * *